US008153641B2

(12) United States Patent
Ibrahim et al.

(10) Patent No.: US 8,153,641 B2
(45) Date of Patent: Apr. 10, 2012

(54) COMPOUNDS AND METHODS FOR KINASE MODULATION, AND INDICATIONS THEREFOR

(75) Inventors: Prabha N. Ibrahim, Mountain View, CA (US); Wayne Spevak, Berkeley, CA (US); Hanna Cho, Oakland, CA (US); Songyuan Shi, Fremont, CA (US)

(73) Assignee: Plexxikon Inc., Berkeley, CA (US)

( * ) Notice: Subject to any disclaimer, the term of this patent is extended or adjusted under 35 U.S.C. 154(b) by 151 days.

(21) Appl. No.: 12/467,208

(22) Filed: May 15, 2009

(65) Prior Publication Data

US 2009/0286783 A1    Nov. 19, 2009

Related U.S. Application Data

(60) Provisional application No. 61/054,445, filed on May 19, 2008, provisional application No. 61/163,812, filed on Mar. 26, 2009.

(51) Int. Cl.
*A01N 43/90* (2006.01)
*A61K 31/519* (2006.01)
*C07D 487/00* (2006.01)

(52) U.S. Cl. ..................... 514/265.1; 544/280
(58) Field of Classification Search .......... None
See application file for complete search history.

(56) References Cited

U.S. PATENT DOCUMENTS

| 3,575,977 A * | 4/1971 | Kim, et al. .............. 544/280 |
| 7,271,262 B2 | 9/2007 | La Greca et al. |
| 2004/0077595 A1 | 4/2004 | Cheng et al. |
| 2007/0032519 A1 | 2/2007 | Zhang et al. |

FOREIGN PATENT DOCUMENTS

| WO | WO 2004/056830 | 7/2004 |
| WO | WO 2005/116035 | 12/2005 |
| WO | WO 2007/002433 | 1/2007 |
| WO | WO 2007/013896 | 2/2007 |

OTHER PUBLICATIONS

Wolff et. al., "Burger's Medicinal Chemistry and Drug Discovery," 5th Ed. Part 1, pp. 975-977 (1995).*
Banker, et. al., Modern Pharmaceuticals, (1996), p. 596.*
Dorwald F. A. Side Reactions in Organic Synthesis, 2005, Wiley: VCH, Weinheim p. IX of Preface.*
U.S. Appl. No. 10/473,347, filed May 4, 2004, Wei Shao.
PCT International Search Report for Application No. PCT/US2009/004178 dated Nov. 10, 2009.
U.S. Appl. No. 11/473,347, filed Jun. 21, 2006, Ibrahim et al.
Bagshawe, K.D., Antibody-Directed Enzyme Prodrug Therapy: A Review, *Drug Dev. Res.*, 34:220-230 (1995).
Balak, et. al., Novel D761Y and Common Secondary T790M Mutations in Epidermal Growth Factor Receptor—Mutant Lung Adenocarcinomas with Acquired Resistance to Kinase Inhibitors, Clin Cancer Res. 12:6494-501 (2006).
Bertolini et al., A New Rational Hypothesis for the Pharmacophore of the Active Metabolite of Leflunomide, a Potent Immunosuppressive Drug, *J. Med. Chem.*, 40:2011-2016 (1997).
Crump, M., Inhibition of Raf Kinase in the Treatment of Acute Myeloid Leukemia, Curr Pharm Des 8(25):2243-8 (2002).
Engelman et al., Effective use of PI3K and MEK inhibitors to treat mutant *Kras* G121D and *PIK3CA* H1047R murine lung cancers, Nature medicine. 14(12):1351-1355 (2008).
Garzya et al., Indium(III)-catalysed aryl sulfonylation reactions, Tetrahedron Lett. 45:1499-1501 (2004).
Girgis, N. et.al., The Synthesis of 5-Azaindoles by Substitution-Rearrangement of 7-Azaindoles upon Treatment with Certain Primary Amines, J. Heterocyclic. Chem. 26:317-325 (1989).
Hood, J.D. et al., Tumor Regression by Targeted Gene Delivery Neovasculature, Science 296, 2404 (2002).
Kunnimalaiyaan, M. and Chen, H., The Raf-1 pathway: a molecular target for treatment of select neuroendocrine tumors? Anticancer Drugs, 17(2):139-42 (2006).
Miyaura and Suzuki, Palladium-catalyzed cross-coupling reactions of organoboron compounds. Chem. Rev. 95:2457-2483 (1995).
Niihori et al., Germline *KRAS* and *BRAF* mutations in cardio-facio-cutaneous syndrome, Nat Genet., 38(3):294-6 (2006).
*Remington's Pharmaceutical Sciences*, 19th ed., Mack Publishing Co., Easton, PA, vol. 2, p. 1454-1460, 1995.
Shan et al., Prodrug Strategies Based on Intramolecular Cyclization Reactions, *J Pharm Sci* 86(7):765-767 (1997).

* cited by examiner

*Primary Examiner* — Jeffrey Murray
(74) *Attorney, Agent, or Firm* — Foley & Lardner LLP; Stephen E. Reiter

(57) ABSTRACT

Compounds and salts thereof, formulations thereof, conjugates thereof, derivatives thereof, forms thereof and uses thereof are described. In certain aspects and embodiments, the described compounds or salts thereof, formulations thereof, conjugates thereof derivatives thereof, forms thereof are active on at least one Raf protein kinase. Also described are methods of use thereof to treat diseases and conditions, including diseases and conditions associated with activity of Raf protein kinases, including melanoma, colorectal cancer, thyroid cancer, ovarian cancer, cholangiocarcinoma, pain or polycystic kidney disease.

8 Claims, No Drawings

COMPOUNDS AND METHODS FOR KINASE MODULATION, AND INDICATIONS THEREFOR

CROSS-REFERENCE TO RELATED APPLICATIONS

This patent application claims priority to U.S. Provisional Patent Application No. 61/163,812, entitled "Compounds and Methods for Kinase Modulation, and Indications Therefor," filed Mar. 26, 2009 and U.S. Provisional Patent Application No. 61/054,445, entitled "Compounds and Methods for Kinase Modulation, and Indications Therefor," filed May 19, 2008, which are hereby incorporated by reference in their entirety for all purposes.

FIELD OF THE INVENTION

Disclosed are novel compounds and uses thereof. In certain embodiments disclosed compounds are kinase inhibitors.

SUMMARY OF THE INVENTION

In certain aspects and embodiments disclosed herein, compounds are provided, as well as various salts thereof, formulations thereof, conjugates thereof, derivatives thereof, forms thereof and uses thereof. Also contemplated in accordance with the present invention are methods for the use of the compounds in treating diseases and conditions associated with regulation of the activity of one or more protein kinases in general, including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, FRk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and/or Zap70, including any mutations of these kinases. Thus, the use of compounds for therapeutic methods involving modulation of protein kinases are provided. In certain embodiments, the compounds are active on one or more Raf kinases, including A-Raf, B-Raf and/or c-Raf-1, including any mutations thereof. In certain embodiments, the compounds are used for therapeutic methods involving modulation of one or more Raf protein kinases, including treatment of a variety of indications, including, but not limited to, melanoma, colorectal cancer, thyroid cancer, ovarian cancer, cholangiocarcinoma, pain and polycystic kidney disease. In some embodiments, compounds are of Formula I, Formula Ia, or Formula Ib as described below.

In a first aspect, compounds having the structure according to the following Formula I are provided:

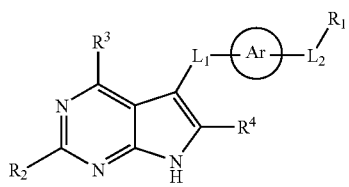

Formula I or a salt, a prodrug, a tautomer or a stereoisomer thereof, wherein:
Ar is selected from the group consisting of:

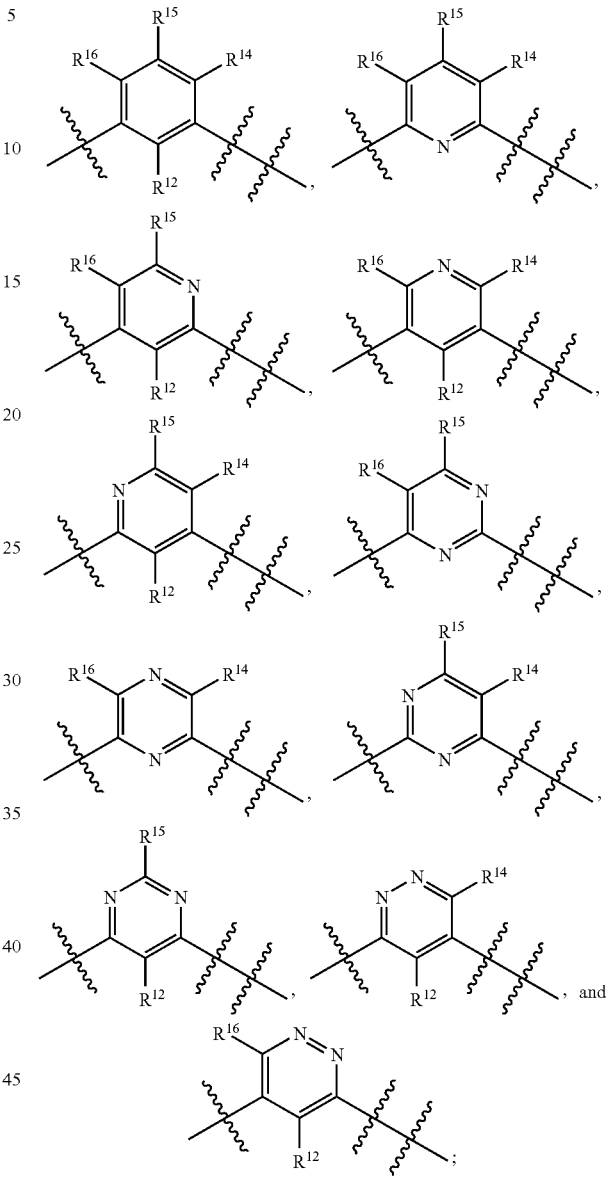

wherein

indicates the point of attachment of Ar to $L_1$ of Formula I and

indicates the point of attachment of Ar to $L_2$ of Formula I;

$L_1$ is selected from the group consisting of $-C(R^5R^6)-$, $-C(O)-$, $-C(S)-$, $-N(R^7)-$, $-O-$, $-S-$, $-S(O)-$, and $-S(O)_2-$;

$L_2$ is selected from the group consisting of $-N(R^8)-C(O)-$, $-N(R^8)-C(S)-$, $-N(R^8)-S(O)-$, $-N(R^8)-S(O)_2-$, $-N(R^8)-C(O)-N(R^8)-$, $-N(R^8)-C(S)-N(R^8)-$, and $-N(R^8)-S(O)_2-N(R^8)-$;

$R^1$ is selected from the group consisting of optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

$R^2$ is selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, $-CN$, $-NO_2$, $-O-R^9$, $-S-R^{11}$, $-N(R^9)-R^{10}$, $-C(O)-R^{11}$, $-C(S)-R^{11}$, $-C(O)-N(R^9)-R^{10}$, $-C(S)-N(R^9)-R^{10}$, $-C(O)-N(R^{13})-OR^9$, $-C(S)-N(R^{13})-OR^9$, $-C(O)-N(R^{13})-S(O)_2-R^{11}$, $-C(S)-N(R^{13})-S(O)_2-R^{11}$, $-C(O)-O-R^9$, $-S(O)-R^{11}$, $-S(O)_2-R^{11}$, $-S(O)-N(R^9)-R^{10}$, $-S(O)_2-N(R^9)-R^{10}$, $-S(O)_2-N(R^{13})-C(O)R^{11}$, $-S(O)_2-N(R^{13})-C(S)R^{11}$, $-N(R^{13})-C(O)-R^{11}$, $-N(R^{13})-C(S)-R^{11}$, $-N(R^{13})-S(O)-R^{11}$, $-N(R^{13})-S(O)_2-R^{11}$, $-N(R^{13})-C(O)-N(R^9)-R^{10}$, $-N(R^{13})-C(S)-N(R^9)-R^{10}$, and $-N(R^{13})-S(O)_2-N(R^9)-R^{10}$;

$R^3$ is selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, $-CN$, $-NO_2$, $-O-R^{19}$, $-S-R^{19}$, $-C(O)-R^{19}$, $-C(S)-R^{19}$, $-C(O)-N(R^{17})-R^{18}$, $-C(S)-N(R^{17})-R^{18}$, $-C(O)-N(R^{20})-OR^{17}$, $-C(S)-N(R^{20})-OR^{17}$, $-C(O)-N(R^{20})-S(O)_2-R^{19}$, $-C(S)-N(R^{20})-S(O)_2-R^{19}$, $-C(O)-O-R^{17}$, $-S(O)-R^{19}$, $-S(O)_2-R^{19}$, $-S(O)-N(R^{17})-R^{18}$, $-S(O)_2-N(R^{17})-R^{18}$, $-S(O)_2-N(R^{20})-C(O)R^{19}$, $-S(O)_2-N(R^{20})-C(S)R^{19}$, $-N(R^{20})-C(O)-R^9$, $-N(R^{20})-C(S)-R^{19}$, $-N(R^{20})-S(O)-R^{19}$, $-N(R^{20})-S(O)_2-R^{19}$, $-N(R^{20})-C(O)-N(R^{17})-R^{18}$, $-N(R^{20})-C(S)-N(R^{17})-R^{18}$, and $-N(R^{20})-S(O)_2-N(R^{17})-R^{18}$;

$R^4$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, $-CN$, $-NO_2$, $-O-R^{21}$, $-S-R^{23}$, $-N(R^{21})-R^{22}$, $-C(O)-R^{23}$, $-C(S)-R^{23}$, $-C(O)-N(R^{21})-R^{22}$, $-C(S)-N(R^{21})-R^{22}$, $-C(O)-N(R^{24})-OR^{21}$, $-C(S)-N(R^{24})-OR^{21}$, $-C(O)-N(R^{24})-S(O)_2-R^{23}$, $-C(S)-N(R^{24})-S(O)_2-R^{23}$, $-C(O)-O-R^{21}$, $-S(O)-R^{23}$, $-S(O)_2-R^{23}$, $-S(O)-N(R^{21})-R^{22}$, $-S(O)_2-N(R^{21})-R^{22}$, $-S(O)_2-N(R^{24})-C(O)R^{23}$, $-S(O)_2-N(R^{24})-C(S)R^{23}$, $-N(R^{24})C(O)-R^{23}$, $-N(R^{24})-C(S)-R^{23}$, $-NR^{24})-S(O)-R^{23}$, $-N(R^{24})-S(O)_2-R^{23}$, $-N(R^{24})-C(O)-N(R^{21})-R^{22}$, $-N(R^{24})-C(S)-N(R^{21})-R^{22}$, and $-N(R^{24})-S(O)_2-N(R^{21})-R^{22}$;

$R^5$ and $R^6$ are independently selected from the group consisting of hydrogen, fluoro, $-OH$, $-NH_2$, lower alkyl, lower alkoxy, lower alklylthio, mono-alkylamino, di-alkylamino, and $-N(R^{25})-R^{26}$, wherein the alkyl chain(s) of lower alkyl, lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino; or $R^5$ and $R^6$ combine to form a 3-7 membered monocyclic cycloalkyl or 5-7 membered monocyclic heterocycloalkyl, wherein the 3-7 membered monocyclic cycloalkyl or 5-7 membered monocyclic heterocycloalkyl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^7$, $R^{13}$, $R^{20}$, and $R^{24}$ are independently selected from the group consisting of hydrogen, optionally substituted lower alkyl, optionally substituted cycloalkyl, optionally substituted heterocycloalkyl, optionally substituted aryl, optionally substituted heteroaryl, $-C(O)-R^{27}$, $-C(S)-R^{27}$, $-S(O)-R^{27}$, $-S(O)_2-R^{27}$, $-C(O)-N(H)-R^{27}$, $-C(S)-N(H)-R^{27}$, and $-S(O)_2-N(H)-R^{27}$;

$R^8$ at each occurrence is independently hydrogen, lower alkyl, or lower alkyl substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and $-N(R^{25})-R^{26}$;

$R^{12}$, $R^{14}$, $R^{15}$, and $R^{16}$ are independently selected from the group consisting of hydrogen, halogen, optionally substituted lower alkyl, $-N(R^{28})-R^{29}$, $-O-R^{28}$, and $-S-R^{30}$;

$R^{11}$, $R^{19}$ and $R^{23}$ are independently selected from the group consisting of optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

$R^9$, $R^{10}$, $R^{17}$, $R^{18}$, $R^{21}$ and $R^{22}$ are independently selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

$R^{25}$ and $R^{26}$ at each occurrence combine with the nitrogen to which they are attached to form a 5-7 membered heterocycloalkyl optionally substituted with one or more substituents selected from the group consisting of fluoro, $-OH$, $-NH_2$, lower alkyl, fluoro substituted lower alkyl, lower alkoxy, fluoro substituted lower alkoxy, lower alkylthio, and fluoro substituted lower alkylthio;

$R^{27}$ at each occurrence is independently selected from the group consisting of optionally substituted lower alkyl, optionally substituted cycloalkyl, optionally substituted heterocycloalkyl, optionally substituted aryl, and optionally substituted heteroaryl;

$R^{28}$ and $R^{29}$ at each occurrence are independently hydrogen or optionally substituted lower alkyl; and $R^{30}$ at each occurrence is optionally substituted lower alkyl.

In a second aspect, compounds of Formula I having the structure according to the following Formula Ia are provided:

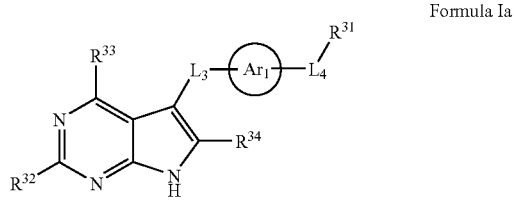

Formula Ia or a salt, a prodrug, a tautomer or a stereoisomer thereof, wherein:

$Ar_1$ is selected from the group consisting of:

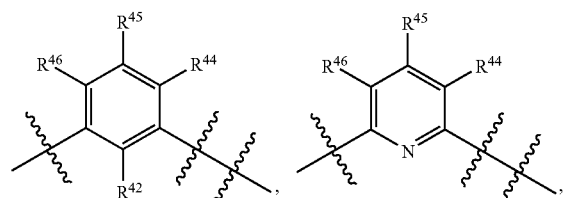

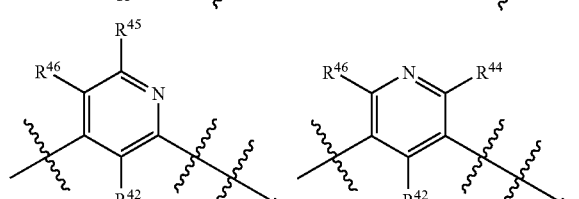

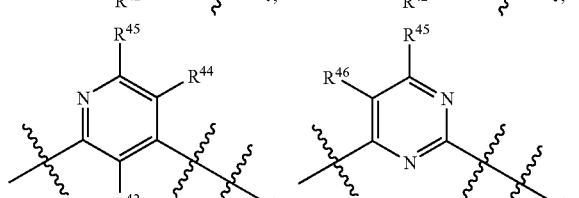

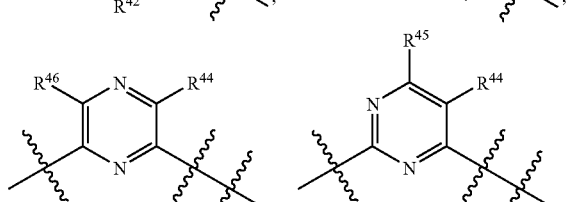

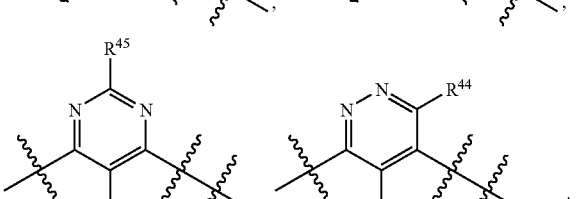

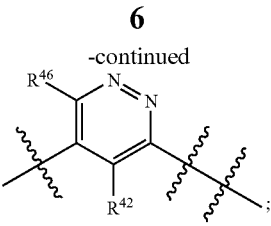

wherein

indicates the point of attachment of $Ar_1$ to $L_3$ of Formula Ia and

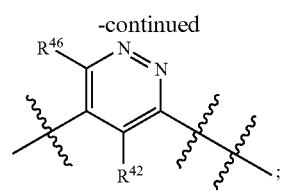

indicates the point of attachment of $Ar_1$ to $L_4$ of Formula Ia;

$L_3$ is selected from the group consisting of —C($R^{35}R^{36}$)—, —C(O)—, —C(S)—, —N($R^{37}$)—, —O—, —S—, —S(O)—, and —S(O)$_2$—;

$L_4$ is selected from the group consisting of —N($R^{38}$)—C(O)—, —N($R^{38}$)—C(S)—, —N($R^{38}$)—S(O)—, —N($R^{38}$)—S(O)$_2$—, —N($R^{38}$)—C(O)—N($R^{38}$)—, —N($R^{38}$)—C(S)—N($R^{38}$)—, and —N($R^{38}$)—S(O)$_2$—N($R^{38}$)—;

$R^{31}$ is selected from the group consisting of optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

$R^{32}$ is selected from the group consisting of hydrogen, —OH, —NH$_2$, —CN, —NO$_2$, —C(O)—OH, —S(O)—NH$_2$, —S(O)$_2$—NH$_2$, —C(O)—NH$_2$, —O—$R^{39}$, —S—$R^{39}$, —N($R^{40}$)—$R^{39}$, —N($R^{40}$)—C(O)—$R^{39}$, —N($R^{40}$)—S(O)—$R^{39}$, —N($R^{40}$)—S(O)$_2$—$R^{39}$, —C(O)—N($R^{40}$)—$R^{39}$, —C(O)—O—$R^{39}$, —C(O)—$R^{39}$, —S(O)—N($R^{40}$)—$R^{39}$, —S(O)$_2$—N($R^{40}$)—$R^{39}$, —S(O)—$R^{39}$, —S(O)$_2$—$R^{39}$, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{32}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—$R^{41}$, —S—$R^{41}$, —N($R^{40}$)—$R^{41}$, —N($R^{40}$)—C(O)—$R^{41}$, —N($R^{40}$)—S(O)—$R^{41}$, —N($R^{40}$)—S(O)$_2$—$R^{41}$, —C(O)—$R^{41}$, —S(O)—$R^{41}$, —S(O)$_2$—$R^{41}$, —C(O)—O—$R^{41}$, —C(O)—N($R^{40}$)—$R^{41}$, —S(O)—N($R^{40}$)—$R^{41}$, —S(O)$_2$—N($R^{40}$)—$R^{41}$, halogen, lower alkyl, fluoro substituted lower alkyl, and cycloalkylamino;

$R^{33}$ is selected from the group consisting of hydrogen, —CN, —NO$_2$, —C(O)—OH, —S(O)—NH$_2$, —S(O)$_2$—NH$_2$, —C(O)—NH$_2$, —O—R$^{43}$, —S—R$^{43}$, —N(R$^{47}$)—C(O)—R$^{43}$, —N(R$^{47}$)—S(O)—R$^{43}$, —N(R$^{47}$)—S(O)$_2$—R$^{43}$, —C(O)—N(R$^{47}$)—R$^{43}$, —C(O)—O—R$^{43}$, —C(O)—R$^{43}$, —S(O)—N(R$^{47}$)—R$^{43}$, —S(O)$_2$—N(R$^{47}$)—R$^{43}$, —S(O)—R$^{43}$, —S(O)$_2$—R$^{43}$, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{33}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—R$^{48}$, —S—R$^{48}$, —N(R$^{47}$)—R$^{48}$, —N(R$^{47}$)—C(O)—R$^{48}$, —N(R$^{47}$)—S(O)—R$^{48}$, —N(R$^{47}$)—S(O)$_2$—R$^{48}$, —C(O)—R$^{48}$, —S(O)—R$^{48}$, —S(O)$_2$—R$^{48}$, —C(O)—O—R$^{48}$, —C(O)—N(R$^{47}$)—R$^{48}$, —S(O)—N(R$^{47}$)—R$^{48}$, —S(O)$_2$—N(R$^{47}$)—R$^{48}$, halogen, lower alkyl, fluoro substituted lower alkyl, and cycloalkylamino:

$R^{34}$ is selected from the group consisting of hydrogen, —OH, —NH$_2$, —CN, —NO$_2$, —C(O)—OH, —S(O)—NH$_2$, —S(O)$_2$—NH$_2$, —C(O)—NH$_2$, —O—R$^{49}$, —S—R$^{49}$, —N(R$^{50}$)—R$^{49}$, —N(R$^{50}$)—C(O)—R$^{49}$, —N(R$^{50}$)—S(O)—R$^{49}$, —N(R$^{50}$)—S(O)$_2$—R$^{49}$, —C(O)—N(R$^{50}$)—R$^{49}$, —C(O)—O—R$^{49}$, —C(O)—R$^{49}$, —S(O)—N(R$^{50}$)—R$^{49}$, —S(O)$_2$—N(R$^{50}$)—R$^{49}$, —S(O)—R$^{49}$, —S(O)$_2$—R$^{49}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkyl amino, di-alkyl amino, cycloalkyl, heterocycloalkyl, aryl, and heteroaryl, wherein cycloalkyl, heterocycloalkyl, aryl, and heteroaryl as $R^{34}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—R$^{51}$, —S—R$^{51}$, —N(R$^{50}$)—R$^{51}$, —N(R$^{50}$)—C(O)—R$^{51}$, —N(R$^{50}$)—S(O)—R$^{51}$, —N(R$^{50}$)—S(O)$_2$—R$^{51}$, —C(O)—R$^{51}$, —S(O)—R$^{51}$, —S(O)$_2$—R$^{51}$, —C(O)—O—R$^{51}$, —C(O)—N(R$^{50}$)—R$^{51}$, —S(O)—N(R$^{50}$)—R$^{51}$, —S(O)$_2$—N(R$^{50}$)—R$^{51}$, halogen, lower alkyl, fluoro substituted lower alkyl, and cycloalkylamino;

$R^{35}$ and $R^{36}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamido, di-alkylamino, and cycloalkylamino; or $R^{35}$ and $R^{36}$ combine to form a 3-7 membered monocyclic cycloalkyl or 5-7 membered monocyclic heterocycloalkyl, wherein the 3-7 membered monocyclic cycloalkyl or 5-7 membered monocyclic heterocycloalkyl is optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^{39}$, $R^{43}$, and $R^{49}$ are independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{39}$, $R^{43}$, or $R^{49}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—R$^{52}$, —S—R$^{52}$, —N(R$^{53}$)—R$^{52}$, —N(R$^{53}$)—C(O)—R$^{52}$, —N(R$^{53}$)—S(O)—R$^{52}$, —N(R$^{53}$)—S(O)$_2$—R$^{52}$, —C(O)—R$^{52}$, —S(O)—R$^{52}$, —S(O)$_2$—R$^{52}$, —C(O)—O—R$^{52}$, —C(O)—N(R$^{53}$)—R$^{52}$, —S(O)—N(R$^{53}$)—R$^{52}$, —S(O)$_2$—N(R$^{53}$)—R$^{52}$, halogen, lower alkyl, fluoro substituted lower alkyl, and cycloalkylamino;

$R^{37}$, $R^{38}$, $R^{40}$, $R^{47}$, $R^{50}$, and $R^{53}$, at each occurrence, are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro Substituted lower alkylthio, mono-alkylamino, fluoro substituted mono-alkylamino, di-alkylamino, fluoro substituted di-alkylamino, and cycloalkylamino; and $R^{41}$, $R^{48}$, $R^{51}$, and $R^{52}$ are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy;

$R^{42}$, $R^{44}$, $R^{45}$, and $R^{46}$ are independently selected from the group consisting of hydrogen, halogen, optionally substituted lower alkyl, —N(R$^{54}$)—R$^{55}$, —O—R$^{54}$, and —S—R$^{56}$;

$R^{54}$ and $R^{55}$ at each occurrence are independently hydrogen or optionally substituted lower alkyl; and $R^{56}$ at each occurrence is optionally substituted lower alkyl.

In a third aspect, compounds of Formula I having the structure according to the following Formula Ib are provided:

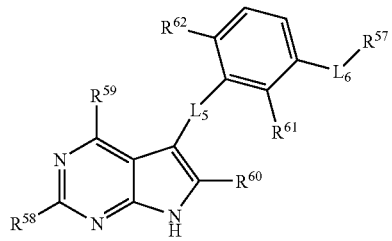

Formula Ib or a salt, a prodrug, a tautomer or a stereoisomer thereof, wherein:

$L_5$ is selected from the group consisting of —C(R$^{35}$R$^{36}$)—, —C(O)—, —C(S)—, —N(R$^{37}$)—, —O—, —S—, —S(O)—, and —S(O)$_2$—;

$L_6$ is selected from the group consisting of —N(R$^{38}$)—C(O)—, —N(R$^{38}$)—C(S)—, —N(R$^{38}$)—S(O)—, —N(R$^{38}$)—S(O)$_2$—, —N(R$^{38}$)—C(O)—N(R$^{38}$)—, —N(R$^{38}$)—C(S)—N(R$^{38}$)—, and —N(R$^{38}$)—S(O)$_2$—N(R$^{38}$)—;

$R^{57}$ is selected from the group consisting of optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

$R^{58}$ is selected from the group consisting of hydrogen, —OH, —NH$_2$, —CN, —NO$_2$, —C(O)—OH, —S(O)—NH$_2$, —S(O)$_2$—NH$_2$, —C(O)—NH$_2$, —O—R$^{39}$, —S—R$^{39}$, —N(R$^{40}$)—R$^{39}$, —N(R$^{40}$)—C(O)—R$^{39}$, —N(R$^{40}$)—S(O)—R$^{39}$, —N(R$^{40}$)—S(O)$_2$—R$^{39}$, —C(O)—N(R$^{40}$)—R$^{39}$, —C(O)—O—R$^{39}$, —C(O)—R$^{39}$, —S(O)—N(R$^{40}$)—R$^{39}$, —S(O)$_2$—N(R$^{40}$)—R$^{39}$, —S(O)—R$^{39}$, —S(O)$_2$—R$^{39}$, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R$^{58}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—R$^{41}$, —S—R$^{41}$, —N(R$^{40}$)—R$^{41}$, —N(R$^{40}$)—C(O)—R$^{41}$, —N(R$^{40}$)—S(O)—R$^{41}$, —N(R$^{40}$)—S(O)$_2$—R$^{41}$, —C(O)—R$^{41}$, —S(O)—R$^{41}$, —S(O)$_2$—R$^{41}$, —C(O)—O—R$^{41}$, —C(O)—N(R$^{40}$)—R$^{41}$, —S(O)—N(R$^{40}$)—R$^{41}$, —S(O)$_2$—N(R$^{40}$)—R$^{41}$, halogen, lower alkyl, fluoro substituted lower alkyl, and cycloalkylamino;

$R^{59}$ is selected from the group consisting of hydrogen, —CN, —NO$_2$, —C(O)—OH, —S(O)—NH$_2$, —S(O)$_2$—NH$_2$, —C(O)—NH$_2$, —O—R$^{43}$, —S—R$^{43}$, —N(R$^{47}$)—C(O)—R$^{43}$, —N(R$^{47}$)—S(O)—R$^{43}$, —N(R$^{47}$)—S(O)$_2$—R$^{43}$, —C(O)—N(R$^{47}$)—R$^{43}$, —C(O)—O—R$^{43}$, —C(O)—R$^{43}$, —S(O)—N(R$^{47}$)—R$^{43}$, —S(O)$_2$—N(R$^{47}$)—R$^{43}$, —S(O)—R$^{43}$, —S(O)$_2$—R$^{43}$, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R$^{59}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—R$^{48}$, —S—R$^{48}$, —N(R$^{47}$)—R$^{48}$, —N(R$^{47}$)—C(O)—R$^{48}$, —N(R$^{47}$)—S(O)—R$^{48}$, —N(R$^{47}$)—S(O)$_2$—R$^{48}$, —C(O)—R$^{48}$, —S(O)—R$^{48}$, —S(O)$_2$—R$^{48}$, —C(O)—O—R$^{48}$, —C(O)—N(R$^{47}$)—R$^{48}$, —S(O)—N(R$^{47}$)—R$^{48}$, —S(O)$_2$—N(R$^{47}$)—R$^{48}$, halogen, lower alkyl, fluoro substituted lower alkyl, and cycloalkylamino;

$R^{60}$ is selected from the group consisting of hydrogen, —OH, —NH$_2$, —CN, —NO$_2$, —C(O)—OH, —S(O)—NH$_2$, —S(O)$_2$—NH$_2$, —C(O)—NH$_2$, —O—R$^{49}$, —S—R$^{49}$, —N(R$^{50}$)—R$^{49}$, —N(R$^{50}$)—C(O)—R$^{49}$, —N(R$^{50}$)—S(O)—R$^{49}$, —N(R$^{50}$)—S(O)$_2$—R$^{49}$, —C(O)—N(R$^{50}$)—R$^{49}$, —C(O)—O—R$^{49}$, —C(O)—R$^{49}$, —S(O)—N(R$^{50}$)—R$^{49}$, —S(O)$_2$—N(R$^{50}$)—R$^{49}$, —S(O)—R$^{49}$, —S(O)$_2$—R$^{49}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R$^{60}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—R$^{51}$, —S—R$^{51}$, —N(R$^{50}$)—R$^{51}$, —N(R$^{50}$)—C(O)—R$^{51}$, —N(R$^{50}$)—S(O)—R$^{51}$, —N(R$^{50}$)—S(O)$_2$—R$^{51}$, —C(O)—R$^{51}$, —S(O)—R$^{51}$, —S(O)$_2$—R$^{51}$, —C(O)—O—R$^{51}$, —C(O)—N(R$^{50}$)—R$^{51}$, —S(O)—N(R$^{50}$)—R$^{51}$, —S(O)$_2$—N(R$^{50}$)—R$^{51}$, halogen, lower alkyl, fluoro substituted lower alkyl, and cycloalkylamino;

$R^{61}$ and $R^{62}$ are independently selected from the group consisting of hydrogen, halogen, $C_{1-3}$ alkyl, and fluoro substituted $C_{1-3}$ alkyl; and $R^{35}$, $R^{36}$, $R^{37}$, $R^{38}$, $R^{39}$, $R^{40}$, $R^{41}$, $R^{43}$, $R^{47}$, $R^{48}$, $R^{49}$, $R^{50}$, and $R^{51}$ are as defined for Formula Ia.

In some embodiments of compounds of Formula I, Formula Ia or Formula Ib, $R^1$, $R^{31}$ and $R^{57}$, respectively, are selected from the group consisting of lower alkyl, lower alkenyl, lower alkynyl, cycloalkyl, heterocycloalkyl, aryl and heteroaryl, wherein lower alkyl, lower alkenyl or lower alkynyl are optionally substituted with one or more substituents $R^{63}$, and wherein cycloalkyl, heterocycloalkyl, aryl or heteroaryl are optionally substituted with one or more substituents $R^{64}$, wherein $R^{63}$ at each occurrence is independently selected from the group consisting of —OH, —NH$_2$, —C(O)—OH, —S(O)—NH$_2$, —S(O)$_2$—NH$_2$, —C(O)—NH$_2$, —O—R$^{65}$, —S—R$^{65}$, —N(R$^{66}$)—R$^{65}$, —N(R$^{66}$)—C(O)—R$^{65}$, —N(R$^{66}$)—S(O)—R$^{65}$, —N(R$^{66}$)—S(O)$_2$—R$^{65}$, —C(O)—N(R$^{66}$)—R$^{65}$, —C(O)—O—R$^{65}$, —C(O)—R$^{65}$, —S(O)—N(R$^{66}$)—R$^{65}$, —S(O)$_2$—N(R$^{66}$)—R$^{65}$, —S(O)—R$^{65}$, —S(O)$_2$—R$^{65}$, fluoro, cycloalkyl, heterocycloalkyl, aryl and heteroaryl, wherein cycloalkyl, heterocycloalkyl, aryl and heteroaryl are optionally substituted with one or more substituents $R^{64}$;

$R^{64}$ at each occurrence is independently selected from the group consisting of —OH, —NH$_2$, —NO$_2$, —CN, —C(O)—OH, —S(O)—NH$_2$, —S(O)$_2$—NH$_2$, —C(O)—NH$_2$, —O—R$^{65}$, —S—R$^{65}$, —N(R$^{66}$)—R$^{65}$, —N(R$^{66}$)—C(O)—R$^{65}$, —N(R$^{66}$)—S(O)—R$^{65}$, —N(R$^{66}$)—S(O)$_2$—R$^{65}$, —S(O)—R$^{65}$, —S(O)$_2$—R$^{65}$, —C(O)—R$^{65}$, —C(O)—O—R$^{65}$, —C(O)—N(R$^{66}$)—R$^{65}$, —S(O)—N(R$^{66}$)—R$^{65}$, —S(O)$_2$—N(R$^{66}$)—R$^{65}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as R$^{64}$, or as substituents of lower alkyl, are optionally substituted with one or more substituents selected from the group consisting of —OH, —NH$_2$, —NO$_2$, —CN, —C(O)—OH, —S(O)$_2$—NH$_2$, —C(O)—NH$_2$, —O—R$^{67}$, —S—R$^{67}$, —N(R$^{66}$)—R$^{67}$, —N(R$^{66}$)—C(O)—R$^{67}$, —N(R$^{66}$)—S(O)$_2$—R$^{67}$, —S(O)—R$^{67}$, —S(O)$_2$—R$^{67}$, —C(O)—R$^{67}$, —C(O)—O—R$^{67}$, —(O)—N(R$^{66}$)—R$^{67}$, —S(O)$_2$—N(R$^{66}$)—R$^{67}$, halogen, lower alkyl, fluoro substituted lower alkyl, and cycloalkylamino;

R$^{65}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as R$^{65}$ or as substituents of lower alkyl are optionally substituted with one or more substituents selected from the group consisting of —OH, —NH$_2$, —CN, —NO$_2$, —C(O)—OH, —S(O)$_2$—NH$_2$, —C(O)—NH$_2$, —O—R$^{69}$, —S—R$^{69}$, —N(R$^{68}$)—R$^{69}$, —N(R$^{68}$)—C(O)—R$^{69}$, —N(R$^{68}$)—S(O)$_2$—R$^{69}$, —C(O)—R$^{69}$, —S(O)—R$^{69}$, —S(O)$_2$—R$^{69}$, —C(O)—O—R$^{69}$, —C(O)—N(R$^{68}$)—R$^{69}$, —S(O)$_2$—N(R$^{68}$)—R$^{69}$, halogen, lower alkyl, fluoro substituted lower alkyl, and cycloalkylamino;

R$^{66}$ and R$^{68}$ at each occurrence are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino; and R$^{67}$ and R$^{69}$ at each occurrence are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

In some embodiments of compounds of Formula I, Formula Ia or Formula Ib, R$^1$, R$^{31}$ and R$^{57}$, respectively, are selected from the group consisting of lower alkyl, cycloalkyl, heterocycloalkyl, aryl and heteroaryl, wherein lower alkyl, is optionally substituted with one or more substituents R$^{63}$, and wherein cycloalkyl, heterocycloalkyl, aryl or heteroaryl are optionally substituted with one or more substituents R$^{64}$; wherein R$^{63}$ at each occurrence is independently selected from the group consisting of —OH, —NH$_2$, —O—R$^{65}$, —S—R$^{65}$, —N(R$^{66}$)—R$^{65}$, —N(R$^{66}$)—C(O)—R$^{65}$, —N(R$^{66}$)—S(O)—R$^{65}$, —N(R$^{66}$)—S(O)$_2$—R$^{65}$, —C(O)—R$^{65}$, —S(O)—R$^{65}$, —S(O)$_2$—R$^{65}$, fluoro, cycloalkyl, heterocycloalkyl, aryl and heteroaryl, wherein cycloalkyl, heterocycloalkyl, aryl and heteroaryl are optionally substituted with one or more substituents R$^{64}$; R$^{64}$ at each occurrence is independently selected from the group consisting of —OH, —NH$_2$, —NO$_2$, —CN, —O—R$^{65}$, —S—R$^{65}$, —N(R$^{66}$)—R$^{65}$, —N(R$^{66}$)—C(O)—R$^{65}$, —N(R$^{66}$)—S(O)—R$^{65}$, —N(R$^{66}$)—S(O)$_2$—R$^{65}$, —C(O)—R$^{65}$, —S(O)—R$^{65}$, —S(O)$_2$—R$^{65}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as R$^{64}$, or as substituents of lower alkyl, are optionally substituted with one or more substituents selected from the group consisting of —OH, —NH$_2$, —NO$_2$, —CN, —O—R$^{67}$, —S—R$^{67}$, —N(R$^{66}$)—R$^{67}$, —N(R$^{66}$)—C(O)—R$^{67}$, —N(R$^{66}$)—S(O)$_2$—R$^{67}$, —S(O)—R$^{67}$, —S(O)$_2$—R$^{67}$, —C(O)—R$^{67}$, halogen, lower alkyl, fluoro substituted lower alkyl, and cycloalkylamino; and wherein R$^{65}$, R$^{66}$, and R$^{67}$ are as defined in paragraph [0006].

In some embodiments of compounds of Formula I, Formula Ia, and Formula Ib, further to any of the above embodiments of compounds of Formula I, Formula Ia, and Formula Ib:

R$^2$, R$^{32}$, and R$^{58}$, respectively, are selected from the group consisting of hydrogen, —CN, —O—R$^{70}$, —S—R$^{70}$, —N(R$^{71}$)—R$^{70}$, and lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino;

R$^3$, R$^{33}$, and R$^{59}$, respectively, are selected from the group consisting of hydrogen, —CN, —O—R$^{70}$, —S—R$^{70}$, and lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino;

R$^4$, R$^{34}$, and R$^{60}$, respectively, are hydrogen;

R$^{70}$ is lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino; and R$^{71}$ is hydrogen or lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In a fourth aspect, compounds of Formula I having the structure according to the following Formula Ic are provided:

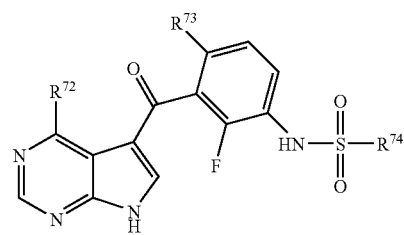

Formula Ic or a salt, a prodrug, a tautomer or a stereoisomer thereof, wherein:

R$^{72}$ is hydrogen, lower alkyl, fluoro substituted lower alkyl, lower alkoxy, fluoro substituted lower alkoxy, or cycloalkyl;

$R^{73}$ is hydrogen or fluoro;

$R^{74}$ is lower alkyl, fluoro substituted lower alkyl, cycloalkyl, di-alkylamino, cycloalkylamino, pyridinyl, thiazolyl, triazolyl, or phenyl, wherein phenyl is optionally substituted with 1 or 2 substituents independently selected from the group consisting of fluoro, lower alkyl, fluoro substituted lower alkyl, lower alkoxy, and fluoro substituted lower alkoxy.

In one embodiment of compounds of Formula Ic, $R^{72}$ is hydrogen, lower alkyl, lower alkoxy, or cycloalkyl; $R^{73}$ is hydrogen or fluoro; $R^{74}$ is lower alkyl, fluoro substituted lower alkyl, cycloalkyl, di-alkylamino, cycloalkylamino, or phenyl, wherein phenyl is optionally substituted with 1 or 2 substituents independently selected from the group consisting of fluoro, lower alkyl, trifluoromethyl, methoxy and difluoromethoxy.

In reference to compounds herein, unless clearly indicated to the contrary, specification of a compound or group of compounds includes salts of such compound(s) (including pharmaceutically acceptable salts), formulations of such compound(s) (including pharmaceutically acceptable formulations), conjugates thereof, derivatives thereof, forms thereof, prodrugs thereof, and all stereoisomers thereof. In reference to compositions, kits, methods of use, etc. of compounds of Formula I described herein, it is understood (unless indicated otherwise) that a compound of Formula I includes all sub-embodiments thereof (e.g. including Formulae Ia-Ic, and all embodiments as described above).

In one embodiment of compounds of Formula I, the compound is selected from the group consisting of:

Propane-1-sulfonic acid {2,4-difluoro-3-[hydroxy-(7H-pyrrolo[2,3-d]pyrimidin-5-yl)-methyl]-phenyl}-amide (P-0001),
Propane-1-sulfonic acid [2,4-difluoro-3-(7H-pyrrolo[2,3-d]pyrimidine-5-carbonyl)-phenyl]-amide (P-0002),
N-2,4-difluoro-3-[hydroxy-(7H-pyrrolo[2,3-d]pyrimidin-5-yl)-methyl]-phenyl-4-trifluoromethyl-benzenesulfonamide (P-0003),
N-[2,4-Difluoro-3-(7H-pyrrolo[2,3-d]pyrimidine-5-carbonyl)-phenyl]-4-trifluoromethyl-benzenesulfonamide (P-0004),
Propane-1-sulfonic acid {2-fluoro-3-[hydroxy-(7H-pyrrolo[2,3-d]pyrimidin-5-yl)-methyl]-phenyl}-amide (P-0005),
Propane-1-sulfonic acid [2-fluoro-3-(7H-pyrrolo[2,3-d]pyrimidine-5-carbonyl)-phenyl]-amide (P-0006),
N-[2,4-Difluoro-3-(7H-pyrrolo[2,3-d]pyrimidine-5-carbonyl)-phenyl]-methanesulfonamide (P-0007),
Ethanesulfonic acid [2,4-difluoro-3-(7H-pyrrolo[2,3-d]pyrimidine-5-carbonyl)-phenyl]-amide (P-0008),
Propane-2-sulfonic acid [2,4-difluoro-3-(7H-pyrrolo[2,3-d]pyrimidine-5-carbonyl)-phenyl]-amide (P-0009),
Butane-2-sulfonic acid [2,4-difluoro-3-(7H-pyrrolo[2,3-d]pyrimidine-5-carbonyl)-phenyl]-amide (P-0010),
2-Methyl-propane-1-sulfonic acid [2,4-difluoro-3-(7H-pyrrolo[2,3-d]pyrimidine-5-carbonyl)-phenyl]-amide (P-0011),
Pentane-2-sulfonic acid [2,4-difluoro-3-(7H-pyrrolo[2,3-d]pyrimidine-5-carbonyl)-phenyl]-amide (P-0012),
Cyclopentanesulfonic acid [2,4-difluoro-3-(7H-pyrrolo[2,3-d]pyrimidine-5-carbonyl)-phenyl]-amide (P-0013),
Cyclohexanesulfonic acid [2,4-difluoro-3-(7H-pyrrolo[2,3-d]pyrimidine-5-carbonyl)-phenyl]-amide (P-0014),
N-[2,4-Difluoro-3-(7H-pyrrolo[2,3-d]pyrimidine-5-carbonyl)-phenyl]-C,C,C-trifluoro-methanesulfonamide (P-0015),
2,2,2-Trifluoro-ethanesulfonic acid [2,4-difluoro-3-(7H-pyrrolo[2,3-d]pyrimidine-5-carbonyl)-phenyl]-amide (P-0016),
3,3,3-Trifluoro-propane-1-sulfonic acid [2,4-difluoro-3-(7H-pyrrolo[2,3-d]pyrimidine-5-carbonyl)-phenyl]-amide (P-0017),
Dimethylamine-1-sulfonic acid [3-(7H-pyrrolo[2,3-d]pyrimidine-5-carbonyl)-2,4-difluoro-phenyl]-amide (P-0018),
Diethylamine-1-sulfonic acid [3-(7H-pyrrolo[2,3-d]pyrimidine-5-carbonyl)-2,4-difluoro-phenyl]-amide (P-0019),
Pyrrolidine-1-sulfonic acid [2,4-difluoro-3-(7H-pyrrolo[2,3-d]pyrimidine-5-carbonyl)-phenyl]-amide (P-0020),
Morpholine-4-sulfonic acid [2,4-difluoro-3-(7H-pyrrolo[2,3-d]pyrimidine-5-carbonyl)-phenyl]-amide (P-0021),
2H-[1,2,4]Triazole-3-sulfonic acid [2,4-difluoro-3-(7H-pyrrolo[2,3-d]pyrimidine-5-carbonyl)-phenyl]-amide (P-0022),
Thiazole-2-sulfonic acid [2,4-difluoro-3-(7H-pyrrolo[2,3-d]pyrimidine-5-carbonyl)-phenyl]-amide (P-0023),
Pyridine-2-sulfonic acid [2,4-difluoro-3-(7H-pyrrolo[2,3-d]pyrimidine-5-carbonyl)-phenyl]-amide (P-0024),
N-[2,4-Difluoro-3-(7H-pyrrolo[2,3-d]pyrimidine-5-carbonyl)-phenyl]-2-fluoro-benzenesulfonamide (P-0025),
N-[2,4-Difluoro-3-(7H-pyrrolo[2,3-d]pyrimidine-5-carbonyl)-phenyl]-3-fluoro-benzenesulfonamide (P-0026),
N-[2,4-Difluoro-3-(7H-pyrrolo[2,3-d]pyrimidine-5-carbonyl)-phenyl]-2,5-difluoro-benzenesulfonamide (P-0027),
N-[2,4-Difluoro-3-(7H-pyrrolo[2,3-d]pyrimidine-5-carbonyl)-phenyl]-benzenesulfonamide (P-0028),
N-[2,4-Difluoro-3-(7H-pyrrolo[2,3-d]pyrimidine-5-carbonyl)-phenyl]-4-isopropyl-benzenesulfonamide (P-0029),
N-[2,4-Difluoro-3-(7H-pyrrolo[2,3-d]pyrimidine-5-carbonyl)-phenyl]-4-propyl-benzenesulfonamide (P-0030),
3-Difluoromethoxy-N-[2,4-difluoro-3-(7H-pyrrolo[2,3-d]pyrimidine-5-carbonyl)-phenyl]-benzenesulfonamide (P-0031),
4-Difluoromethoxy-N-[2,4-difluoro-3-(7H-pyrrolo[2,3-d]pyrimidine-5-carbonyl)-phenyl]-benzenesulfonamide (P-0032),
4-tert-Butyl-N-[2,4-difluoro-3-(7H-pyrrolo[2,3-d]pyrimidine-5-carbonyl)-phenyl]-benzenesulfonamide (P-0033),
N-{2-Fluoro-3-[hydroxy-(7H-pyrrolo[2,3-d]pyrimidin-5-yl)-methyl]-phenyl}-4-trifluoromethyl-benzenesulfonamide P-0034),
N-[2-Fluoro-3-(7H-pyrrolo[2,3-d]pyrimidine-5-carbonyl)-phenyl]-4-trifluoromethyl-benzenesulfonamide (P-0035),
Ethanesulfonic acid [2-fluoro-3-(7H-pyrrolo[2,3-d]pyrimidine-5-carbonyl)-phenyl]-amide (P-0036
4-Fluoro-N-[2-fluoro-3-(7H-pyrrolo[2,3-d]pyrimidine-5-carbonyl)-phenyl]-benzenesulfonamide (P-0037),
2,2,2-Trifluoro-ethanesulfonic acid [2-fluoro-3-(7H-pyrrolo[2,3-d]pyrimidine-5-carbonyl)-phenyl]-amide (P-0038),
Pyridine-3-sulfonic acid [2-fluoro-3-(7H-pyrrolo[2,3-d]pyrimidine-5-carbonyl)-phenyl]-amide (P-0039),
2,5-Difluoro-N-[2-fluoro-3-(7H-pyrrolo[2,3-d]pyrimidine-5-carbonyl)-phenyl]-benzenesulfonamide (P-0040),
2,6-Difluoro-N-[2-fluoro-3-(7H-pyrrolo[2,3-d]pyrimidine-5-carbonyl)-phenyl]-benzenesulfonamide (P-0041),
2,4-Difluoro-N-[2-fluoro-3-(7H-pyrrolo[2,3-d]pyrimidine-5-carbonyl)-phenyl]-benzenesulfonamide (P-0042),
Propane-2-sulfonic acid [2-fluoro-3-(7H-pyrrolo[2,3-d]pyrimidine-5-carbonyl)-phenyl]-amide (P-0043),
3-Fluoro-N-[2-fluoro-3-(7H-pyrrolo[2,3-d]pyrimidine-5-carbonyl)-phenyl]-benzenesulfonamide (P-0044),
N,N-Dimethylamino-sulfonic acid [2-fluoro-3-(7H-pyrrolo[2,3-d]pyrimidine-5-carbonyl)-phenyl]-amide (P-0045), Pyrrolidine-1-sulfonic acid [2-fluoro-3-(7H-pyrrolo[2,3-d]pyrimidine-5-carbonyl)-phenyl]-amide (P-0046),
2-Methyl-propane-1-sulfonic acid [2-fluoro-3-(7H-pyrrolo[2,3-d]pyrimidine-5-carbonyl)-phenyl]-amide (P-0047),
Butane-2-sulfonic acid [2-fluoro-3-(7H-pyrrolo[2,3-d]pyrimidine-5-carbonyl)-phenyl]-amide (P-0048),
Cyclobutanesulfonic acid [2-fluoro-3-(7H-pyrrolo[2,3-d]pyrimidine-5-carbonyl)-phenyl]-amide (P-0049),
Morpholine-4-sulfonic acid [2-fluoro-3-(7H-pyrrolo[2,3-d]pyrimidine-5-carbonyl)-phenyl]-amide (P-0050),
2-Fluoro-N-[2-fluoro-3-(7H-pyrrolo[2,3-d]pyrimidine-5-carbonyl)-phenyl]-benzenesulfonamide (P-0051),
Cyclohexanesulfonic acid [2-fluoro-3-(7H-pyrrolo[2,3-d]pyrimidine-5-carbonyl)-phenyl]-amide (P-0052),
Cyclopentanesulfonic acid [2-fluoro-3-(7H-pyrrolo[2,3-d]pyrimidine-5-carbonyl)-phenyl]-amide (P-0053),
Pentane-2-sulfonic acid [2-fluoro-3-(7H-pyrrolo[2,3-d]pyrimidine-5-carbonyl)-phenyl]-amide (P-0054),
Propane-1-sulfonic acid {2,4-difluoro-3-[hydroxy-(4-methyl-7H-pyrrolo[2,3-d]pyrimidin-5-yl)-methyl]-phenyl}-amide (P-0055),
Propane-1-sulfonic acid [2,4-difluoro-3-(4-methyl-7H-pyrrolo[2,3-d]pyrimidine-5-carbonyl)-phenyl]-amide (P-0056),
Propane-1-sulfonic acid {2,4-difluoro-3-[hydroxy-(4-methoxy-7H-pyrrolo[2,3-d]pyrimidin-5-yl)-methyl]-phenyl}-amide (P-0057),
Propane-1-sulfonic acid [2,4-difluoro-3-(4-methoxy-7H-pyrrolo[2,3-d]pyrimidine-5-carbonyl)-phenyl]-amide (P-0058),
N-[2-Fluoro-3-(4-methoxy-7H-pyrrolo[2,3-d]pyrimidine-5-carbonyl)-phenyl]-4-trifluoromethyl-benzenesulfonamide (P-0059),
Propane-1-sulfonic acid [2-fluoro-3-(4-methoxy-7H-pyrrolo[2,3-d]pyrimidine-5-carbonyl)-phenyl]-amide (P-0060),
N-[2,4-Difluoro-3-(4-methoxy-7H-pyrrolo[2,3-d]pyrimidine-5-carbonyl)-phenyl]-4-trifluoromethyl-benzenesulfonamide (P-0061),
N-[2,4-Difluoro-3-(7H-pyrrolo[2,3-d]pyrimidine-5-carbonyl)-phenyl]-4-fluoro-benzenesulfonamide (P-0062),
Cyclobutanesulfonic acid [2,4-difluoro-3-(7H-pyrrolo[2,3-d]pyrimidine-5-carbonyl)-phenyl]-amide (P-0063),
N-[2,4-Difluoro-3-(7H-pyrrolo[2,3-d]pyrimidine-5-carbonyl)-phenyl]-2,4-difluoro-benzenesulfonamide (P-0064),
N-[2,4-Difluoro-3-(7H-pyrrolo[2,3-d]pyrimidine-5-carbonyl)-phenyl]-2,6-difluoro-benzenesulfonamide (P-0065),
Pyridine-3-sulfonic acid [2,4-difluoro-3-(7H-pyrrolo[2,3-d]pyrimidine-5-carbonyl)-phenyl]-amide (P-0066),
N-{3-[(4-Cyclopropyl-7H-pyrrolo[2,3-d]pyrimidin-5-yl)-hydroxy-methyl]-2,4-difluoro-phenyl}-4-trifluoromethyl-benzenesulfonamide (P-0067),
N-[3-(4-Cyclopropyl-7H-pyrrolo[2,3-d]pyrimidine-5-carbonyl)-2,4-difluoro-phenyl]-4-trifluoromethyl-benzenesulfonamide (P-0068),
Propane-1-sulfonic acid [3-(4-cyclopropyl-7H-pyrrolo[2,3-d]pyrimidine-5-carbonyl)-2,4-difluoro-phenyl]-amide (P-0069), and
any salt, prodrug, tautomer, or stereoisomer thereof.

In a fifth aspect, methods are provided for treating a protein kinase mediated disease or condition in an animal subject in need thereof, wherein the method involves administering to the subject an effective amount of any one or more compound(s) of Formula I. The terms "treat," "therapy," and like terms refer to the administration of material, e.g., any one or more compound(s) of Formula I in an amount effective to prevent, alleviate, or ameliorate one or more symptoms of a disease or condition, i.e., indication, and/or to prolong the survival of the subject being treated. The term "protein kinase mediated disease or condition" refers to a disease or condition in which the biological function of a protein kinase affects the development, course, and/or symptoms of the disease or condition, and/or in which modulation of the protein kinase alters the development, course, and/or symptoms of the disease or condition. A protein kinase mediated disease or condition includes a disease or condition for which modulation provides a therapeutic benefit, e.g. wherein treatment with protein kinase inhibitors, including compounds described herein, provides a therapeutic benefit to the subject suffering from or at risk of the disease or condition. In certain embodiments, the method involves administering to the subject an effective amount of a compound of Formula I in combination with one or more other therapies for the disease or condition.

In a sixth aspect, the invention provides methods for treating a Raf protein kinase mediated disease or condition in an animal subject in need thereof, wherein the method involves administering to the subject an effective amount of any one or more compound(s) of Formula I. The terms "Raf protein kinase mediated disease or condition," "Raf kinase mediated disease or condition," "Raf mediated disease or condition," and the like refer to a disease or condition in which the biological function of a Raf protein kinase, including any mutations thereof, affects the development, course, and/or symptoms of the disease or condition, and/or in which modulation of the Raf protein kinase alters the development, course, and/or symptoms of the disease or condition. The Raf protein kinase includes, but is not limited to, A-Raf, A-Raf mutations, B-Raf, mutations of B-Raf, c-Raf-1 and mutations of c-Raf-1. In some embodiments, the Raf protein kinase is B-Raf mutation V600E. In some embodiments, the Raf protein kinase is B-Raf mutation V600E/T529I. In some embodiments, the disease or condition is a cancer that is amenable to treatment by an inhibitor of the V600E mutant B-Raf. In some embodiments, the disease or condition is a cancer that is amenable to treatment by an inhibitor of the V600E/T529I mutant B-Raf. The Raf protein kinase mediated disease or condition includes a disease or condition for which Raf inhibition provides a therapeutic benefit, e.g. wherein treatment with Raf inhibitors, including compounds described herein, provides a therapeutic benefit to the subject suffering from or at risk of the disease or condition. In one embodiment, the method involves administering to the subject an effective amount of a compound of Formula I in combination with one or more other therapies for the disease or condition. Similarly, the terms "A-Raf, B-Raf or c-Raf-1 protein kinase mediated disease or condition," "A-Raf, B-Raf or c-Raf-1 kinase mediated disease or condition," "A-Raf, B-Raf or c-Raf-1 mediated disease or condition," and the like refer to a disease or condition in which the biological function of an A-Raf, B-Raf or c-Raf-1 kinase, respectively, including any mutations thereof, affects the development, course and/or symptoms of the disease or condition, and/or in which modulation of the A-Raf, B-Raf or c-Raf-1 protein kinase, respectively, alters the development, course, and/or symptoms of the disease or condition.

In a seventh aspect, a compound of Formula I will have an $IC_{50}$ of less than 500 nm, less than 100 nM, less than 50 nM, less than 20 nM, less than 10 nM, less than 5 nM, or less than 1 nM as determined in a generally accepted kinase activity assay. In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Hcr4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, including any mutations thereof.

In an eighth aspect, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kit, Lck, Lyn, MAP2K1, MAP2K2, MAP4K4, MAPKAPK2, Met, Mnk1, MLK1, mTOR, p38, PDPK1, PI3Kα, PI3Kβ, PI3Kδ, PI3Kγ, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70, including any mutations thereof.

In a ninth aspect, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, Lck, Lyn, MAP2K1, MAP4K4, MAPKAPK2, Met, mTOR, p38, PDGFRB, PI3Kα, PI3Kβ, PI3Kδ, PI3Kγ, Pim1, PKC theta, Pyk2, Ret, Src, Stk6, TrkA, TrkB, Yes, and Zap70, including any mutations thereof.

In a tenth aspect, a compound of Formula I will have an $IC_{50}$ of less than 500 nm, less than 100 nM, less than 50 nM, less than 20 nM, less than 10 n4, less than 5 nM, or less than 1 nM with respect to at least one kinase selected from the group consisting of Ab1, A-Raf, B-Raf, Btk, c-Raf-1, EGFR, EphB2, Erk2, Fak, Fms, Irak4, Jnk1, Jnk2, Jnk3, Kit, Lck, Lyn, MAP2K1, MAP4K4, MAPKAPK2, Met, mTOR, p38, PI3Kα, PI3Kβ, PI3Kδ, PI3Kγ, Pim1, PKC theta, Pyk2, Src, Stk6, TrkA, TrkB, Yes, and Zap70, including any mutations thereof.

In an eleventh aspect, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of A-Raf, B-Raf, B-Raf V600E mutant, B-Raf V600E/T529I mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret, including any mutations thereof.

In a twelfth aspect, a compound of Formula I is an inhibitor of a Raf kinase and has an $IC_{50}$ of less than 500 nm, less than 100 nM, less than 50 nM, less than 20 nM, less than 10 nM, less than 5 nM, or less than 1 nM as determined in a generally accepted Raf kinase activity assay. In some embodiments, a compound of Formula I will have an $IC_{50}$ of less than 500 nm, less than 100 nM, less than 50 nM, less than 20 nM, less than 10 nM, less than 5 nM, or less than 1 nM with respect to B-Raf, c-Raf-1, B-Raf V600E mutant, or B-Raf V600E/T529I mutant. In some embodiments, a compound of Formula I will selectively inhibit one Raf kinase relative to one or more other Raf kinases. In some embodiments, the compound of Formula I will selectively inhibit a mutation of the Raf kinase relative to the wild type kinase, for example B-Raf V600E mutant relative to wild type B-Raf.

Further to any of the above mentioned aspects and embodiments, a compound of Formula I will also inhibit the effects of a mutation of the kinase, including, but not limited to, a mutation that is related to a disease state, such as a cancer. For example, B-Raf V600E mutant is present in a high percentage of some cancers, such as melanoma, and compounds will inhibit the kinase activity of this mutant.

Further to any of the above mentioned aspects and embodiments, a compound of Formula I may selectively inhibit one kinase relative to one or more other kinases, where preferably inhibition is selective with respect to any of the other kinases, whether a kinase discussed herein, or other kinases. In some embodiments, the compound may selectively inhibit the effects of a mutation of the kinase relative to the wild type kinase, for example B-Raf V600E mutant relative to wild type B-Raf. Selective inhibition of one kinase relative to another is such that the $IC_{50}$ for the one kinase may be at least about 2-fold, also 5-fold, also 10-fold, also 20-fold, also 50-fold, or at least about 100-fold less than the $ID_{50}$ for any of the other kinases as determined in a generally accepted kinase activity assay.

In a thirteenth aspect, compositions are provided that include a therapeutically effective amount of any one or more compound(s) of Formula I and at least one pharmaceutically acceptable carrier, excipient, and/or diluent, including combinations of any two or more compounds of Formula I. The composition can further include a plurality of different pharmacologically active compounds, which can include a plurality of compounds of Formula I. In certain embodiments, the composition can include any one or more compound(s) of Formula I along with one or more compounds that are therapeutically effective for the same disease indication. In one embodiment, the composition includes any one or more compound(s) of Formula I along with one or more compounds that are therapeutically effective for the same disease indication, wherein the compounds have a synergistic effect on the disease indication. In one embodiment, the composition includes any one or more compound(s) of Formula I effective in treating a cancer and one or more other compounds that are effective in treating the same cancer, further wherein the compounds are synergistically effective in treating the cancer.

In a fourteenth aspect, methods are provided for modulating the activity of a protein kinase selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, including any mutations thereof, by contacting the protein kinase with an effective amount of any one or more compound(s) of Formula I.

In a fifteenth aspect, methods are provided for treating a protein kinase mediated disease or condition in an animal subject in need thereof, wherein the method involves administering to the subject an effective amount of a composition including any one or more compound(s) of Formula I.

In a sixteenth aspect, methods are provided for treating a disease or condition mediated by a protein kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, including any mutations thereof, in a subject in need thereof by administering to the subject an effective amount of a composition including any one or more compound(s) of Formula I.

In a seventeenth aspect, the invention provides methods for treating a disease or condition mediated by a protein kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kit, Lck, Lyn, MAP2K1, MAP2K2, MAP4K4, MAPKAPK2, Met, Mnk1, MLK1, mTOR, p38, PDPK1, PI3Kα, PI3Kβ, PI3Kδ, PI3Kγ, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70, including any mutations thereof, in a subject in need thereof by administering to the subject an effective amount of a composition including any one or more compound(s) of Formula I.

In an eighteenth aspect, the invention provides methods for treating a disease or condition mediated by a protein kinase selected from the group consisting of Ab1, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, Lck, Lyn, MAP2K1, MAP4K4, MAPKAPK2, Met, mTOR, p38, PDGFRB, PI3Kα, PI3Kβ, PI3Kδ, PI3Kγ, Pim1, PKC theta, Pyk2, Ret, Src, Stk6, TrkA, TrkB, Yes, and Zap70, including any mutations thereof, in a subject in need thereof by administering to the subject an effective amount of a composition including any one or more compound(s) of Formula I.

In a nineteenth aspect, the invention provides methods for treating a disease or condition mediated by a protein kinase selected from the group consisting of Ab1, A-Raf, B-Raf, Btk, c-Raf-1, EGFR, EphB2, Erk2, Fak, Fms, Irak4, Jnk1, Jnk2, Jnk3, Kit, Lck, Lyn, MAP2K1, MAP4K4, MAPKAPK2, Met, mTOR, p38, PI3Kα, PI3Kβ, PI3Kδ, PI3Kγ, Pim1, PKC theta, Pyk2, Src, Stk6, TrkA, TrkB, Yes, and Zap70, including any mutations thereof, in a subject in need thereof by administering to the subject an effective amount of a composition including any one or more compound(s) of Formula I.

In a twentieth aspect, the invention provides methods for treating a disease or condition mediated by a protein kinase selected from the group consisting of A-Raf, B-Raf, B-Raf V600E mutant, B-Raf V600E/T529I mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, Kdr, Src and Ret, including any mutations thereof, in a subject in need thereof by administering to the subject an effective amount of a composition including any one or more compound(s) of Formula I.

In a twenty-first aspect, the invention provides methods for treating a disease or condition mediated by A-Raf, B-Raf, c-Raf-1, B-Raf V600E mutant, or B-Raf V600E/T529I mutant in a subject in need thereof by administering to the subject an effective amount of a composition including any one or more compound(s) of Formula I. In one embodiment, the invention provides methods for treating a disease or condition mediated by A-Raf, B-Raf, c-Raf-1, B-Raf V600E mutant, or B-Raf V600E/T529I mutant by administering to the subject an effective amount of a composition including any one or more compound(s) of Formula I in combination with one or more other suitable therapies for treating the disease. In one embodiment, the invention provides methods for treating a cancer mediated by B-Raf V600E mutant or B-Raf V600E/T529I mutant by administering to the subject an effective amount of a composition including any one or more compound(s) of Formula I in combination with one or more suitable anticancer therapies, such as one or more chemotherapeutic drugs.

In a twenty-second aspect, the invention provides a method of treating a cancer in a subject in need thereof by administering to the subject an effective amount of a composition including any one or more compound(s) of Formula I, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or α particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In a twenty-third aspect, the invention provides a method of treating a cancer in a subject in need thereof by administering to the subject an effective amount of a composition including any one or more compound(s) of Formula I, in combination with one or more suitable chemotherapeutic agents. In one embodiment, the one or more suitable chemotherapeutic agents is selected from an alkylating agent, including, but not limited to, adozelesin, altretainine, bendainustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, anuubicin, bleomycin, dactinomycin, daunorubicin, doxorubicin, elsamitiucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, geincitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amisacrine, belotecan, edotecarin, etoposide, etoposide phosphate, exatecan, ihinotecan (also active metabolite SN-38 (7-ethyl-10-hydroxy-camptothecin)), lucanthione, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifamib). Preferably, the method of treating a cancer involves administering to the subject an effective amount of a composition including any one or more compound(s) of Formula I in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib.

In a twenty-fourth aspect, the invention provides a method of treating or prophylaxis of a disease or condition in a mammal in need thereof, by administering to the mammal a therapeutically effective amount of any one or more compound(s) of Formula I, a prodrug of such compound, a pharmaceutically acceptable salt of such compound or prodrug, or a pharmaceutically acceptable formulation of such compound or prodrug. The compound can be alone or can be part of a composition. In one embodiment, the invention provides a method of treating or prophylaxis of a disease or condition in a mammal, by administering to the mammal a therapeutically effective amount of any one or more compound(s) of Formula I, a prodrug of such compound, a pharmaceutically acceptable salt of such compound or prodrug, or a pharmaceutically acceptable formulation of such compound or prodrug in combination with one or more other suitable therapies for the disease or condition.

In a twenty-fifth aspect, the invention provides kits that include a compound or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the invention kit includes written instructions for use and/or other indication that the compound or composition is suitable or approved for administration to a mammal, e.g., a human, for a protein kinase-mediated disease or condition; and the compound or composition is packaged in unit dose or single dose form, e.g., single dose pills, capsules, or the like.

In aspects and embodiments involving treatment or prophylaxis of a disease or condition with the compounds of Formula I, the invention provides methods for treating an A-Raf-mediated, B-Raf-mediated and/or c-Raf-1-mediated disease or condition in an animal subject in need thereof (e.g. a mammal such as a human, other primates, sports animals, animals of commercial interest such as cattle, farm animals such as horses, or pets such as dogs and cats), e.g., a disease or condition characterized by abnormal A-Raf, B-Raf, and/or c-Raf-1 activity (e.g. kinase activity). In some embodiments, invention methods may involve administering to the subject suffering from or at risk of an A-Rat-mediated, B-Raf-mediated and/or c-Raf-1-mediated disease or condition an effective amount of compound of Formula I. In one embodiment, the A-Raf-mediated, B-Raf-mediated, and/or c-Raf-1-mediated disease is selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, sarcoma, carcinoma (e.g. gastrointestinal, liver, bile duct (cholangiocarcinoma), colorectal, lung, breast, pancreatic, thyroid, renal, ovarian, prostate), lymphoma (e.g. histiocytic lymphoma) neurofibromatosis, acute mycloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeticiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori, Hepatitis* and *Influenza* viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polynyositis, and inclusion body myositis), diseases of the neuromuscularjunction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, sarcoma, gastrointestinal cancer, liver cancer, cholangiocarcinoma, colorectal cancer, lung cancer, breast cancer, pancreatic cancer, thyroid cancer, renal cancer, ovarian cancer, prostate cancer, histiocytic lymphoma, neurofibromatosis, acute mycloid leukemia, myelodysplastic syndrome, leukemia, tumor angiogenesis, medullary thyroid cancer, carcinoid, small cell lung cancer, Kaposi's sarcoma, pheochromocytoma, pain, and polycystic kidney disease. In a preferred embodiment, the disease or condition is selected from the group consisting of melanoma, colorectal cancer, thyroid cancer, ovarian cancer, cholangiocarcinoma, pain, and polycystic kidney disease.

In a twenty-sixth aspect, compounds of Formula I can be used in the preparation of a medicament for the treatment of an A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, sarcoma, carcinoma (e.g. gastrointestinal, liver, bile duct (cholangiocarcinoma), colorectal, lung, breast, pancreatic, thyroid, renal, ovarian, prostate), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, *Hepatitis* and *Influenza* viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, sarcoma, gastrointestinal cancer, liver cancer, cholangiocarcinoma, colorectal cancer, lung cancer, breast cancer, pancreatic cancer, thyroid cancer, renal cancer, ovarian cancer, prostate cancer, histiocytic lymphoma, neurofibromatosis, acute myeloid leukemia, myelodysplastic syndrome, leukemia, tumor angiogenesis, medullary thyroid cancer, carcinoid, small cell lung cancer, Kaposi's sarcoma, pheochromocytoma, pain, and polycystic kidney disease. In a preferred embodiment, the disease or condition is selected from the group consisting of melanoma, colorecial cancer, thyroid cancer, ovarian cancer, cholangiocarcinoma, pain, and polycystic kidney disease.

The compounds of Formula I with kinase activity $IC_{50}$ less than 10 µM as determined in a standard assay described herein can be used to treat protein kinase mediated diseases and conditions related to the following protein kinases, including any mutations thereof, for example without limitation:

Abl, related to chronic myeloid leukemia (CML), acute lymphoblastic leukemia (ALL) and acute myelogenous leukemia (AML);

Akt1, related to gastric, prostate, colorectal, ovarian, pancreatic and breast cancer, glioblastoma and leukemia, as well as schizophrenia and bipolar disorders, and also use in combination with other chemotherapeutic drugs;

Akt2, related to hyperglycemia due to peripheral insulin resistance and nonsuppressible hepatic glucose production accompanied by inadequate compensatory hyperinsulinemia, also related to pancreatic, ovarian and breast cancer;

Akt3, related to melanoma, prostate and breast cancer;

ALK, related to non-Hodgkin lymphomas such as diffuse large B-cell lymphoma and anaplastic large cell lymphoma;

Alk5, related to pancreatic and biliary cancers, and cutaneous T-cell lymphoma;

A-Raf, B-Raf or c-Raf-1, related to any and all diseases and conditions described herein;

Brk, related to breast and colon cancer, and head and neck squamous cell carcinoma;

Btk, related to X-linked agammaglobulinemia, acute lymphocytic leukemia, autoimmune diseases such as multiple sclerosis, systemic lupus erythcmatosis, rheumatoid arthritis, and Graves' disease, immune suppression in organ transplant, and drug sensitivity of B-lineage cells;

Cdk2, related to prostate, breast, colorectal and ovarian cancer;

Cdk4, related to glioblastoma (e.g. glioblastoma multiforme), anaplastic astrocytoma, and breast cancer;

Cdk5, related to Alzheimer's disease, amyotrophic lateral sclerosis and Lewy body disease;

Cdk6, related to glioblastoma multiforme, non-Hodgkin's lymphoma, splenic marginal zone lymphoma, T-cell lymphoblastic lymphoma (T-LBL) and T-cell acute lymphoblastic leukemia (T-ALL);

CHK1, related to DNA damage repair, sensitizes cells to chemotherapeutic agents;

Csk, related to colon and pancreatic carcinomas and autoimmune pathology such as type 1 diabetes, rheumatoid arthritis and systemic lupus erythematosus;

EGFR, related to breast, colorectal, bladder, prostate and non small cell lung cancer, squamous cell carcinomas of the head and neck cancer, oral cavity, and esophagus, and glioblastoma multiforme;

EphA1, related to head and neck squamous cell carcinoma, hepatoma and lung cancer;

EphA2, related to aberrant short-range contact-mediated axonal guidance, bladder, breast, prostate, colon, skin, cervical, ovarian, pancreatic and lung cancers, and metastatic melanoma;

EphB2, related to angiogenesis disorder (e.g. ocular angiogenesis disease such as retinopathy), and cancer (e.g. glioblastoma, breast and liver cancer);

EphB4, related to colorectal cancer (CRC), head and neck squamous cell carcinoma, and tumours of the prostate, breast, endometrium, and bladder;

Erk2, related to aberrant proliferation, differentiation, transcription regulation and development, and may be useful in treating inflammation, for example inflammation associated with Lyme neuroborreliosis, and in treating cancers, such as gastric cancer;

Fak, related to colon and breast tumors, and is also related to esophageal squamous cell carcinoma, melanoma, anaplastic astrocytoma, glioblastoma, ductal carcinoma in situ, prostate and hepatocellular carcinoma, and tumor metastases, and may also provide synergistic effects when used with other chemotherapeutic drugs;

FGFR1, related to 8p11 myeloproliferative syndrome;

FGFR2, related to Crouzon Syndrome, Jackson-Weiss Syndrome, Apert Syndrome, craniosynostosis, Pfeiffer Syndrome, acrocephalo syndactyly type V, and Beare-Stevenson Cutis Gyrata Syndrome;

FGFR3, related to angiogenesis, wound healing, achondroplasia, Muenke craniosynostosis, Crouzon syndrome, acanthosis nigricans, thanatophoric dysplasia, bladder carcinomas, and multiple myeloma;

FGFR4, related to cancer of the breast, lung, colon, medullary thyroid, pancreas, ovary, prostate, endometrium, and fallopian tube, head and neck squamous cell carcinomas and leiomyosarcoma;

Flt1, related to non-small cell lung carcinoma, prostate carcinoma, and colorectal cancer;

Flt3, related to acute myeloid leukemia, myelodysplastic syndrome, acute lymphoblastic leukemia;

Flt4, related to primary lymphoedema;

Fms, related to immune disorders, including rheumatoid arthritis, systemic lupus erythematosis (SLE), and transplant rejection, inflammatory diseases including inflammatory bowel syndrome, ulcerative colitis, Crohn's disease, chronic obstructive pulmonary disease (COPD), emphysema, and atherosclerosis, metabolic disorders, including Type I diabetes, Type II diabetes, insulin resistance, hyperglycemia, and lipolysis, disorders of bone structure, mineralization and bone formation and resorption, including osteoporosis, increased risk of fracture, Paget's disease, hypercalcemia, and metastasis of cancer to bone, kidney diseases, including nephritis (e.g. glomerulonephritis, interstitial nephritis, Lupus nephritis), tubular necrosis, diabetes-associated renal complications (e.g. diabetic nephropathy), and hypertrophy, disorders of the central nervous system, including multiple sclerosis, stroke, Alzheimer's disease and Parkinson's disease; inflammatory and chronic pain, including bone pain; and cancers, including multiple myeloma, acute myeloid leukemia, chronic myeloid leukemia (CML), prostate cancer, breast cancer, ovarian cancer, and metastasis of tumors to other tissues;

Frk, related to acute myeloid leukemia and type I diabetes;

Fyn, related to Alzheimer's disease, schizophrenia and prevention of metastases, e.g. in melanoma and squamous cell carcinoma;

GSK3 (Gsk3α and/or Gsk3β), related to CNS disorders such as Alzheimer's disease, Parkinson's disease, amyotrophic lateral sclerosis, diabetes type II, bipolar disorders, stroke, cancer, chronic inflammatory disease, leucopenia, schizophrenia, chronic pain, neuropathic pain, and traumatic head injury;

HCK, related to chronic myelogenous leukemia and acute lymphocytic leukemia;

Her2/Erbb2, related to prostate and breast cancer;

Her4/Erbb4, related to childhood medulloblastoma;

IGF1R, related to prostate cancer, hepatocellular carcinoma;

IKK beta, related to leukemia of T-cells, necrosis, insulin resistance, and malignant neoplasms;

Irak4, related to bacterial infections, immunodeficiency syndrome, Crohn's disease, ulcerative colitis, asthma, chronic bronchitis, cardio hypertrophy, and kidney hypertension;

Itk, related to allergic asthma;

Jak1, related to Hepatitis C virus infection;

Jak2, related to myeloproliferative disorders such as polycythaemia vera, myelofibrosis, essential thrombocythemia, myeloid metaplasia and leukemias, including acute lymphoblastic leukemia, chronic neutrophilic leukemia, juvenile myelomonocytic leukemia, CMML, Philadelphia chromosome-negative CML, megakaryocytic leukemia, and acute erythroid leukemia;

Jak3, related to X-linked severe combined immunodeficiency, myeloproliferative disorders, transplant rejection and autoimmune diseases such as rheumatoid arthritis, inflammatory bowel syndrome, Crohn's disease, systemic lupus erythematosis, ulcerative colitis, psoriasis and multiple sclerosis;

Jnk (Jnk1, Jnk2, Jnk3), related to metabolic diseases including type 1 diabetes, type 2 diabetes, metabolic syndrome, obesity, and hepatic steatosis; cardiovascular diseases such as atherosclerosis, ischemia (e.g. cerebrovascular ischemia, liver ischemia), reperfusion injury, cardiac hypertrophy; renal diseases such as chronic renal failure; neoplastic diseases and associated complications, including chemotherapy-induced hypoxia, prostate tumors, myeloid leukemia and cancers of the liver, bone, skin, brain, pancreas, lung breast, colon, prostate and ovary; transplant rejection; pain of neuropathic or inflammatory origin including acute and chronic pain; inflammatory and autoimmune diseases including age-related macular degeneration, rheumatoid arthritis, inflammatory bowel disease, ulcerative colitis, Crohn's disease, systemic lupus erythematosis, Sjogren's Syndrome, psoriasis, scleroderma, chronic thyroiditis, Grave's disease, myasthenia gravis, and multiple sclerosis, and inflammation in other organs including CNS inflammation, pancreatitis, nephritis, atopic dermatitis, and hepatitis; airway inflammatory diseases such as asthma, allergy, bronchitis, pulmonary fibrosis, chronic obstructive pulmonary disease; neurologic diseases such as stroke, cerebrovascular ischemia, neurodegenerative diseases such as Parkinson's disease, Alzheimer's disease, amyotrophic lateral sclerosis, dementia, senile chorea, head and spinal cord trauma, and Huntington's disease. More particularly, Jnk1 is related to type 1 diabetes, type 2 diabetes, metabolic syndrome, obesity and hepatic steatosis, Jnk2 is related to atherosclerosis, and Jnk3 is related to inflammatory diseases including autoimmune diseases such as rheumatoid arthritis, inflammatory bowel syndrome, Crohn's disease, systemic lupus erythematosis, Sjogren's Syndrome, psoriasis and multiple sclerosis, airway inflammatory diseases such as asthma, allergy, pulmonary fibrosis, and chronic obstructive pulmonary disease, and inflammation in other organs, such as CNS inflammation, pancreatitis, nephritis, and hepatitis; neurologic diseases such as stroke, cerebrovascular ischemia, and neurodegenerative diseases such as Parkinson's disease, Alzheimer's disease, and Huntington's disease; and neoplastic diseases such as prostate tumors and mycloid leukemia;

Kdr, related to anti-angiogenesis for treating solid tumor growth (e.g. ovarian, lung, breast, prancreatic, prostate, colon, gastrointestinal stromal tumor, non small cell lung cancer, and epidermoid cancer), metastasis, psoriasis, rheumatoid arthritis, diabetic retinopathy and age related macular degeneration;

Kit, related to malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myclocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia;

Lck, related to acute lymphoblastic leukemia, T-cell lymphoma, lymphopenia, renal carcinoma, colon carcinoma, severe combined immunodeficiency, multiple sclerosis, inflammatory bowel and type I diabetes;

Lyn, related to dyslipidemia, dyslipoproteinemia, metabolic syndrome, septicemia, type II diabetes, cancer, obesity, pancreatitis, hypertension, renal disease, inflammation, and impotence;

MAP2K1, related to acute myeloid leukemia, breast, ovarian and liver cancer;

MAP2K2, related to cancer and inflammation;

MAP4K4, related to metabolic indications, including re-sensitizing fat and muscle cells to insulin, ameliorating the pathology in adipocytes, ameliorating the pathology in muscle cells, metabolic syndrome, and type II diabetes; a broad range of oncology indications, including blocking the migration, invasion and metastasis in many different tumor types; and T-cell mediated autoimmune diseases; MAPKAPK2, cancer (e.g. prostate, breast), stroke, menengitis, and inflammatory disorders;

Met, related to kidney, breast, bladder, non-small-cell lung, colorectal, and bladder cancers, and hepatocellular carcinoma;

Mnk1, related to conditions associated with heat shock, nutrient deprivation, oxidative or osmotic stress, and infection of mammalian cells (e.g. with viruses such as adenovirus (Ad) or influenza virus), and autoimmune diseases;

MLK1, related to neurodegenerative diseases such as Alzheimer's disease and Parkinson's disease, and inflammatory disorders;

mTOR, related to neuronal tumors, breast cancer, prostate cancer, acute myelogenous leukemia, lung cancer, pancreatic cancer, colon cancer, renal cancer and myeloma;

p38, related to acute coronary syndrome, stroke, atherosclerosis, and inflammatory autoimmune diseases such as rheumatoid arthritis, inflammatory bowel disease, and Crohn's disease;

PDGFR (PDGFRA, PDGFRB), related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis. More particularly, PDGFRA related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis, and PDGFRB related to idiopathic hypereosinophilic syndrome, chronic eosinophilic leukemia, juvenile myelomonocytic leukemia, and metastatic medulloblastoma;

PDPK1, related to cancer and diabetes;

PI3K (including PI3Kα, PI3Kβ, PI3Kδ and PI3Kγ), related to inflammatory disease, including asthma, chronic obstructive pulmonary disease, bronchitis, emphysema, eosinophilia, lung fibrosis, osteoarthritis, ankylosing spondylitis, sepsis, septic shock, inflammatory myopathies, meningitis, encephalitis, lacrimal parotid gland syndrome, acute respiratory distress syndrome and pancreatitis, graft vs. host disease; allergies, including allergic rhinitis, type I hypersensitivity reactions, atopic dermatitis, contact dermatitis, and eczema; cardiovascular disease, including atherosclerosis, pulmonary hypertension, deep venous thrombosis, stroke, myocardial infarction, myocardial contractility disorders, ischemia, thromoemolism, pulmonary embolism, acute arterial ischemia, peripheral thrombotic occlusions, coronary artery disease and acute coronary syndrome; autoimmune disease, including systemic lupus erythematosus, rheumatoid arthritis, multiple sclerosis, glomerulonephritis, scleroderma, chronic thyroiditis, Graves' disease, autoimmune gastritis, type I diabetes, autoimmune hemolytic anemia, autoimmune neutropenia, thrombocytopenia, atopic dermatitis, myasthenia gravis, inflammatory bowel disease, ulcerative colitis, Crohn's disease, psoriasis, and Sjogren's syndrome; cancers, including ovarian cancer, cervical cancer, breast cancer, colorectal cancer, endometrial cancer, gastric carcinomas, hepatocellular carcinoma, pancreatic cancer, small and non-small cell lung cancer, thyroid carcinoma, lymphomas, multiple myelomas, leukemias (e.g. acute myelogenous leukemia, chronic myclogenous leukemia), neuroblastomas and glioblastomas;

Pim1, related to cancers such as hematopoietic (e.g. acute myeloid and acute lymphoid leukemias) and prostate cancers, and non-Hodgkin's lymphomas;

Pim2, related to lymphomas;

Pim3, related to hepatocellular carcinoma;

PKC alpha, related to pituitary tumors and prefrontal cortical dysfunction such as distractibility, impaired judgment, impulsivity, and thought disorder, also may be used to sensitize chemotherapy in breast, colon, and non small cell lung cancers;

PKC beta, related to diabetic retinopathy;

PKC-theta, related to insulin resistance, T-cell lymphoma;

Plk1, related to cancers (e.g. lymphoma of the thyroid, non-Hodgkin's lymphomas, colorectal cancers, leukemias and melanoma), also useful as sensitizer in chemotherapy;

Pyk2, related to inflammation (e.g. osteoporosis, polycystic kidney disease, rheumatoid arthiritis and inflammatory bowel disease), CNS disease (e.g. Parkinson's disease and Alzheimer's disease), stroke and cancers (e.g. gliomas, breast cancer, and pancreatic cancer);

Ret, related to cancer of the thyroid, neuroblastoma, familial medullary thyroid carcinoma (FMTC), multiple endocrine neoplasia type IIA and IIB (MEN2A, MEN2B), and neurodegenerative disorders (e.g. Hirschsprung's disease, Parkinson's disease, Alzheimer's disease, and amyotrophic lateral sclerosis);

ROCK (ROCK-1, ROCK-2), related to cancers (e.g. ovarian cancer, hepatocellular carcinoma, pancreatic cancer), ocular disease (e.g. glaucoma), cardiac hypertrophy, improved renal perfusion, transplant rejection, and acute respiratory distress syndrome;

Ron, related to cancer and inflammation;

Src, related to cancer and osteoporosis;

Stk6, related to gastric, bladder, breast, lung, CNS, ovarian, kidney, colon, prostate, pancreas, and cervical cancers, melanoma, leukemia, and neuroblastoma;

Syk; related to lymphomas (e.g. mantle cell lymphoma);

TEC, related to sepsis, septic shock, inflammation, rheumatoid arthritis, Crohn's disease, irritable bowel disease (IBD), and ulcerative colitis;

Tie2 (TEK), related to cancer, arthritis (e.g. rheumatoid arthritis), and atherosclerosis;

TrkA, related to pain (e.g. chronic pain, neuropathic pain), cancer (e.g. prostate cancer, lung cancer, pancreatic cancer), allergic disorders (e.g. asthma), arthritis, diabetic retinopathy, macular degeneration and psoriasis;

TrkB, related to obesity, hyperphagia, developmental delays, cancer (e.g. prostate cancer, lung cancer, Wilms tumors, neuroblastoma, pancreatic cancer), various neuropathies (e.g. stroke, multiple sclerosis, transverse myelitis, and encephalitis), and diabetes.

Yes, related to various cancers including esophageal squamous cell carcinoma; and Zap70, related to AIDS, systemic lupus erythematosus, myasthenia gravis, atherosclerosis, rejection of transplanted organs or tissues, allograft rejection including acute and chronic allograft rejection, graft versus host disease, rheumathoid arthritis, psoriasis, systemic sclerosis, atopic dermatitis, eczematous dermatitis, alopecia, and inflammation of the nasal mucus membrane, including all forms of rhinitis.

Additional aspects and embodiments will be apparent from the following Detailed Description of the Invention and from the claims.

DETAILED DESCRIPTION OF THE INVENTION

As used herein the following definitions apply unless clearly indicated otherwise:

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^{1}H$, $^{2}H$, $^{3}H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

"Halogen" refer to all halogens, that is, chloro (Cl), fluoro (F), bromo (Br), or iodo (I).

"Hydroxyl" or "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched lower alkyl group is chemically feasible and attached at any available point to provide a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A "substituted lower alkyl" denotes lower alkyl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of —F, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)—R$^o$, —N(R$^o$)—S(O)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^f$, and —R$^g$. Further, possible substitutions include subsets of these substitutions, such as are indicated herein, for example, in the description of compounds of Formula I, attached at any available atom to provide a stable compound. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2 or 3 fluoro atoms. It is understood that substitutions are chemically feasible and attached at any available atom to provide a stable compound.

"Lower alkynyl" alone or in combination means a straight or branched hydrocarbon containing 2-6 carbon atoms (unless specifically defined) containing at least one, preferably one, carbon to carbon triple bond. The straight chain or branched lower alkynyl group is chemically feasible and attached at any available point to provide a stable compound. Examples of alkynyl groups include ethynyl, propynyl, butynyl, and the like. A "substituted lower alkynyl" denotes lower alkynyl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of —F, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^z$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^p$)—R$^c$, —N(H)—C(O)—R$^o$, —N(H)—C(S)—R$^o$, —N(R)—C(O)—R$^o$, —N(R$^o$)—C(S)—R$^o$, —N(H)—S(O)—R$^o$, —N(R$^o$)—S(O)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—

R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, and —R$^g$. Further, possible substitutions include subsets of these substitutions, such as are indicated herein, for example, in the description of compounds of Formula I, attached at any available atom to provide a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. It is understood that substitutions are chemically feasible and attached at any available atom to provide a stable compound "Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. "Cycloalkylene" is a divalent cycloalkyl. A "substituted cycloalkyl" is a cycloalkyl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)—R$^o$, —N(R$^o$)—S(O)—R$^o$, —N(H) —S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$. It is understood that substitutions are chemically feasible and attached at any available atom to provide a stable compound.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted. i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. "Heterocycloalkylene" is a divalent heterocycloalkyl. A "substituted heterocycloalkyl" is a heterocycloalkyl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. "Arylene" is a divalent aryl. A "substituted aryl" is an aryl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—

N(H)—C(O)—R°, —S(O)$_2$—N(R°)—C(O)—R°, —S(O)$_2$—N(H)—C(S)—R°, —S(O)$_2$—N(R°)—C(S)—R°, —C(NH)—N(H)—R°, —C(NH)—N(R$^p$)—R$^c$, —N(H)—C(O)—R°, —N(H)—C(S)—R°, —N(R°)—C(O)—R°, —N(R°)—C(S)—R°, —N(H)—S(O)—R°, —N(R°)—S(O)—R°, —N(H)—S(O)$_2$—R°, —N(R°)—S(O)$_2$—R°, —N(H)—C(O)—N(H)—R°, —N(H)—C(S)—N(H)—R°, —N(R°)—C(O)—NH$_2$, —N(R°)—C(S)—NH$_2$, —N(R°)—C(O)—N(H)—R°, —N(R°)—C(S)—N(H)—R°, —N(H)—C(O)—N(R°)—R°, —N(H)—C(S)—N(R°)—R°, —N(R°)—C(O)—N(R°)—R°, —N(R°)—C(S)—N(R°)—R°, —N(H)—S(O)$_2$—N(H)—R°, —N(R°)—S(O)$_2$—NH$_2$, —N(R°)—S(O)$_2$—N(H)—R°, —N(H)—S(O)$_2$—N(R°)—R°, —N(R°)—S(O)$_2$—N(R°)—R°, —N(H)—R°, —N(R°)—R°, —R$^d$, —R$^e$, —R$^f$, and —R$^g$. A "substituted arylene" is a divalent substituted aryl. It is understood that substitutions are chemically feasible and attached at any available atom to provide a stable compound.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is provided. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen containing heteroaryl" refers to heteroaryl wherein any heteroatoms are N. "Heteroarylene" is a divalent heteroaryl. A "substituted heteroaryl" is a heteroaryl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R°, —S—R°, —O—C(O)—R°, —O—C(S)—R°, —C(O)—R°, —C(S)—R°, —C(O)—O—R°, —C(S)—O—R°, —S(O)—R°, —S(O)$_2$—R°, —C(O)—N(H)—R°, —C(S)—N(H)—R°, —C(O)—N(R°)—R°, —C(S)—N(R°)—R°, —S(O)—N(H)—R°, —S(O)—N(R°)—R°, —S(O)$_2$—N(H)—R°, —S(O)$_2$—N(R°)—R°, —C(O)—N(H)—O—R°, —C(O)—N(R°)—O—R°, —C(S)—N(H)—O—R°, —C(S)—N(R°)—O—R°, —C(O)—N(H)—S(O)$_2$—R°, —C(O)—N(R°)—S(O)$_2$—R°, —C(S)—N(H)—S(O)$_2$—R°, —C(S)—N(R°)—S(O)$_2$—R°, —S(O)$_2$—N(H)—C(O)—R°, —S(O)$_2$—N(R°)—C(O)—R°, —S(O)$_2$—N(H)—C(S)—R°, —S(O)$_2$—N(R°)—C(S)—R°, —C(NH)—N(H)—R°, —C(NH)—N(R$^p$)—R$^c$, —N(H)—C(O)—R°, —N(H)—C(S)—R°, —N(R°)—C(O)—R°, —N(R°)—C(S)—R°, —N(H)—S(O)—R°, —N(R°)—S(O)—R°, —N(H)—S(O)$_2$—R°, —N(R°)—S(O)$_2$—R°, —N(H)—C(O)—N(H)—R°, —N(H)—C(S)—N(H)—R°, —N(R°)—C(O)—NH$_2$, —N(R°)—C(S)—NH$_2$, —N(R°)—C(O)—N(H)—R°, —N(R°)—C(S)—N(H)—R°, —N(H)—C(O)—N(R°)—R°, —N(H)—C(S)—N(R°)—R°, —N(R°)—C(O)—N(R°)—R°, —N(R°)—C(S)—N(R°)—R°, —N(H)—S(O)$_2$—N(H)—R°, —N(R°)—S(O)$_2$—NH$_2$, —N(R°)—S(O)$_2$—N(H)—R°, —N(H)—S(O)$_2$—N(R°)—R°, —N(R°)—S(O)$_2$—N(R°)—R°, —N(H)—R°, —N(R°)—R°, —R$^d$, —R$^e$, —R$^f$, and —R$^g$. "Substituted heteroarylene" is a divalent substituted heteroaryl. It is understood that substitutions are chemically feasible and attached at any available atom to provide a stable compound.

The variables R°, R$^p$, R$^c$, R$^d$, R$^e$, R$^f$ and R$^g$ as used in the description of optional substituents for alkyl, alkenyl, alkynyl, cycloalkyl, heterocycloalkyl, aryl and heteroaryl are defined as follows:

each R°, R$^p$, and R$^c$ are independently selected from the group consisting of R$^d$, R$^e$, R$^f$, and R$^g$, or R$^p$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —N(R$^u$)—R$^u$, —R$^x$, and —R$^y$;

each R$^d$ is independently lower alkyl, wherein lower alkyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)—N(H)—R$^k$, —S(O)—N(R$^k$)—R$^k$, —S(O)$_2$—N(H)—R$^k$, —S(O)$_2$—N(R$^k$)—R$^k$, —C(O)—N(H)—O—R$^k$, —C(O)—N(R$^k$)—O—R$^k$, —C(S)—N(H)—O—R$^k$, —C(S)—N(R$^k$)—O—R$^k$, —C(O)—N(H)—S(O)$_2$—R$^k$, —C(O)—N(R$^k$)—S(O)$_2$—R$^k$, —C(S)—N(H)—S(O)$_2$—R$^k$, —C(S)—N(R$^k$)—S(O)$_2$—R$^k$, —S(O)$_2$—N(H)—C(O)—R$^k$, —S(O)$_2$—N(R$^k$)—C(O)—R$^k$, —S(O)$_2$—N(H)—C(S)—R$^k$, —S(O)$_2$—N(R$^k$)—C(S)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)—R$^k$, —N(R$^k$)—S(O)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R)—S(O)$_2$—N(R$^k$)—R$^k$, —N(H)—R$^k$, —N(R$^k$)—R$^k$, —R$^i$, and —R$^j$;

each R$^e$ is independently lower alkenyl, wherein lower alkenyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)—N(H)—R$^k$, —S(O)—N(R$^k$)—R$^k$, —S(O)$_2$—N(H)—R$^k$, —S(O)$_2$—N $(R^k)$—$R^k$, —C(O)—N(H)—O—$R^k$, —C(O)—N($R^k$)—O—$R^k$, —C(S)—N(H)—O—$R^k$, —C(S)—N($R^k$)—O—$R^k$, —C(O)—N(H)—S(O)$_2$—$R^o$, —C(O)—N($R^k$)—S(O)$_2$—$R^k$, —C(S)—N(H)—S(O)$_2$—$R^o$, —C(S)—N($R^k$)—S(O)$_2$—$R^k$, —S(O)$_2$—N(H)—C(O)—$R^k$, —S(O)$_2$—N($R^k$)—C(O)—$R^k$, —S(O)$_2$—N(H)—C(S)—$R^k$, —S(O)$_2$—N($R^k$)—C(S)—$R^k$, —C(NH)—N(H)—$R^k$, —C(NH)—N($R^m$)—$R^n$, —N(H)—C(O)—$R^k$, —N(H)—C(S)—$R^k$, —N($R^k$)—C(O)—$R^k$, —N($R^k$)—C(S)—$R^k$, —N(H)—S(O)—$R^k$, —N($R^o$)—S(O)—$R^k$, —N(H)—S(O)$_2$—$R^k$, —N($R^k$)—S(O)$_2$—$R^k$, —N(H)—C(O)—N(H)—$R^k$, —N(H)—C(S)—N(H)—$R^k$, —N($R^k$)—C(O)—NH$_2$, —N($R^k$)—C(S)—NH$_2$, —N($R^k$)—C(O)—N(H)—$R^k$, —N($R^k$)—C(S)—N(H)—$R^k$, —N(H)—C(O)—N($R^k$)—$R^k$, —N(H)—C(S)—N($R^k$)—$R^k$, —N($R^k$)—C(O)—N(R)—$R^k$, —N($R^k$)—C(S)—N($R^k$)—$R^k$, —N(H)—S(O)$_2$—N(H)—$R^k$, —N($R^k$)—S(O)$_2$—NH$_2$, —N($R^k$)S(O)$_2$—N(H)—$R^k$, —N(H)—S(O)$_2$—N($R^k$)—$R^k$, —N($R^k$)—S(O)$_2$—N($R^k$)—$R^k$, N(H)—$R^k$, —N($R^k$)—$R^k$, $R^h$ and —$R^j$;

each $R^f$ is independently lower alkynyl, wherein lower alkynyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—$R^k$, —S—$R^k$, —O—C(O)—$R^k$, —O—C(S)—$R^k$, —C(O)—$R^k$, —C(S)—$R^k$, —C(O)—O—$R^k$, —C(S)—O—$R^k$, —S(O)—$R^k$, —S(O)$_2$—$R^k$, —C(O)—N(H)—$R^k$, —C(S)—N(H)—$R^k$, —C(O)—N($R^k$)—$R^k$, —C(S)—N($R^k$)—$R^k$, —S(O)—N(H)—$R^k$, —S(O)—N($R^k$)—$R^k$, —S(O)$_2$—N(H)—$R^k$, —S(O)$_2$—N($R^k$)—$R^k$, —C(O)—N(H)—O—$R^k$, —C(O)—N($R^k$)—O—$R^k$, —C(S)—N(H)—O—$R^k$, —C(S)—N($R^k$)—O—$R^k$, —C(O)—N(H)—S(O)$_2$—$R^k$, —C(O)—N($R^k$)—S(O)$_2$—$R^k$, —C(S)—N(H)—S(O)$_2$—$R^k$, —C(S)—N($R^k$)—S(O)$_2$—$R^k$, —S(O)$_2$—N(H)—C(O)—$R^k$, —S(O)$_2$—N($R^k$)—C(O)—$R^k$, —S(O)$_2$—N(H)—C(S)—$R^k$, —S(O)$_2$—N($R^k$)—C(S)—$R^k$, —C(NH)—N(H)—$R^k$, —C(NH)—N($R^m$)—$R^n$, —N(H)—C(O)—$R^k$, —N(H)—C(S)—$R^k$, —N($R^k$)—C(O)—$R^k$, —N($R^k$)—C(S)—$R^k$, —N(H)—S(O)—$R^k$, —N($R^k$)—S(O)—$R^k$, —N(H)—S(O)$_2$—$R^k$, —N($R^k$)—S(O)$_2$—$R^k$, —N(H)—C(O)—N(H)—$R^k$, —N(H)—C(S)—N(H)—$R^k$, —N($R^k$)—C(O)—NH$_2$, —N($R^k$)—C(S)—NH$_2$, —N($R^k$)—C(O)—N(H)—$R^k$, —N($R^k$)—C(S)—N(H)—$R^k$, —N(H)—C(O)—N($R^k$)—$R^k$, —N(H)—C(S)—N($R^k$)—$R^k$, —N($R^k$)—C(O)—N($R^k$)—$R^k$, —N($R^k$)—C(S)—N($R^k$)—$R^k$, —N(H)—S(O)$_2$—N(H)—$R^k$, —N($R^o$)—S(O)$_2$—NH$_2$, —N($R^k$)—S(O)$_2$—N(H)—$R^k$, —N(H)—S(O)$_2$—N($R^k$)—$R^k$, —N($R^k$)—S(O)$_2$—N($R^k$)—$R^k$, —N(H)—$R^k$, —N($R^k$)—$R^k$, —$R^h$, and —$R^j$;

each $R^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—$R^k$, —S—$R^k$, —O—C(O)—$R^k$, —O—C(S)—$R^k$, —C(O)—$R^k$, —C(S)—$R^k$, —C(O)—O—$R^k$, —C(S)—O—$R^k$, —S(O)—$R^k$, —S(O)$_2$—$R^k$, —C(O)—N(H)—$R^k$, —C(S)—N(H)—$R^k$, —C(O)—N($R^k$)—$R^k$, —C(S)—N(R)—$R^k$, —S(O)—N(H)—$R^k$, —S(O)—N($R^k$)—$R^o$, —S(O)$_2$—N(H)—$R^o$, —S(O)$_2$—N($R^k$)—$R^k$, —C(O)—N(H)—O—$R^k$, —C(O)—N($R^k$)—O—$R^k$, —C(S)—N(H)—O—$R^k$, —C(S)—N($R^k$)—O—$R^k$, —C(O)—N(H)—S(O)$_2$—$R^k$, —C(O)—N($R^k$)—S(O)$_2$—$R^k$, —C(S)—N(H)—S(O)$_2$—$R^k$, —C(S)—N($R^k$)—S(O)$_2$—$R^k$, —S(O)$_2$—N(H)—C(O)—$R^k$, —S(O)$_2$—N($R^k$)—C(O)—$R^k$, —S(O)$_2$—N(H)—C(S)—$R^k$, —S(O)$_2$—N($R^k$)—C(S)—$R^k$, —C(NH)—N(H)—$R^k$, —C(NH)—N($R^m$)—$R^n$, —N(H)—C(O)—$R^k$, —N(H)—C(S)—$R^k$, —N($R^k$)—C(O)—$R^k$, —N($R^k$)—C(S)—$R^k$, —N(H)—S(O)—$R^k$, —N($R^k$)—S(O)—$R^k$, —N(H)—S(O)$_2$—$R^k$, —N($R^k$)—S(O)$_2$—$R^k$, —N(H)—C(O)—N(H)—$R^k$, —N(H)—C(S)—N(H)—$R^k$, —N($R^k$)—C(O)—NH$_2$, —N($R^k$)—C(S)—NH$_2$, —N($R^k$)—C(O)—N(H)—$R^k$, —N($R^k$)—C(S)—N(H)—$R^k$, —N(H)—C(O)—N($R^k$)—$R^k$, —N(H)—C(S)—N($R^k$)—$R^k$, —N($R^k$)—C(O)—N($R^k$)—$R^k$, —N($R^k$)—C(S)—N($R^k$)—$R^k$, —N(H)—S(O)$_2$—N(H)—$R^k$, —N($R^k$)—S(O)$_2$—NH$_2$, —N($R^k$)—S(O)$_2$—N(H)—$R^k$, —N(H)—S(O)$_2$—N($R^k$)—$R^k$, —N($R^k$)—S(O)$_2$—N($R^k$)—$R^k$, —N(H)—$R^k$, —N($R^k$)—$R^k$, —$R^h$, —$R^i$, and —$R^j$;

wherein $R^k$, $R^m$, and $R^n$ at each occurrence are independently selected from the group consisting of $R^h$, $R^i$, and $R^j$, or $R^m$ and $R^n$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, O—$R^u$, —S—$R^u$, —N(H)—$R^u$, —N($R^u$)—$R^u$, —$R^x$, and —$R^y$;

wherein each $R^h$ is independently lower alkyl optionally substituted with one or more, preferably 1, 2, 3, 4 or 5, also 1, 2, or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—$R^r$, —S—$R^r$, —O—C(O)—$R^r$, —O—C(S)—$R^r$, —C(O)—$R^r$, —C(S)—$R^r$, —C(O)—O—$R^r$, —C(S)—O—$R^o$, —S(O)—$R^r$, —S(O)$_2$—$R^r$, —C(O)—N(H)—$R^r$, —C(S)—N(H)—$R^r$, —C(O)—N($R^r$)—$R^r$, —C(S)—N($R^r$)—$R^r$, —S(O)—N(H)—$R^r$, —S(O)—N($R^r$)—$R^r$, —S(O)$_2$—N(H)—$R^r$, —S(O)$_2$—N(R)—$R^r$, —C(O)—N(H)—O—$R^r$, —C(O)—N($R^r$)—O—$R^r$, —C(S)—N(H)—O—$R^r$, —C(S)—N($R^r$)—O—$R^r$, —C(O)—N(H)—S(O)$_2$—$R^r$, —C(O)—N($R^r$)—S(O)$_2$—$R^r$, —C(S)—N(H)—S(O)$_2$—$R^r$, —C(S)—N($R^r$)—S(O)$_2$—$R^r$, —S(O)$_2$—N(H)—C(O)—$R^r$, —S(O)$_2$—N($R^r$)—C(O)—$R^r$, —S(O)$_2$—N(H)—C(S)—$R^r$, —S(O)$_2$—N($R^r$)—C(S)—$R^r$, —C(NH)—N(H)—$R^r$, —C(NH)—N($R^s$)—$R^r$, —N(H)—C(O)—$R^r$, —N(H)—C(S)—$R^r$, —N($R^r$)—C(O)—$R^r$, —N($R^r$)—C(S)—$R^r$, —N(H)—S(O)—$R^r$, —N($R^r$)—S(O)—$R^r$, —N(H)—S(O)$_2$—$R^r$, —N($R^r$)—S(O)$_2$—$R^r$, —N(H)—C(O)—N(H)—$R^r$, —N(H)—C(S)—N(H)—$R^r$, —N($R^r$)—C(O)—NH$_2$, —N($R^r$)—C(S)—NH$_2$, —N($R^r$)—C(O)—N(H)—$R^r$, —N($R^r$)—C(S)—N(H)—$R^r$, —N(H)—C(O)—N($R^r$)—$R^r$, —N(H)—C(S)—N($R^r$)—$R^r$, —N($R^r$)—C(O)—N($R^r$)—$R^r$, —N($R^r$)—C(S)—N($R^r$)—$R^r$, —N(H)—S(O)$_2$—N(H)—$R^r$, —N($R^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, —R$^r$, and —R$^j$;

wherein each R$^i$ is independently selected from the group consisting of lower alkenyl and lower alkynyl, wherein lower alkenyl or lower alkynyl are optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^o$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)—N(H)—R$^r$, —S(O)—N(R$^r$)—R$^r$, —S(O)$_2$—N(H)—R$^r$, —S(O)$_2$—N(R$^r$)—R$^r$, —C(O)—N(H)—O—R$^r$, —C(O)—N(R$^r$)—O—R$^r$, —C(S)—N(H)—O—R$^r$, —C(S)—N(R$^r$)—O—R$^r$, —C(O)—N(H)—S(O)$_2$—R$^r$, —C(O)—N(R$^r$)—S(O)$_2$—R$^r$, —C(S)—N(H)—S(O)$_2$—R$^r$, —C(S)—N(R$^r$)—S(O)$_2$—R$^r$, —S(O)$_2$—N(H)—C(O)—R$^r$, —S(O)$_2$—N(R$^r$)—C(O)—R$^r$, —S(O)$_2$—N(H)—C(S)—R$^r$, —S(O)$_2$—N(R$^r$)—C(S)—R$^r$, —C(NH)—N(H)—R$^r$, —C(NH)—N(R$^s$)—R$^r$, —N(H)—C(O)—R$^r$, —N(H)—C(S)—R$^r$, —N(R$^r$)—C(O)—R$^r$, —N(R$^r$)—C(S)—R$^r$, —N(H)—S(O)—R$^r$, —N(R$^r$)—S(O)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, and —R$^j$;

wherein each R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)—N(H)—R$^r$, —S(O)—N(R)—R$^r$, —S(O)$_2$—N(H)—R$^r$, —S(O)$_2$—N(R$^r$)—R$^r$, —C(O)—N(H)—O—R$^r$, —C(O)—N(R$^r$)—O—R$^r$, —C(S)—N(H)—O—R$^r$, —C(S)—N(R$^r$)—O—R$^r$, —C(O)—N(H)—S(O)$_2$—R$^r$, —C(O)—N(R$^r$)—S(O)$_2$—R$^r$, —C(S)—N(H)—S(O)$_2$—R$^r$, —C(S)—N(R$^r$)—S(O)$_2$—R$^r$, —S(O)$_2$—N(H)—C(O)—R$^r$, —S(O)$_2$—N(R$^r$)—C(O)—R$^r$, —S(O)$_2$—N(H)—C(S)—R$^r$, —S(O)$_2$—N(R$^r$)—C(S)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)—R$^r$, —N(R$^r$)—S(O)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$ alkynyl, cycloalkyl, heterocycloalkyl, aryl and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or R$^s$ and R$^t$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, O—R$^u$, —S—R$^u$, —N(H)—R$^u$, —N(R$^u$)—R$^u$, —R$^x$, and —R$^y$;

wherein each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each R$^x$ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each R$^y$ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, or optionally substituted lower alkynyl are optionally substituted with one or more, also 1, 2 or 3 groups or substituents selected from the group consisting of fluoro, —NO$_2$, —CN, —O—R$^{1a}$, —S—R$^{1a}$, —N(R$^{1a}$)—R$^{1a}$, —O—C(O)—R$^{1a}$, —O—C(S)—R$^{1a}$, —C(O)—R$^{1a}$, —C(S)—R$^{1a}$, —C(O)—O—R$^{1a}$, —C(S)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —C(O)—N(R$^{1a}$)—O—R$^{1a}$, —C(S)—N(R$^{1a}$)—O—R$^{1a}$, —C(O)—N(R$^{1a}$)—S(O)$_2$—R$^{1a}$, —C(S)—N(R$^{1a}$)—S(O)$_2$—R$^{1a}$, —S(O)$_2$—N(R$^{1a}$)—C(O)—R$^{1a}$, —S(O)$_2$—N(R$^{1a}$)—C(S)—R$^{1a}$, —C(NH)—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —N(R$^{1a}$)—C(O)—N(R$^{1a}$)—R$^{1a}$, —N(R$^{1a}$)—C(S)—N(R$^{1a}$)—R$^{1a}$, —N(R$^{1a}$)—S(O)$_2$—N(R$^{1a}$)—R$^{1a}$, —S(O)—R$^{1a}$, —S(O)$_2$—R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —NO$_2$, —CN, —O—R$^{1a}$, —S—R$^{1a}$, —N(R$^{1a}$)—R$^{1a}$, —O—C(O)—R$^{1a}$, —O—C(S)—R$^{1a}$, —C(O)—R$^{1a}$, —C(S)—R$^{1a}$, —C(O)—O—R$^{1a}$, —C(S)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —C(O)—N(R$^{1a}$)—O—R$^{1a}$, —C(S)—N(R$^{1a}$)—O—R$^{1a}$, —C(O)—N(R$^{1a}$)—S(O)$_2$—R$^{1a}$, —C(S)—N(R$^{1a}$)—S(O)$_2$—R$^{1a}$, —S(O)$_2$—N(R$^{1a}$)—C(O)—R$^{1a}$, —S(O)$_2$—N(R$^{1a}$)—C(S)—R$^{1a}$, —C(NH)—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —N(R$^{1a}$)—C(O)—N(R$^{1a}$)—R$^{1a}$, —N(R$^{1a}$)—C(S)—N(R$^{1a}$)—R$^{1a}$, —N(R$^{1a}$)—S(O)$_2$—N(R$^{1a}$)—R$^{1a}$, —S(O)—R$^{1a}$, —S(O)$_2$—R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —NO$_2$, —CN, —O—R$^{1a}$, —S—R$^{1a}$, —N(R$^{1a}$)—R$^{1a}$, —O—C(O)—R$^{1a}$, —O—C(S)—R$^{1a}$, —C(O)—R$^{1a}$, —C(S)—R$^{1a}$, —C(O)—O—R$^{1a}$, —C(S)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —C(O)—N(R$^{1a}$)—O—R$^{1a}$, —C(S)—N(R$^{1a}$)—O—R$^{1a}$, —C(O)—N(R$^{1a}$)—S(O)$_2$—R$^{1a}$, —C(S)—N(R$^{1a}$)—S(O)$_2$—R$^{1a}$, —S(O)$_2$—N(R$^{1a}$)—C(O)—R$^{1a}$, —S(O)$_2$—N(R$^{1a}$)—C(S)—R$^{1a}$, —C(NH)—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —N(R$^{1a}$)—C(O)—N(R$^{1a}$)—R$^{1a}$, —N(R$^{1a}$)—C(S)—N(R$^{1a}$)—R$^{1a}$, —N(R$^{1a}$)—S(O)$_2$—N(R$^{1a}$)—R$^{1a}$, —S(O)—R$^{1a}$, —S(O)$_2$—R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, wherein R$^{1a}$ is selected from the group consisting of hydrogen, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and wherein —R$^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, or optionally substituted lower alkynyl are optionally substituted with one or more, also 1, 2 or 3 groups or substituents selected from the group consisting of fluoro, —CN, —O—R$^{1a}$, —S—R$^{1a}$, —N(R$^{1a}$)—R$^{1a}$, —C(O)—R$^{1a}$, —C(S)—R$^{1a}$, —C(O)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —S(O)—R$^{1a}$, —S(O)$_2$—R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —O—R$^{1a}$, —S—R$^{1a}$, —N(R$^{1a}$)—R$^{1a}$, —C(O)—R$^{1a}$, —C(S)—R$^{1a}$, —C(O)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —S(O)—R$^{1a}$, —S(O)$_2$—R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —CN, —O—$R^{1a}$, —S—$R^{1a}$, —N($R^{1a}$)—$R^{1a}$, —C(O)—$R^{1a}$, —C(S)—$R^{1a}$, —C(O)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, wherein $R^{1a}$ is selected from the group consisting of hydrogen, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, and wherein —$R^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

"Lower alkoxy" denotes the group —$OR^z$, where $R^z$ is lower alkyl. "Substituted lower alkoxy" denotes lower alkoxy in which $R^z$ is lower alkyl substituted with one or more substituents as indicated herein, for example, in the description of compounds of Formula I, including descriptions of substituted cycloalkyl, heterocycloalkyl, aryl and heteroaryl, attached at any available atom to provide a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. It is understood that substitutions on alkoxy are chemically feasible and attached at any available atom to provide a stable compound.

"Lower alkylthio" denotes the group —$SR^{aa}$, where $R^{aa}$ is lower alkyl. "Substituted lower alkylthio" denotes lower alkylthio in which $R^{aa}$ is lower alkyl substituted with one or more substituents as indicated herein, for example, in the description of compounds of Formula I, including descriptions of substituted cycloalkyl, heterocycloalkyl, aryl and heteroaryl, attached at any available atom to provide a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. It is understood that substitutions on alkylthio are chemically feasible and attached at any available atom to provide a stable compound.

"Amino" or "amine" denotes the group —NH$_2$. "Mono-alkylamino" denotes the group —NHR$^{bb}$ where $R^{bb}$ is lower alkyl. "Di-alkylamino" denotes the group —NR$^{bb}$R$^{cc}$, where $R^{bb}$ and $R^{cc}$ are independently lower alkyl. "Cycloalkylamino" denotes the group —NR$^{dd}$R$^{cc}$, where $R^{dd}$ and $R^{cc}$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. It is understood that when mono-alkylamino, di-alkylamino, or cycloalkylamino are substituents on other moieties, these are chemically feasible and attached at any available atom to provide a stable compound.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailablity. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of two or more reactants that combine to form a complex, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended animal subject for therapeutic purposes that contains at least one pharmaceutically active compound, including any solid form thereof. The composition may include at least one pharmaceutically acceptable component to provide an improved formulation of the compound, such as a suitable carrier or excipient.

The term "pharmaceutically acceptable" indicates that the indicated material does not have properties that would cause a reasonably prudent medical practitioner to avoid administration of the material to a patient, taking into consideration the diseases or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

As used herein in connection with compounds of the invention, the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gall bladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

The present invention concerns compounds of Formula I, and all sub-generic formulae, that are modulators of protein kinases, for example without limitation, the compounds are modulators of at least one of the kinases selected from the group consisting of Ab1, Akt1, Akt2, Akt3, ALK, Alk5, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Pik1, Pyk2, Ret, ROCK 1, ROCK2, Ron, Src, Stk6, Syk, TEC, Tie2, TrkA, TrkB, Yes, and Zap70, and the use of such compounds in the treatment of diseases or conditions.

Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases contemplated by the present invention are described in the art, including, without limitation, protein kinases as described in U.S. patent application Ser. No. 11/473,347 (see also, PCT publication WO2007002433), the disclosure of which is hereby incorporated by reference as it relates to such kinase targets, as well as the following:

A-Raf: Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS->Raf->MEK->ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat Genet. 2006, 38(3):294-6).

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. C-Raf-1 is also implicated as an important mediator of tumor angiogenesis (Hood, J. D. et al., 2002, Science 296, 2404). C-Raf-1 inhibitors may also be useful for the treatment of acute-myeloid leukemia and myelodysplastic syndromes (Crump, Curr Pharm Des 2002, 8(25):2243-8). Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):13942).

Raf inhibitors (A-Raf and/or B-Raf and/or c-Raf-1) may be useful in treating A-Raf-mediated, B-Raf-mediated or c-Raf-1-mediated diseases or conditions selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, sarcoma, carcinoma (e.g. gastrointestinal, liver, bile duct (cholangiocarcinoma), colorectal, lung, breast, pancreatic, thyroid, renal, ovarian, prostate), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, ostcoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, *Hepatitis* and *Influenza* viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenital paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

PI3 kinase family: Phosphoinositide 3-kinases (PI3K) are a family of enzymes that phosphorylate phosphotidylinositol. One of the key signaling pathways in all eukaryotic cells involves this second messenger phosphatidylinositol 3,4,5-triphosphate (PIP3). PIP3 is generated from phosphatidylinositol 4,5-diphosphate (PIP2) by ATP dependent phosphorylation at the 3-position of the inositol ring. This reaction is catalyzed by the PI3-kinase family of lipid kinases. The PI3K family includes three main classes with varied substrate specificity. Class I, in addition to phosphorylating PI, also phosphorylates PI(4)P and PI(4,5)P2. Class II phosphorylates PI and PI(4)P. Class III phosphorylates only PI. Class I PI3K is a heterodimeric molecule composed of a catalytic subunit and a regulatory subunit, wherein for type IA PI3K, one of five regulatory subunits, p85α, p55α, p50α, p85β or p55γ is attached to a p110α, p110β, or p110δ catalytic subunit, and p101 regulatory subunits and p110γ catalytic subunits comprise type IB PI3K. These sub classes are typically referred to as PI3Kα, PI3Kβ, PI3Kδ and PI3Kγ based on the corresponding catalytic subunit. The p110α and p110β are constitutively expressed in all cell types, while p110δ is expressed mainly in leukocytes and some epithelial cells, and p110γ expression is limited to leukocytes. Dysregulation of the Type I PI3-kinases is a frequent event in a variety of human diseases. For example, PI3 kinase-α is frequently mutated in breast, colorectal, and many other cancers. Furthermore, knockout of the γ-isoform, which is primarily expressed in hematopoietic cells, results in mice that are resistant to a variety of inflammatory insults.

PI3 kinases are targets for tumor therapy, as the pathway is regulated by RAS, and is constitutively activated in a variety of human tumors. For example, somatic mutations that activate PI3Kα have been identified, most frequently in the helical domain (E545K and E542K) and kinase domain (H1047R) of p110α (e.g. Engelman et al., Nature medicine 2008, 14(12):1351-1355). Thus, inhibitors of PI3K may be used in the treatment of a variety of cancers, including, but not limited to, ovarian cancer, cervical cancer, breast cancer, colorectal cancer, endometrial cancer, gastric carcinomas, hepatocellular carcinoma, pancreatic cancer, small and non-small cell lung cancer, thyroid carcinoma, lymphomas, multiple myelomas, leukemias (e.g. acute myelogenous leukemia, chronic myelogenous leukemia), neuroblastomas and glioblastomas.

PI3 kinase inhibitors are usefull in treating a variety of other diseases, including, but not limited to inflammatory disease, including, but not limited to, asthma, chronic obstructive pulmonary disease, bronchitis, emphysema, eosinophilia, lung fibrosis, osteoarthritis, ankylosing spondylitis, sepsis, septic shock, inflammatory myopathies, meningitis, encephalitis, lacrimal parotid gland syndrome, acute respiratory distress syndrome and pancreatitis, graft vs. host disease; allergies, including, but not limited to, allergic rhinitis, type I hypersensitivity reactions, atopic dermatitis, contact dermatitis, and eczema; cardiovascular disease, including, but not limited to, atherosclerosis, pulmonary hypertension, deep venous thrombosis, stroke, myocardial infarction, myocardial contractility disorders, ischemia, thromoemolism, pulmonary embolism, acute arterial ischemia, peripheral tirombotic occlusions, coronary artery disease and acute coronary syndrome; autoimmune disease, including, but not limited to, systemic lupus erythematosus, rheumatoid arthritis, multiple sclerosis, glomerulonephritis, scleroderma, chronic thyroiditis, Graves' disease, autoimmune gastritis, type I diabetes, autoimmune hemolytic anemia, autoimmune neutropenia, thrombocytopenia, atopic dermatitis, myasthenia gravis, inflammatory bowel disease, ulcerative colitis, Crohn's disease, psoriasis, and Sjogren's syndrome.

mTOR: The mammalian target of rapamycin (mTOR) is a serine/threonine protein kinase involved in the regulation of cell growth and proliferation, including the regulation of response of tumor cells to nutrients and growth factors. Inhibitors of mTOR are effective in treating a variety of tumors, including, but not limited to, neuronal tumors, breast cancer, prostate cancer, acute myelogenous leukemia, lung cancer, pancreatic cancer, colon cancer, renal cancer and myeloma.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 7-position of the pyrrolo[2,3-d]pyrimidine ring or the nitrogen of the sulfonamide group of compounds of the present invention (e.g. compounds of Formula I), where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalitites, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J. Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such steroisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.c.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds of Formula I can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the invention may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, clorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences*, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the invention are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the invention with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, DMSO, ethyl acetate, acetic acid, or ethanolamine.

Formulations and Administration

The methods and compounds will typically be used in therapy for human subjects. However, they may also be used to treat similar or identical indications in other animal subjects. Compounds of Formula I can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesian trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylenc sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses). HPC (hydroxypropyl cellulose), hydroxyethyl cellulose, hypromellose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds of Formula I may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, polyvinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds of Formula I for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds of Formula I, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds of Formula I for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds of Formula I may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of Formula I may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds of Formula I may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of Formula I, or at the same time as a compound of Formula I. Use in combination also includes use with a therapy or medical procedure that is administered once or infrequently, such as surgery, along with a compound of Formula I administered within a short time or longer time before or after the other therapy or procedure. In some embodiments, the present invention provides for delivery of a compound of Formula I and one or more other drug therapeutics delivered by a different route of administration or by the same route of administration. The use in combination for any route of administration includes delivery of a compound of Formula I and one or more other drug therapeutics delivered by the same route of administration together in any formulation, including formulations where the two compounds are chemically linked in such a way that they maintain their therapeutic activity when administered. In one aspect, the other drug therapy may be co-administered with a compound of Formula I. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound of Formula I and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the present invention are described below. In most cases, alternative techniques can be used. The examples are intended to be illustrative and are not limiting or restrictive to the scope of the invention. In some examples, the mass spectrometry result indicated for a compound may have more than one value due to the isotope distribution of an atom in the molecule, such as a compound having a bromo or chloro substituent.

Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods.

Ring numbering for the 7H-pyrrolo[2,3d]pyrimidine in the following Examples is as follows:

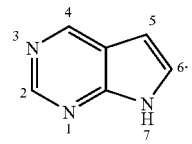

Example 1

Preparation of 7H-pyrrolo[2,3-d]pyrimidine Intermediates 7H-pyrrolo[2,3-d]pyrimidine compounds known in the art may be used in the preparation of starting materials for use in the synthesis of compounds described herein. For example, 2-halo or 4-halo 7H-pyrrolo[2,3-d]pyrimidine can be used to provide starting materials with suitable substitutions at the 2- or 4-position of the 7H-pyrrolo[2,3-d]pyrimidine, e.g. according to the following Schemes I-IX.

Scheme I

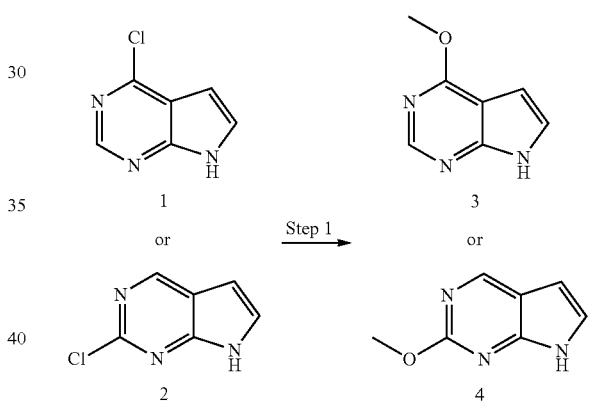

4-methoxy-7H-pyrrolo[2,3-d]pyrimidine (3) or 2-methoxy-7H-pyrrolo[2,3-d]pyrimidine (4) is prepared by reacting 4-chloro-7H-pyrrolo[2,3-d]pyrimidine (1) or 2-chloro-7H-pyrrolo[2,3-d]pyrimidine (2), respectively, with sodium hydroxide in methanol as described by Girgis, N. et. al., J. Heterocyclic. Chem. 1989, 26:317-325.

Scheme II

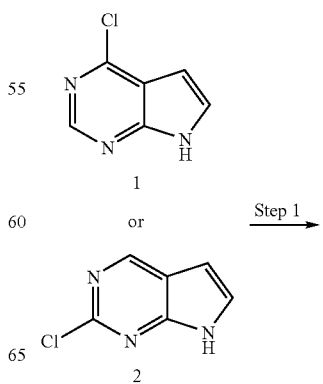

-continued

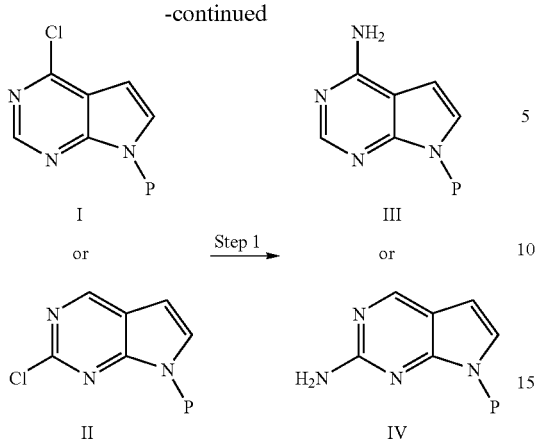

Step 1—Preparation of Compounds of Formula I or II

Compounds of Formula I or II, where P is a suitable protecting group, are prepared by reacting 4-chloro-7H-pyrrolo[2,3-d]pyrimidine (1) or 2-chloro-7H-pyrrolo[2,3-d]pyrimidine (2), respectively, with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction).

Step 2—Preparation of Compound of Formula III or IV

Compounds of Formula III or IV are prepared by reacting compounds of Formula I or II, respectively, with ammonium hydroxide in a suitable solvent or with ammonia in methanol. The desired compound is isolated by conventional means (e.g. extraction). Alternatively, 4-chloro-7H-pyrrolo[2,3-d]pyrimidine (1) or 2-chloro-7H-pyrrolo[2,3-d]pyrimidine (2) can be reacted directly by this method to provide the corresponding compounds without the protecting group.

Scheme III

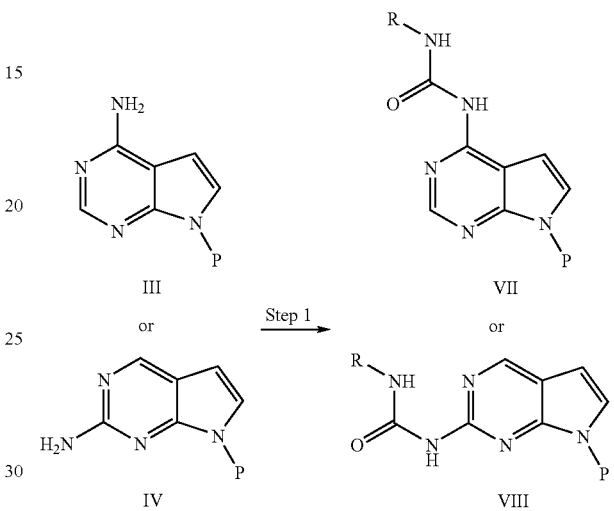

Compounds of Formula V or VI, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared from a compound of Formula III or IV, respectively, by reaction with an activated carboxylic acid of the formula R—C(O)X where X is a leaving group such as chloro (e.g. benzoyl chloride) in the presence of a base (e.g. N,N-diisopropylethylamine (DIEA)) in a non-reactive solvent (e.g. dichloromethane). After stirring for several hours, isolation by conventional means (e.g. extraction and silica gel chromatography) provides compounds of Formula V or VI.

Scheme IV

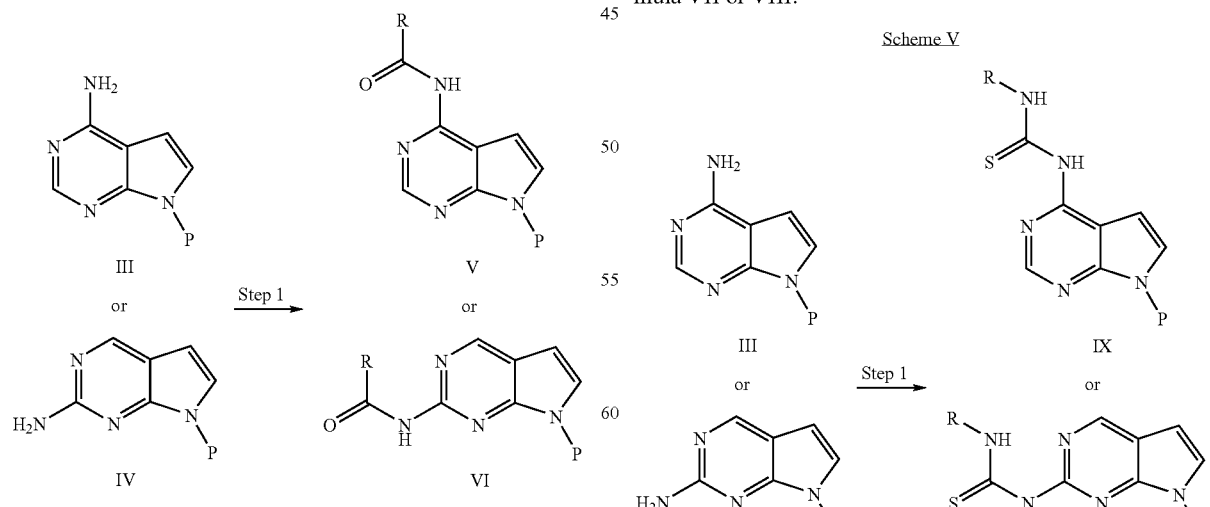

Compounds of Formula VII or VIII, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared from a compound of Formula III or IV, respectively, by reaction with an isocyanate of the formula R—NCO (e.g. propylisocyanate) in the presence of a base (e.g. DIEA) in a non-reactive solvent (e.g. dichloromethane). After stirring for several hours, isolation by conventional means (e.g. extraction and silica gel chromatography) provides compounds of compounds of Formula VII or VIII.

Scheme V

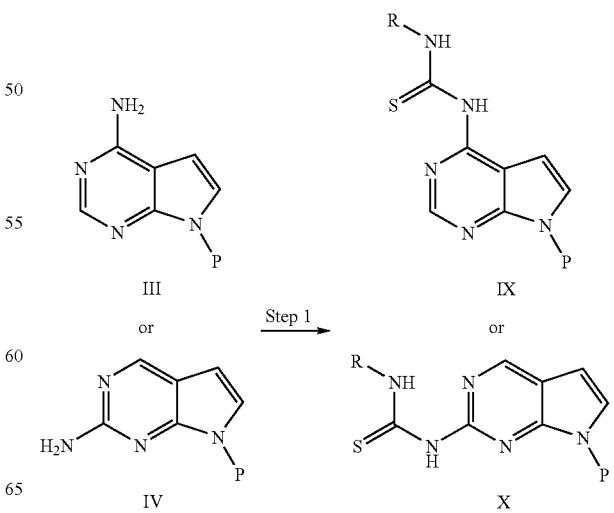

Compounds of Formula IX or X, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared from a compound of Formula III or IV, respectively, by reaction with an isothiocyanate of the formula R—NCS (e.g. propylisothiocyanate) in the presence of a base (e.g. DIEA) in a non-reactive solvent (e.g. dichloromethane). After stirring for several hours, isolation by conventional means (e.g. extraction and silica gel chromatography) provides compounds of Formula IX or X.

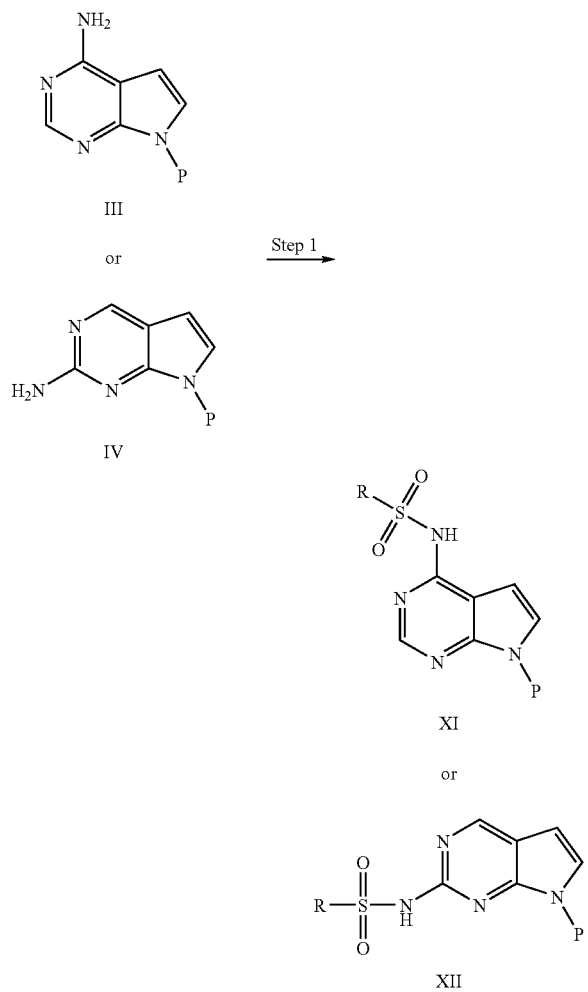

Compounds of Formula XI or XII, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared from a compound of Formula III or IV, respectively, by reaction with a sulfonyl chloride of the formula R—S(O)₂Cl (e.g. propylsulfonyl chloride) in the presence of a base (e.g. DIEA, pyridine) in a non-reactive solvent (e.g. dichloromethane). After stirring for several hours, isolation by conventional means (e.g. extraction and silica gel chromatography) provides compounds of Formula XI or XII.

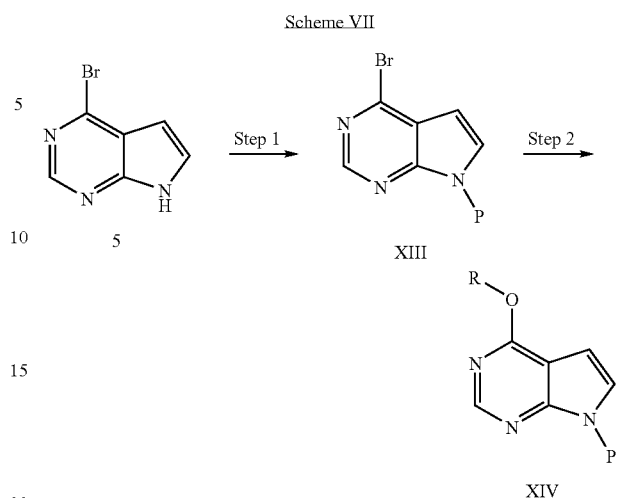

Step 1—Preparation of Compounds of Formula XIII

Compounds of Formula XIII, where P is a suitable protecting group, are prepared by reacting 4-bromo-7H-pyrrolo[2,3-d]pyrimidine (5) with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction).

Step 2—Preparation of Compounds of Formula XIV

Compounds of Formula XIV, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared by a compound of Formula XIII with an alcohol of Formula R—OH in the presence of a base (e.g. sodium hydride) and a copper catalyst (e.g. copper bromide) in a non-reactive solvent (e.g. dimethylformamide) with heating (e.g. 120° C.) for several hours. Isolation by conventional means (e.g. extraction and silica gel chromatography), provides compounds of Formula XIV. Alternatively, 4-bromo-7H-pyrrolo[2,3-d]pyrimidine (5) can be reacted directly by this method to provide the corresponding compounds without the protecting group.

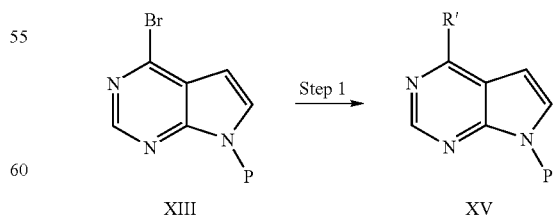

Compounds of Formula XV where R' is optionally substituted lower alkyl and P is a suitable protecting group are prepared by dissolving a compound of Formula XIII in an appropriate solvent (e.g. toluene) followed by the addition of a palladium catalyst (e.g. [1,1'-Bis(diphenylphosphino)ferrocene]dichloropalladium(II), complex with dichloromethane (1:1)). After several minutes, a Grignard reagent of the Formula R'—MgBr is added and the reaction heated (e.g. 90° C.) for one to several hours. After filtration through Celite, isolation by conventional means (e.g. extraction and silica gel chromatography) provides compounds of Formula XV.

Scheme IX

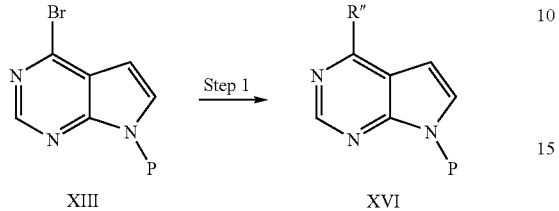

XIII                XVI

Compounds of Formula XVI where R" is optionally substituted aryl or optionally substituted heteroaryl and P is a suitable protecting group are prepared by reacting a compound of Formula XIII with a boronic acid of the Formula R"—B(OH)$_2$ or boronic ester of the Formula R"—B(OR)$_2$ under Suzuki coupling conditions (Muyaura and Suzuki, Chem. Rev. 1995, 95:2457), such as in the presence of a palladium catalyst (e.g. Tetrakis(triphenylphosphine)palladium(0)) and a base (e.g. aqueous potassium carbonate) in an appropriate solvent (e.g. tetrahydrofuran, acetonitrile) with heating thermally (e.g. 80° C.) for one to several hours or heating with a microwave instrument (e.g. 120° C. for 10 minutes). Isolation by conventional means (e.g. extraction and silica gel chromatography) provides compounds of Formula XVI. Alternatively, 4-bromo-7H-pyrrolo[2,3-d]pyrimidine (5) can be reacted by this method to provide the corresponding compounds without the protecting group.

7H-pyrrolo[2,3-d]pyrimidine compounds can be further derivatized at the 5-position, which are used in the synthesis of compounds described herein. The compounds described in Schemes I-IX, or similar compounds known in the art, may be used with or without the protecting group P, which can be readily removed by methods well known in the art. The following Scheme X provides an exemplary method for preparation of useful 5-carbaldehyde derivatives.

Scheme X

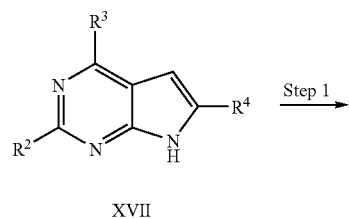

XVII

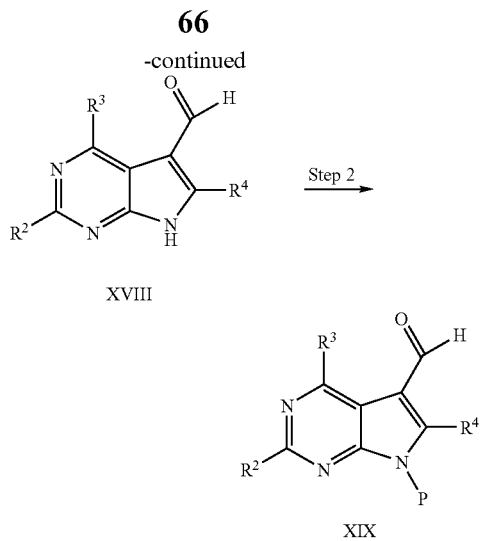

XVIII

XIX

Step 1—Preparation of Compounds of Formula XVIII

Compounds of Formula XVIII are prepared by reacting a compound of Formula XVII (R$^2$, R$^3$ and R$^4$ are as defined in paragraph [0003]) with hexamethyltetramine and acetic acid in water with heating to reflux for two hours. After cooling, the desired compound precipitates and may be collected by filtration.

Step 2—Preparation of Compounds of Formula XIX

Compounds of Formula XIX, where P is a suitable protecting group, are prepared by reacting a compound of Formula XVIII with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction).

Example 2

Preparation of 7H-pyrrolo[2,3-d]pyrimidine Compounds 7H-pyrrolo[2,3-d]pyrimidine compounds known in the art, or prepared as described in Schemes I-X, may be used to prepare compounds described herein as described in the following Schemes XI-XXII.

Scheme XI

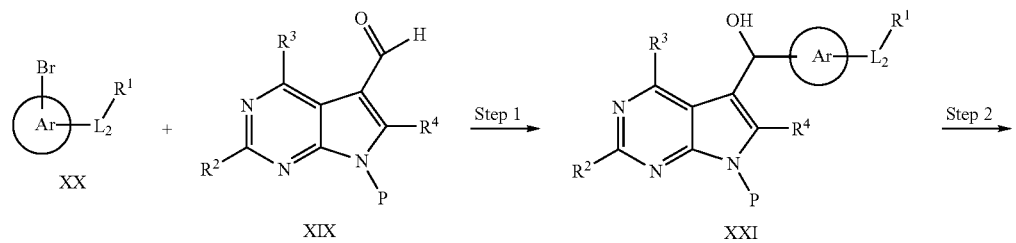

XX         XIX              XXI

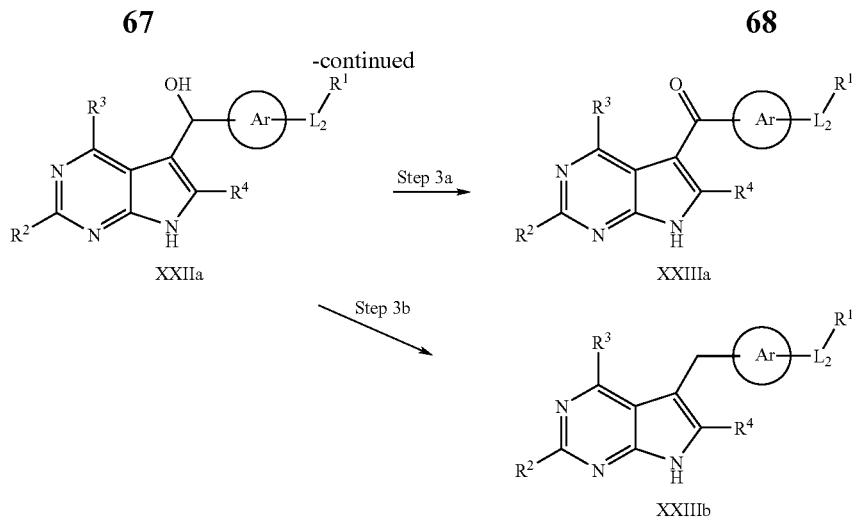

Step 1—Preparation of Compounds of Formula XXI

Compounds of Formula XXI are prepared by reacting a compound of Formula XX (Ar, $L_2$, and $R^1$ are as defined in paragraph [0003], P is a suitable protecting group) in a solvent (e.g. tetrahydrofuran) under an inert atmosphere, with an appropriate organolithium reagent (e.g. butyllithium) or magnesium and stirring the reaction for several hours at −78° C. A compound of Formula XIX ($R^2$, $R^3$ and $R^4$ are as defined in paragraph [0003]) in a solvent (e.g. tetrahydrofuran) is then added to the reaction mixture. The reaction is typically allowed to warm to room temperature and stirred for 30 minutes. The desired compound is isolated by conventional means (e.g. extraction). Compounds of Formula XX are known in the art, for example, as described in U.S. patent application Ser. No. 11/473,347 (see also, PCT publication WO2007002433), the disclosure of which is hereby incorporated by reference as it relates to organic synthesis of compounds.

Step 2—Preparation of Compounds of Formula XXIIa

Compounds of Formula XXIIa are prepared by reacting a compound of Formula XXI with an appropriate reagent to remove the protecting group, P, (e.g. tetra-n-butyl ammonium fluoride) in an appropriate solvent (e.g. tetrahydrofuran). The desired compound is isolated by standard procedures (e.g. extraction and silica gel chromatography).

Step 3a—Preparation of Compounds of Formula XXIIIa

To a compound of Formula XXIIa in an appropriate solvent (e.g. tetrahydrofuran) is added an oxidizing agent (e.g. Dess-Martin periodane, TEMPO, DDQ). Typically, the reaction is allowed to stir at room temperature for 20 minutes. Isolation by conventional means (e.g. extraction and silica gel column chromatography) provides compounds of Formula XXIIIa.

Step 3b—Preparation of Compounds of Formula XXIIIb

To a compound of Formula XXIIa in an appropriate solvent (e.g. acetonitrile) is added a reducing agent (e.g. trifluoroacetic acid and triethylsilane). Typically, the reaction is allowed to stir at room temperature overnight. Isolation by conventional means (e.g. extraction and silica gel column chromatography) provides compounds of Formula XXIIIb.

Compounds of Formula XXI that can be carried through Steps 2 and 3 of Scheme XI may also be prepared following the protocol of the following Scheme XIa.

Scheme XIa

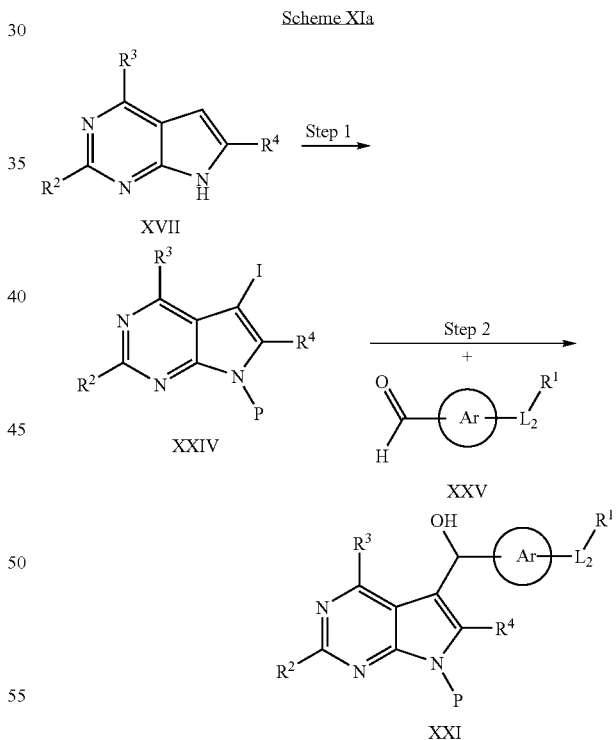

Step 1—Preparation of Compounds of Formula XXIV

Compounds of Formula XXIV are prepared by reacting a compound of Formula XVII ($R^2$, $R^3$ and $R^4$ are as defined in paragraph [0003]) with iodine monochloride in a suitable solvent (e.g. dichloromethane, pyridine) at room temperature for 16-24 hours. The resulting compounds may be isolated by conventional means and reacted with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. Isolation by conventional means (e.g. extraction and silica gel column chromatography) provides compounds of Formula XXIV.

Step 2—Preparation of Compounds of Formula XXI

Compounds of Formula XXI are prepared by reacting a compound of Formula XXIV with a compound of Formula XXV (Ar, $L_2$, and $R^1$ are as defined in paragraph [0003]). Compounds of Formula XXIV are dissolved in a solvent (e.g. tetrahydrofuran) under an inert atmosphere, and cooled to −20° C. and a solution of an appropriate Grignard reagent (e.g. isopropylmagnesium chloride) in tetrahydrofuran is added and the reaction is stirred, coming to 0° C. The reaction is cooled to −20° C. and a compound of Formula XXV in tetrahydrofuran is added to the reaction mixture. The reaction is stirred, coming to 0° C. Isolation by conventional means (e.g. extraction and silica gel chromatography) provides compound of Formula XXI. Compounds of Formula XXV are known in the art, for example, as described in U.S. patent application Ser. No. 11/473,347 (see also, PCT publication WO2007002433), the disclosure of which is hereby incorporated by reference as it relates to organic synthesis of compounds.

Step 1—Preparation of Compounds of Formula XXIIa and XXIIb

To a compound of Formula XVII ($R^2$, $R^3$ and $R^4$ are as defined in paragraph [0003]) and a compound of Formula XXV (Ar, $L_2$ and $R^1$ are as defined in paragraph [10003]) is added an appropriate solvent (e.g. methanol) followed by an appropriate base (e.g. potassium hydroxide, sodium methoxide). The reaction is typically allowed to stir at room temperature overnight. Isolation by conventional means (e.g. extraction, washing and filtering) provides a mixture of compounds of Formula XXIIa and XXIIb which may be separated by silica gel chromatography if desired.

Step 2a—Preparation of Compounds of Formula XXIIIa

To a compound of Formula XXIIa in an appropriate solvent (e.g. tetrahydrofuran) is added an oxidizing agent (e.g. Dess-Martin periodane, TEMPO, DDQ). Typically, the reaction is allowed to stir at room temperature for 20 minutes. Isolation by conventional means (e.g. extraction and silica gel column chromatography) provides compounds of Formula XXIIIa.

Step 2b—Preparation of Compounds of Formula XXIIIb

To a compound of Formula XXIIa and/or XXIIb in an appropriate solvent (e.g. acetonitrile) is added a reducing Scheme XII

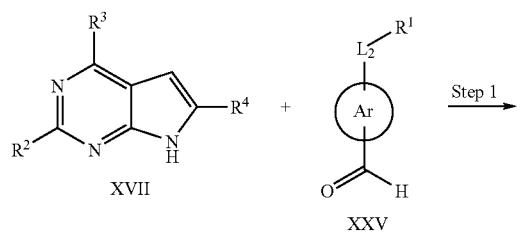

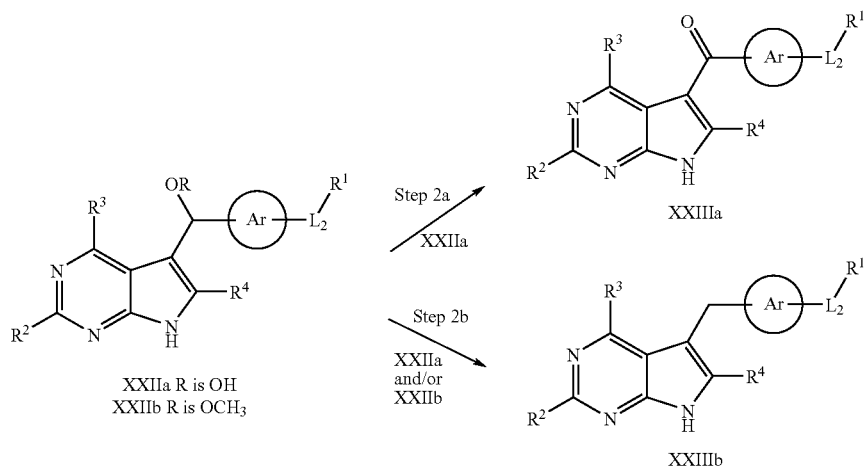

agent (e.g. trifluoroacetic acid and triethylsilane). Typically, the reaction is allowed to stir at room temperature overnight. Isolation by conventional means (e.g. extraction and silica gel column chromatography) provides compounds of Formula XXIIIb.

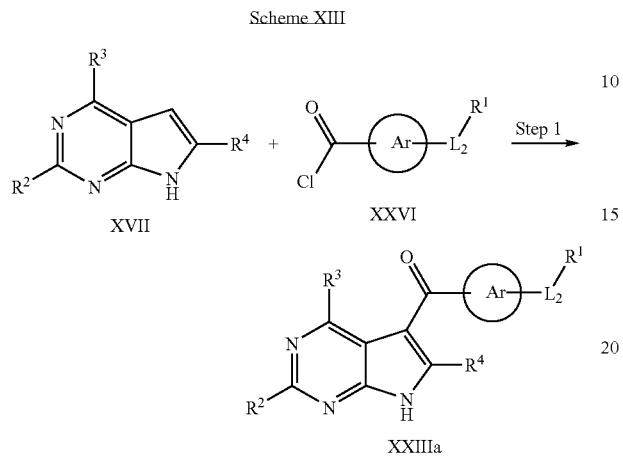

Compounds of Formula XXIIIa are prepared by reacting a compound of Formula XVII (R², R³ and R⁴ are as defined in paragraph [0003]) with a compound of Formula XXVI (Ar, L₂ and R¹ are as defined in paragraph [0003]) in the presence of a Lewis acid (e.g. aluminum trichloride) in an inert solvent (e.g. dichiloromethane) under an inert atmosphere (e.g. argon) at room temperature or with heating up to reflux for 1-18 hours. The desired compound is isolated, for example, by extraction and silica gel column chromatography. Compounds of Formula XXVI are known in the art, for example, as described in U.S. patent application Ser. No. 11/473,347 (see also, PCT publication WO2007002433), the disclosure of which is hereby incorporated by reference as it relates to organic synthesis of compounds.

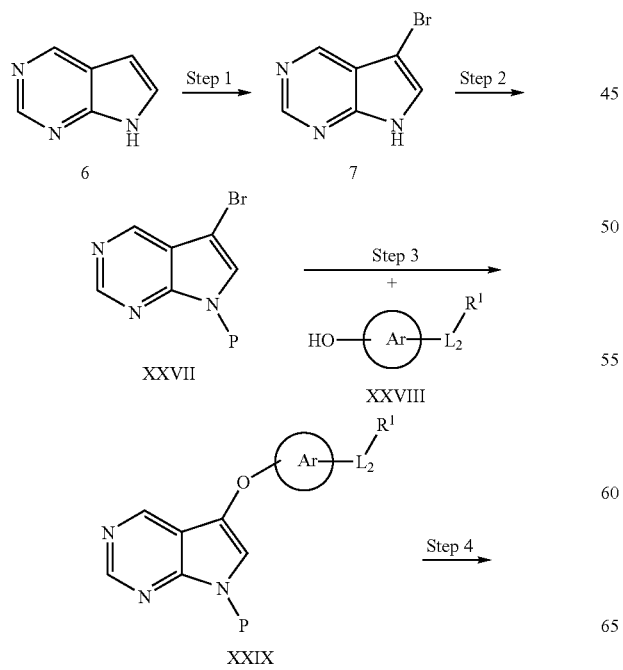

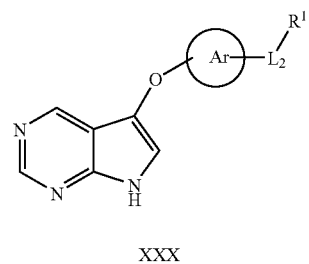

Step 1 Preparation of 5-bromo-7H-pyrrolo[2,3-d]pyrimidine (7)

5-Bromo-7H-pyrrolo[2,3-d]pyrimidine (7) is prepared by dissolving 7H-pyrrolo[2,3-d]pyrimidine (6) in chloroform and slowly adding $Br_2$ in carbon tetrachloride at 0° C. After stirring for 1-2 hours, the reaction may be quenched in aqueous hydrochloric acid. Isolation by conventional means (e.g. extraction and silica gel chromatography) provides compound 7.

Step 2—Preparation of Compounds of Formula XXVII

Compounds of Formula XXVII, where P is a suitable protecting group, are prepared by reacting 5-bromo-7H-pyrrolo [2,3-d]pyrimidine (7) with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction).

Step 3—Preparation of Compounds of Formula XXIX

Compounds of Formula XXIX are prepared by reacting a compound of Formula XXVII with compound of Formula XXVIII (Ar, L₂ and R¹ are as defined in paragraph [0003]) in the presence of a base (e.g sodium hydride) and a copper catalyst (e.g. copper bromide) in a non-reactive solvent (e.g. dimethylformamide) with heating (e.g. 120° C.) for several hours. Isolation by conventional means (e.g. extraction and silica gel chromatography) provides compounds of Formula XXIX.

Step 4—Preparation of Compounds of Formula XXX

Compounds of Formula XXX are prepared by reacting a compound of Formula XXIX with an appropriate reagent to remove the protecting group, P, (e.g. tetra-n-butyl ammonium fluoride) in an appropriate solvent (e.g. tetrahydrofuran). The desired compound is isolated by standard procedures (e.g. extraction and silica gel chromatography).

Scheme XV

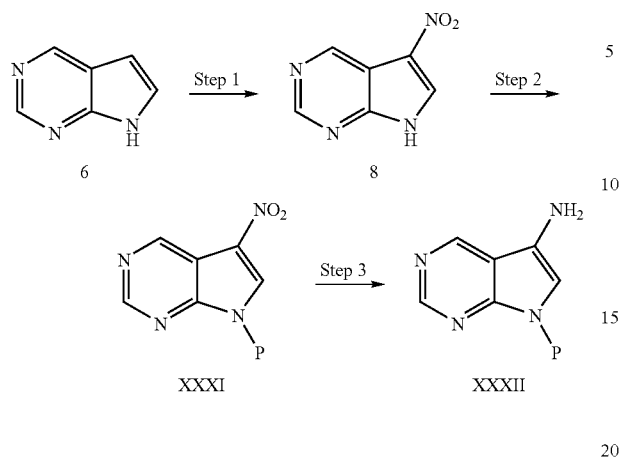

Step 1—Preparation of 5-nitro-7H-pyrrolo[2,3-d]pyrimidine (8)

5-Nitro-7H-pyrrolo[2,3-d]pyrimidine (8) is prepared by adding 7H-pyrrolo[2,3-d]pyrimidine to fuming nitric acid while cooling (e.g. 0° C.). After stirring for one to several hours, water is carefully added and the mixture neutralized with saturated sodium bicarbonate. The solids are collected by filtration and dried to provide 5-nitro-7H-pyrrolo[2,3-d] pyrimidine 8.

Step 2—Preparation of Compounds of Formula XXXI

Compounds of Formula XXXI, where P is a suitable protecting group, are prepared by reacting 5-nitro-7H-pyrrolo[2,3-d]pyrimidine (8) with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction and silica gel chromatography).

Step 3—Preparation of Compounds of Formula XXXII

Compounds of Formula XXXII are prepared from compounds of Formula XXXI by reduction of the nitro group (e.g. hydrogen gas and palladium on carbon in methanol). The mixture is filtered and concentrated to provide compounds of Formula XXXII.

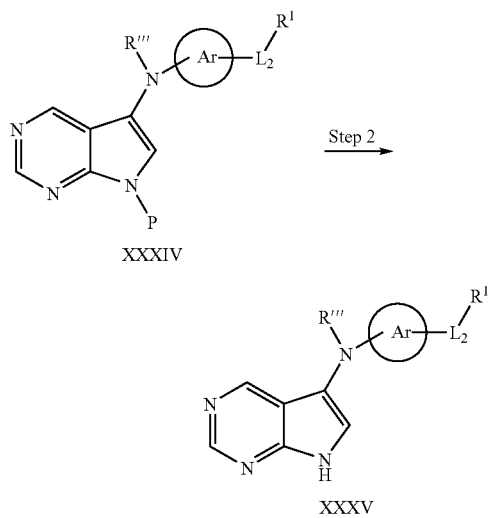

Step 1—Preparation of Compounds of Formula XXXIV

Compounds of Formula XXXIV are prepared by reacting a compound of Formula XXVII (P is a suitable protecting group) with neat compound of Formula XXXIII (Ar, L₂ and R¹ are as defined in paragraph [0003], R''' is e.g. hydrogen, lower alkyl) with heating for several hours (e.g. 150° C.). Alternatively, a compound of Formula XXVII may be reacted with compound of Formula XXXIII using palladium catalyzed Buchwald-Hartwig conditions (i.e. a palladium catalyst (e.g. Tris(dibenzylideneacetone)dipalladium(0)), a ligand (e.g. tri-t-butylphosphine), and a base (e.g. sodium t-butoxide) in a non-reactive solvent (e.g. toluene) with heating (e.g. 80° C.) for several hours). Isolation by conventional means (e.g. extraction and silica gel chromatography) provides compounds of Formula XXXIV.

Step 2—Preparation of Compounds of Formula XXXV

Compounds of Formula XXXV are prepared by reacting a compound of Formula XXXIV with an appropriate reagent to remove the protecting group, P, (e.g. tetra-n-butyl ammonium fluoride) in an appropriate solvent (e.g. tetrahydrofuran). The desired compound is isolated by standard procedures (e.g. extraction and silica gel chromatography).

Scheme XVI

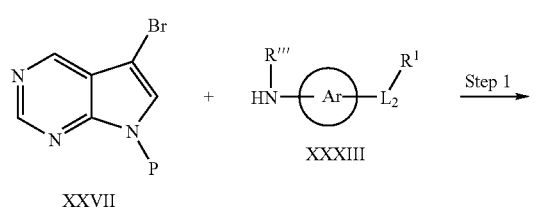

Scheme XVII

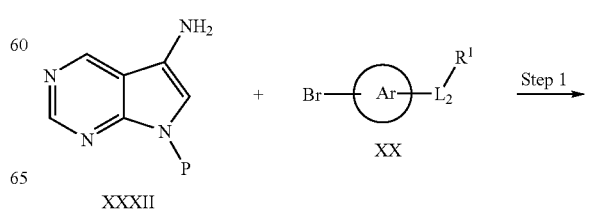

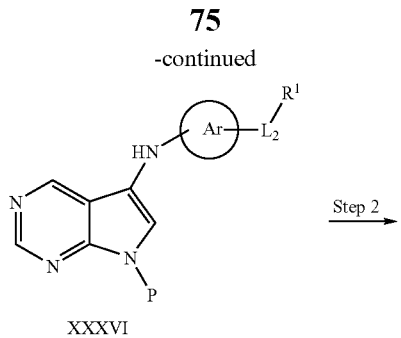

XXXVI

Step 2 →

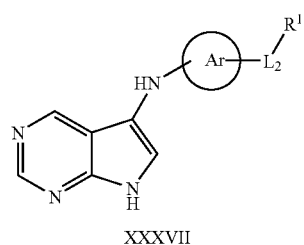

XXXVII

Step 1—Preparation of Compounds of Formula XXXVI

Compounds of Formula XXXVI are prepared by reacting compounds of Formula XXXII (P is a suitable protecting group) with compounds of Formula XX (Ar, $L_2$ and $R^1$ are as defined in paragraph [0003]) with heating for several hours (e.g. 100° C.). Alternatively, compounds of Formula XXXII are reacted with compounds of Formula XX using palladium catalyzed Buchwald-Hartwig conditions (i.e. a palladium catalyst (e.g. Tris(dibenzylideneacetone)dipalladium(0)), a ligand (e.g. tri-t-butylphosphine), and a base (e.g. sodium t-butoxide) in a non-reactive solvent (e.g. toluene) with heating (e.g. 80° C.) for several hours). Isolation by conventional means (e.g. extraction and silica gel chromatography) provides compounds of Formula XXXVI.

Step 2—Preparation of Compounds of Formula XXXVII

Compounds of Formula XXXVII are prepared by reacting a compound of Formula XXXVI with an appropriate reagent to remove the protecting group, P, (e.g. tetra-n-butyl ammonium fluoride) in an appropriate solvent (e.g. tetrahydrofuran). The desired compound is isolated by standard procedures (e.g. extraction and silica gel chromatography).

Scheme XVIII

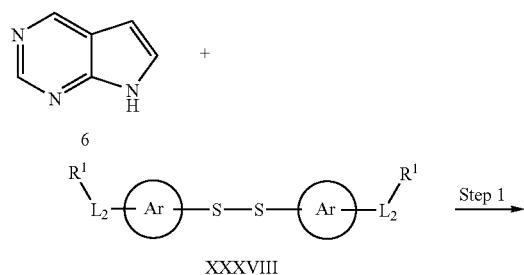

XXXVIII

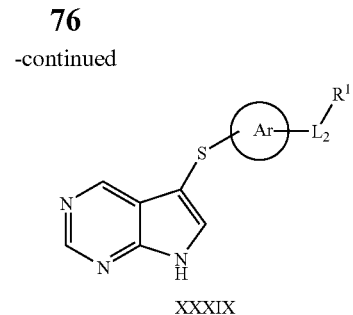

XXXIX

Compounds of Formula XXXIX are prepared by dissolving 7H-pyrrolo[2,3-d]pyrimidine (6) in an appropriate solvent (e.g. dimethylformamide) with a base (e.g. sodium hydride), followed by the addition of a symmetrical aryl disulfide of Formula XXXVIII (Ar, $L_2$ and $R^1$ are as defined in paragraph [0003]). After stirring at room temperature for several hours, the reaction is quenched with water, followed by isolation by conventional means (e.g. extraction and silica gel chromatography) to provide compounds of Formula XXXIX.

Scheme XIX

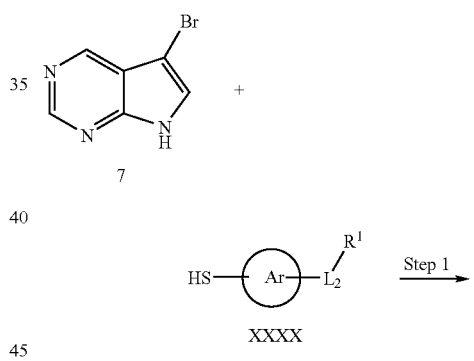

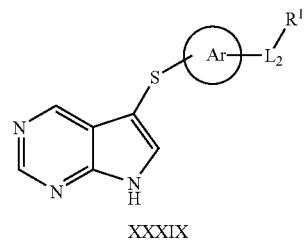

XXXIX

Compounds of Formula XXXIX are prepared by reacting 5-bromo-7H-pyrrolo[2,3-d]pyrimidine (7) with compounds of Formula XXXX (Ar, $L_2$ and $R^1$ are as defined in paragraph [0003]) in the presence of a base (e.g. sodium hydride) in an appropriate solvent (e.g. dimethylformamide) with heating for several hours (e.g. 100° C.). Isolation by conventional means (e.g. extraction and silica gel chromatography) provides compounds of Formula XXXIX.

Scheme XX

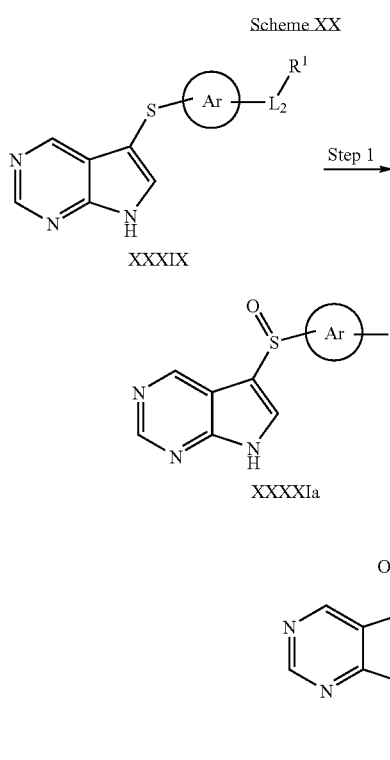

Compounds of Formula XXXXIa or XXXXIb (Ar, L₂ and R¹ are as defined in paragraph [0003]) are prepared by reacting a compound of Formula XXXIX with an oxidizing agent (e.g. meta-chloro-peroxybenzoic acid, hydrogen peroxide) in an appropriate aprotic solvent (e.g. dichloromethane). Compounds of Formula XXXXIa are prepared using 1 equivalent of oxidizing agent, while compounds of Formula XXXXIb are prepared using 2 equivalents of oxidizing agent. Isolation by conventional means (e.g. extraction and silica gel chromatography) provides compound of Formula XXXXIa or XXXXIb.

Scheme XXI

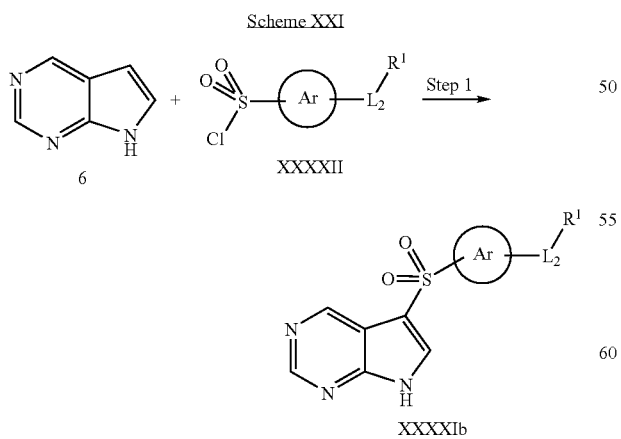

Compounds of Formula XXXXIb (Ar, L₂ and R¹ are as defined in paragraph [0003]) are prepared by reacting 7H-pyrrolo[2,3-d]pyrimidine (6) with a sulfonyl chloride of Formula XXXXII dissolved in trifluoroacetic acid, in the presence of a catalyst (e.g. indium trichloride) and trifluorosulfonic acid with heating (e.g. 70° C.) for a few hours. Neutralization with sodium hydroxide and isolation by conventional means (e.g. extraction and silica gel chromatography) provides compound of Formula XXXXIb (Garzya et al., Tetrahedron Lett. 2004, 45:1499-1501).

Scheme XXII

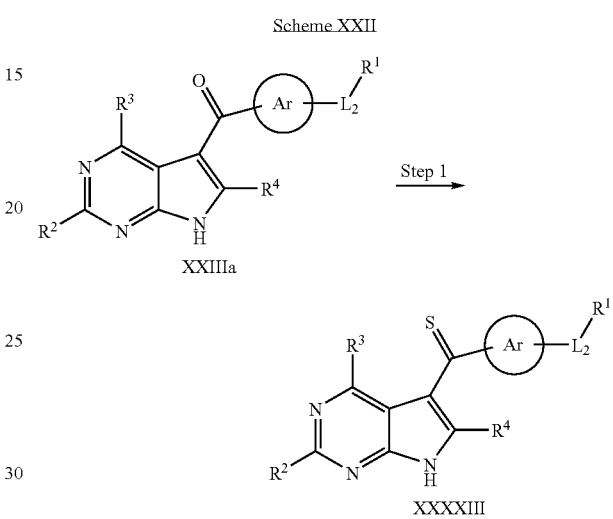

Compounds of Formula XXXXIII (Ar, L₂, R¹, R², R³, and R⁴ are as defined in paragraph [0003]) are prepared by reacting a compound of Formula XXIIIa with Lawesson's reagent, (1,3,2,4-dithiadiphosphetane-2,3-disulfide), in an appropriate solvent (e.g. tetrahydrofuran) with heating for several hours. Isolation by conventional means (e.g. extraction and silica gel chromatography) provides compound of Formula XXXXIII.

Additional methods are known in the art, including methods as described in US Patent Publication Number US20070032519, U.S. patent application Ser. No. 11/473,347 (see also, PCT publication WO2007002433), and U.S. Pat. No. 7,271,262, the disclosures of which are hereby incorporated by reference in their entireties including all specifications, figures, and tables, as it relates to organic synthesis of compounds.

Example 3

Synthesis of propane-1-sulfonic acid [2,4-difluoro-3-7H-pyrrolo[2,3-d]pyrimidine-5-carbonyl)-phenyl]-amide P-0002

Propane-1-sulfonic acid [2,4-difluoro-3-(7H-pyrrolo[2,3-d]pyrimidine-5-carbonyl)-phenyl]-amide P-0002 was prepared in two steps from 7H-pyrrolo[2,3-d]pyrimidine 6 as shown in Scheme 1.

Scheme 1

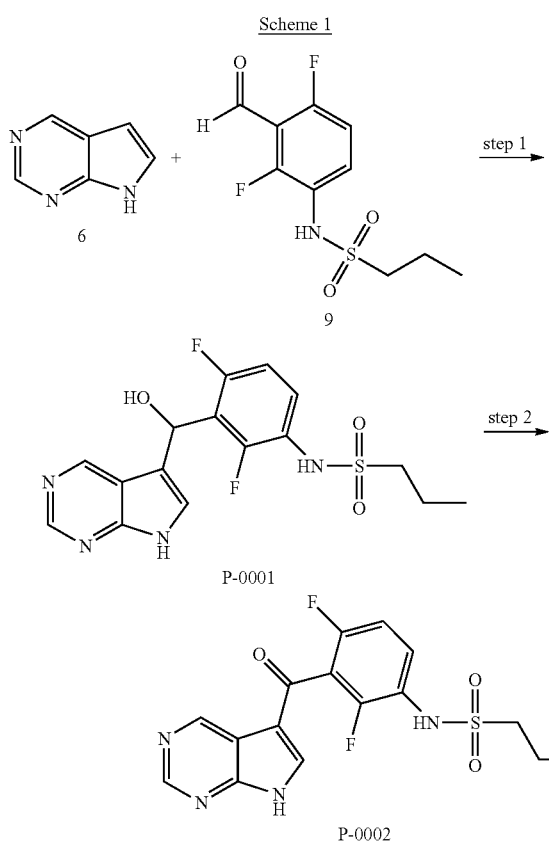

Step 1 Preparation of propane-1-sulfonic acid 2,4-difluoro-3-[hydroxy-(7H-pyrrolo[2,3-d]pyrimidin-5-yl)-methyl]-phenyl-amide (P-0001)

To 7H-pyrrolo[2,3-d]pyrimidine (6, 0.100 g, 0.839 mmol) and propane-1-sulfonic acid (2,4-difluoro-3-formyl-phenyl)-amide (9, 0.258 g, 0.982 mmol), 1.4 mL of methanol was added. This suspension was allowed to stir for 10 minutes, followed by the addition of potassium hydroxide (0.153 g, 2.73 mmol). The reaction was allowed to stir at room temperature for 8 hours, then poured into 5 mL of water and 5 mL of saturated ammonium chloride and extracted with 2×5 mL of ethyl acetate. Organic layers were combined and concentrated under vacuum and the resulting residue was purified by silica gel column chromatography eluting with a gradient of 60 to 100% ethyl acetate in hexanes. Appropriate fractions were combined and concentrated under vacuum to give the desired compound (P-0001, 150 mg), with some 7H-pyrrolo[2,3-d]pyrimidine impurity, used in the next step without further purification. MS(ESI)[M+H$^+$]$^+$=383.2, [M–H$^+$]$^-$=381.5.

Step 2—Preparation of propane-1-sulfonic acid [2,4-difluoro-3-(7H-pyrrolo[2,3-d]pyrimidine-5-carbonyl)-phenyl]-amide (P-0002)

To propane-1-sulfonic acid 2,4-difluoro-3-[hydroxy-(7H-pyrrolo[2,3-d]pyrimidin-5-yl)-methyl]-phenyl-amide (P-0001, 0.150 g, 0.392 mmol), 3 mL of tetrahydrofuran was added, followed by Dess-Martin periodinane (0.166 g, 0.392 mmol). The reaction was allowed to stir at room temperature for 1 hour, then the reaction was extracted with ethyl acetate and 5:1 saturated sodium bicarbonate:saturated sodium thiosulfate. The organic layer was dried with magnesium sulfate, filtered, and the filtrate concentrated under vacuum. The resulting material was purified by silica gel column chromatography eluting with a gradient of 1 to 5% methanol in dichloromethane. Appropriate fractions were combined and concentrated under vacuum to give the desired compound (P-0002, 110 mg). MS(ESI)[M+H$^+$]$^+$=381.2. LC/MS indicated 97.0% purity.

Example 4

Synthesis of N-[2,4-difluoro-3-(7H-pyrrolo[2,3-d]pyrimidine-5-carbonyl)-phenyl]-4-trifluoromethyl-benzenesulfonamide P-0004

N-[2,4-Difluoro-3-(7H-pyrrolo[2,3-d]pyrimidine-5-carbonyl)-phenyl]-4-trifluoromethyl-benzenesulfonamide P-0004 was prepared in two steps from 7H-pyrrolo[2,3-d] pyrimidine 6 as shown in Scheme 2.

Scheme 2

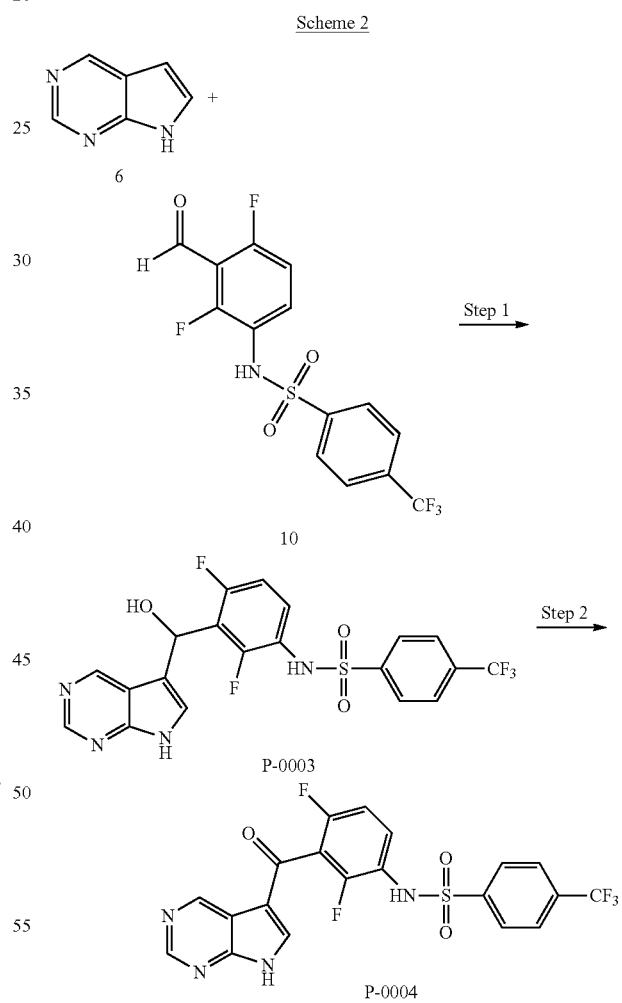

Step 1—Preparation of N-2,4-difluoro-3-[hydroxy-(7H-pyrrolo[2,3-d]pyrimidin-5-yl)-methyl]-phenyl-4-trifluoromethyl-benzenesulfonamide (P-0003)

To 7H-pyrrolo[2,3-d]pyrimidine (6, 0.450 g, 3.78 mmol), N-(2,4-difluoro-3-formyl-phenyl)-4-trifluoromethyl-benzenesulfonamide (10, 1.52 g, 4.16 mmol), and potassium hydroxide (0.689 g, 12.3 mmol), 6.6 mL of methanol was added. The solution was allowed to stir at room temperature for 8 hours, then poured into 50 mL of water and 50 mL of aqueous saturated ammonium chloride and extracted 2×50 mL and 1×25 mL with ethyl acetate. The combined organic layers were washed with water and brine, then dried over magnesium sulfate, filtered and the filtrate concentrated under vacuum. The resulting material was purified by silica gel column chromatography eluting with a gradient of 0-80% ethyl acetate in hexane (with 4% acetic acid) over 15 minutes. Appropriate fractions were combined and concentrated under vacuum to provide the desired compound as a white solid (P-0003, 754 mg). $^1$H-NMR (dmso-d6) consistent with the desired compound. MS (ESI) [M−H$^+$]$^−$=483.4.

Step 2—Preparation of N-[2,4-difluoro-3-(7H-pyr-rolo[2,3-d]pyrimidine-5-carbonyl)-phenyl]-4-trifluoromethyl-benzenesulfonamide (P-0004)

To N-2,4-difluoro-3-[hydroxy-(7H-pyrrolo[2,3-d]pyrimidin-5-yl)-methyl]-phenyl-4-trifluoromethyl-benzenesulfonamide (P-0003, 0.745 g, 1.54 mmol) dissolved in 60 mL of tetrahydrofuran, Dess-Martin periodinane (0.718 g, 1.69 mmol) was added. The resulting mixture was stirred at room temperature for 30 minutes, then diluted with ethyl acetate and a mixture of 50 mL of saturated aqueous sodium bicarbonate and 10 mL of saturated aqueous sodium thiosulfate was added. This was vigorously stirred until the organic layer turned clear. The organic layer was separated and the aqueous layer was extracted with one volume of ethyl acetate. The combined organic layer was washed with water and brine and dried with magnesium sulfate, filtered and the filtrate concentrated under vacuum. The resulting material was purified by silica gel column chromatography eluting with a gradient of 0-80% ethyl acetate in hexane over 15 minutes. Appropriate fractions were combined and concentrated under vacuum to provide the desired compound, which was then dissolved in acetonitrile/methanol, water was added and solvents were removed using a lyophilizer to provide the desired compound as a white solid (P-0004, 530 mg). LC-MS showed one major peak with 98.6% purity. $^1$H-NMR (dmso-d6) was consistent with the desired compound. MS (ESI) [M−H$^+$]$^−$=481.1.

Example 5

Synthesis of propane-1-sulfonic acid [2-fluoro-3-(7H-pyrrolo[2,3-d]pyrimidine-5-carbonyl)-phenyl]-amide P-0006

Propane-1-sulfonic acid [2-fluoro-3-(7H-pyrrolo[2,3-d]pyrimidine-5-carbonyl)-phenyl]-amide P-0006 was synthesized in nine steps from 4-chloro-2-fluoro-phenylamine 11 as shown in Scheme 3.

Scheme 3

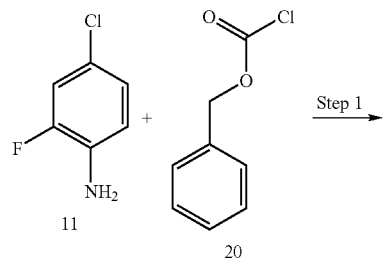

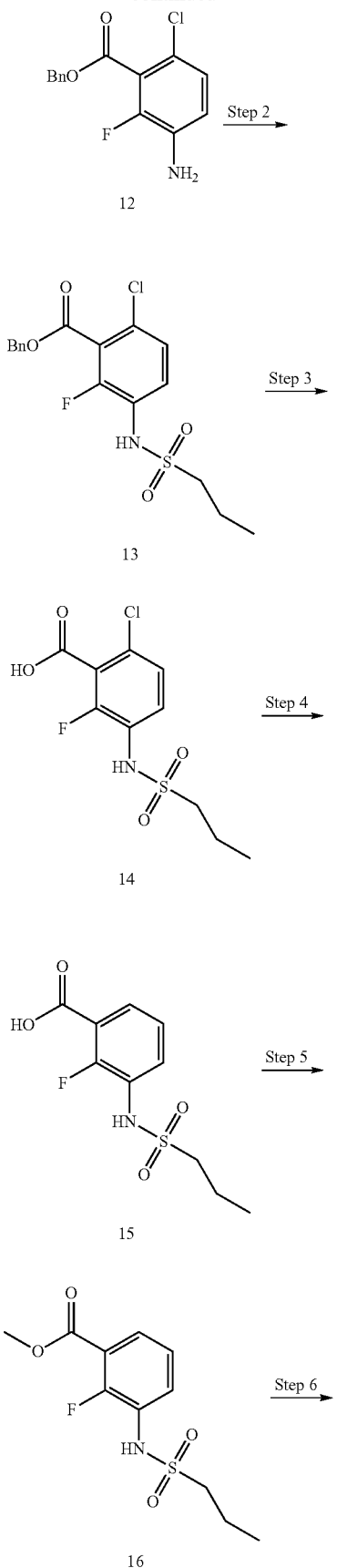

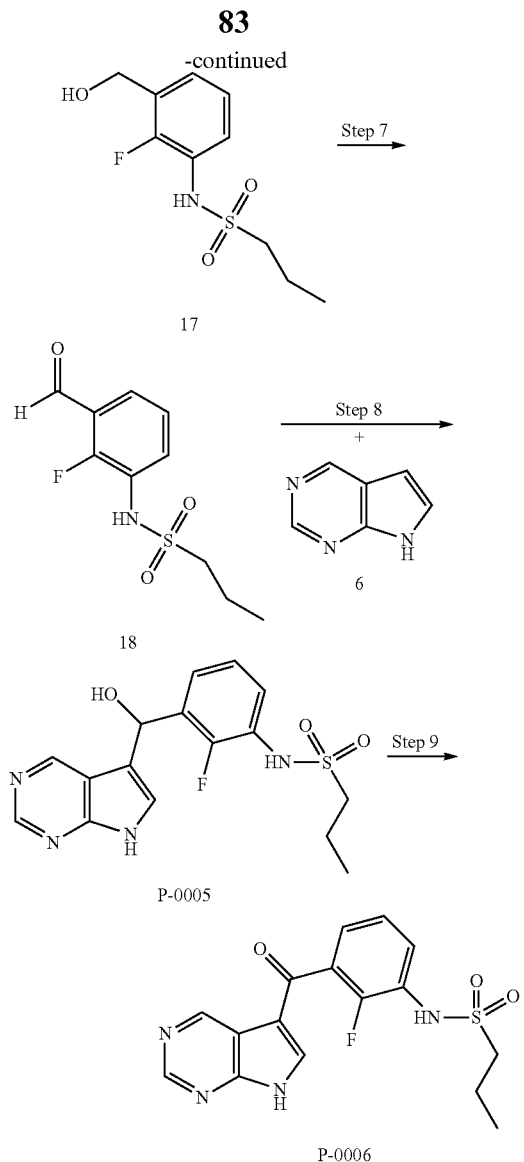

potassium carbonate and extracted with ethyl acetate. The organic layers were combined and washed with brine, dried over anhydrous sodium sulfate, filtered and the filtrate concentrated under vacuum. The resulting material was purified by silica gel column chromatography eluting with 20% ethyl acetate in hexane. Appropriate fractions were combined and concentrated under vacuum to provide the desired compound as a colorless oil (12, 12.5 g, 78.3%). MS(ESI) [M+H$^+$]$^+$=280.0.

Step 2—Preparation of 6-chloro-2-fluoro-3-(propane-1-sulfonylamino)-benzoic acid benzyl ester (13)

To 3-amino-6-chloro-2-fluoro-benzoic acid benzyl ester (12, 1.20 g, 4.3 mmol) in 28 mL of dichloromethane, pyridine (0.52 mL, 6.4 mmol) and propanesulfonyl chloride (0.685 g, 4.8 mmol) were added. The reaction was stirred at room temperature overnight, then poured into water, and extracted with ethyl acetate. The organic layer was washed with brine, dried over anhydrous sodium sulfate, filtered and the filtrate concentrated under vacuum. The resulting material was purified by silica gel column chromatography to provide the desired compound as a colorless oil (13, 960 mg, 58.0%). MS(ESI) [M−H$^+$]$^−$=384.1.

Step 3—Preparation of 6-chloro-2-fluoro-3-(propane-1-sulfonylamino)-benzoic acid (14)

To 6-chloro-2-fluoro-3-(propane-1-sulfonylamino)-benzoic acid benzyl ester (13, 6.00 g, 15.6 mmol) in 100 mL of tetrahydrofuran, 100 mL of 1.0 M aqueous potassium hydroxide was added. The reaction was heated to reflux overnight. The reaction was poured into water, acidified to pH 2 with 1 N hydrochloric acid and extracted with ethyl acetate. The organic portion was dried over anhydrous sodium sulfate, filtered and the filtrate concentrated under vacuum to provide the desired compound as a white solid (14, 3.95 g, 85.8%).

Step 4—Preparation of 2-fluoro-3-(propane-1-sulfonylamino)-benzoic acid (15)

To 6-chloro-2-fluoro-3-(propane-1-sulfonylamino)-benzoic acid (14, 0.69 g, 2.3 mmol) in 10 mL of methanol, 20% palladium hydroxide on carbon (200 mg) was added. The reaction was stirred under hydrogen at 50 psi for 2 hours, then filtered and the filtrate concentrated under vacuum to provide the desired compound 15 as a white solid that was used in the next step without further purification. MS(ESI) [M−H$^+$]$^−$=260.1.

Step 5—Preparation of 2-fluoro-3-(propane-1-sulfonylamino)-benzoic acid methyl ester (16)

To a 2-fluoro-3-(propane-1-sulfonylamino)-benzoic acid (15, 5.05 g, 19.3 mmol) in 100 mL of dichloromethane, N,N-dimethylformamide (0.075 mL, 0.97 mmol) was added under an atmosphere of nitrogen. The reaction was cooled with ice water bath, followed by slow addition of oxalyl chloride (10.8 mL, 2.00 M in dichloromethane, 21.6 mmol). The reaction mixture was stirred at room temperature for 3.0 hours, then cooled with ice water bath, followed by slowly adding 36.0 mL of methanol. The reaction was stirred at room temperature overnight, then concentrated under vacuum. The resulting material was purified by silica gel column chroma- Step 1 Preparation of 3-amino-6-chloro-2-fluoro-benzoic acid benzyl ester (12)

To 4-chloro-2-fluoro-phenylamine (11, 6.30 mL, 57.0 mmol) in 300 mL of tetrahydrofuran, cooled with dry ice/acetone bath under an atmosphere of nitrogen, n-butyllithium (24.4 mL, 2.50 M in hexane) was added slowly. After 20 minutes, 1,2-bis-(chloro-dimethyl-silanyl)-ethane (12.9 g, 60.0 mmol) dissolved in 40.0 mL of tetrahydrofuran was added slowly to the reaction. After 1 hour, n-butyllithium (25.0 mL, 2.50 M in hexane) was added slowly to the reaction. The reaction was stirred at −78° C. for 20 minutes and then allowed to warm to room temperature over 60 minutes. The reaction was cooled to −78° C., followed by slowly adding n-butyllithium (26.0 mL, 2.50 M in hexane). After 80 minutes, benzyl chloroformate (20, 10.0 mL, 70.0 mmol) was added to the reaction. The reaction mixture was stirred at −78° C. overnight followed by addition of 80 mL of water and 25 mL of concentrated hydrochloric acid. The reaction was allowed to warm to room temperature for 2 hours. The organic layer was separated and the aqueous layer was basified with tography eluting with 30% ethyl acetate in hexane. Appropriate fractions were combined and concentrated under vacuum to provide the desired compound as a crude white solid (16, 4.0 g).

Step 6—Preparation of propane-1-sulfonic acid (2-fluoro-3-hydroxymethyl-phenyl)-amide (17)

To 2-fluoro-3-(propane-1-sulfonylamino)-benzoic acid methyl ester (16, 3.80 g, 13.8 mmol) in 133 mL of tetrahydrofuran, lithium tetrahydroaluminate (20.0 mL, 1.00 M in tetrahydrofuran, 20.0 mmol) was added under an atmosphere of nitrogen at room temperature. The reaction was stirred at room temperature for 8 hours, followed by addition of 10 g of $NaSO_4 \cdot 10H_2O$. After 12 hours, the reaction was filtered, the filtrate concentrated under vacuum and the resulting material purified by silica gel column chromatography eluting with 5% methanol in dichloromethane. Appropriate fractions were combined and concentrated under vacuum to provide the desired compound as a white solid (17, 3.0 g, 87.9%).

Step 7—Preparation of propane-1-sulfonic acid (2-fluoro-3-formyl-phenyl)-amide (18)

To propane-1-sulfonic acid (2-fluoro-3-hydroxymethyl-phenyl)-amide (17, 0.20 g, 0.81 mmol) in 5.0 mL of tetrahydrofuran, Dess-Martin periodinane (0.377 g, 0.89 mmol) was added. The reaction was stirred at room temperature for 10 minutes, then poured into water and extracted with ethyl acetate. The organic layer was dried over anhydrous sodium sulfate, and filtered. The filtrate was concentrated under vacuum and purified by silica gel column chromatography eluting with 20% ethyl acetate in hexane. Appropriate fractions were combined and concentrated under vacuum to provide the desired compound as a white solid (18, 100 mg, 50.0%). MS(ESI) $[M-H^+]^-=244.1$.

Step 8—Preparation of propane-1-sulfonic acid {2-fluoro-3-[hydroxy-(7H-pyrrolo[2,3-d]pyrimidin-5-yl)-methyl]-phenyl}-amide (P-0005)

To propane-1-sulfonic acid (2-fluoro-3-formyl-phenyl)-amide (18.75 mg, 0.30 mmol) in 0.6 mL of methanol, 7H-pyrrolo[2,3-d]pyrimidine (6, 73 mg, 0.61 mmol) and potassium hydroxide (51 mg, 0.92 mmol) were added under an atmosphere of nitrogen. The reaction was stirred at room temperature for 24 hours, then poured into water and extracted with ethyl acetate. The organic layer was washed with brine, dried over sodium sulfate and filtered. The filtrate was concentrated under vacuum and purified by silica gel column chromatography eluting with 5% methanol in dichloromethane. Appropriate fractions were combined and concentrated under vacuum to provide the desired compound as a solid (P-0005, 85 mg, 76%). MS(ESI) $[M+H^+]^+=365.1$.

Step 9—Preparation of propane-1-sulfonic acid [2-fluoro-3-(7H-pyrrolo[2,3-d]pyrimidin-5-carbonyl)-phenyl]-amide (P-0006)

To propane-1-sulfonic acid {2-fluoro-3-[hydroxy-(7H-pyrrolo[2,3-d]pyrimidin-5-yl)-methyl]-phenyl}-amide (P-0005, 79 mg, 0.22 mmol) in 1 mL of tetrahydrofuran, Dess-Martin periodane (101 mg, 0.24 mmol) was added. The reaction was stirred at room temperature for one hour. The reaction was poured into sodium thiosulfate and potassium carbonate solution and extracted with ethyl acetate. The organic layer was washed with brine, dried over anhydrous sodium sulfate and filtered. The filtrate was concentrated under vacuum and purified by silica gel column chromatography eluting with 5% methanol in dichloromethane. Appropriate fractions were combined and concentrated under vacuum to provide the desired compound (P-0006, 75 mg, 95%). MS(ESI) $[M+H^+]^+=363.1$.

Example 6

Synthesis of (3-amino-2,6-difluoro-phenyl)-(7H-pyrrolo[2,3-d]pyrimidin-5-yl)-methanone 27 and Use as Intermediate to Synthesis of Additional Compounds (3-Amino-2,6-difluoro-phenyl)-(7H-pyrrolo[2,3-d]pyrimidin-5-yl)-methanone 27 was synthesized in five steps from 2,4-difluoroaniline 19 as shown in Scheme 4.

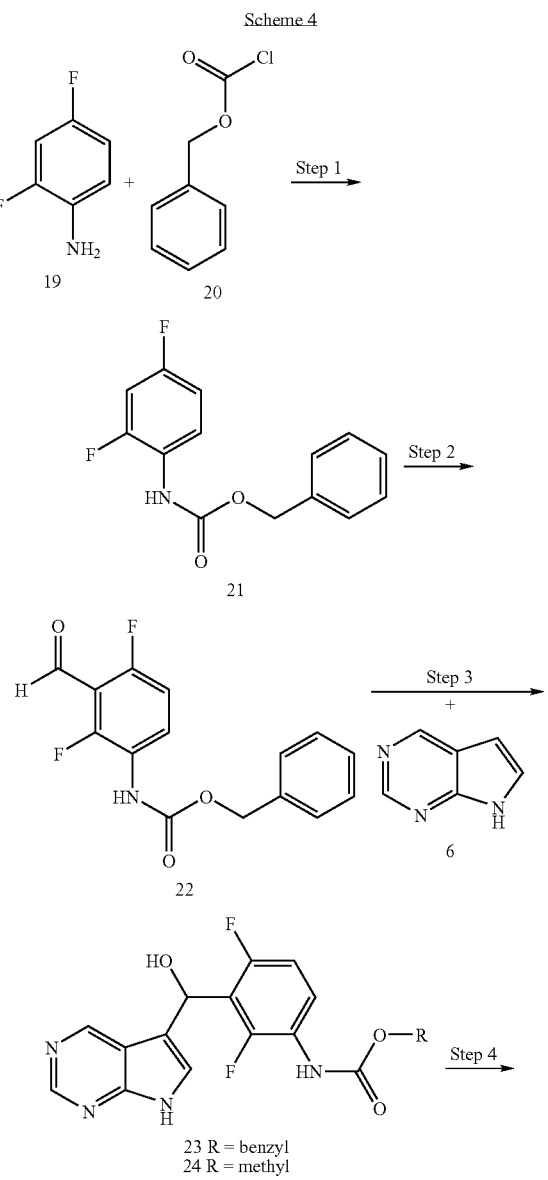

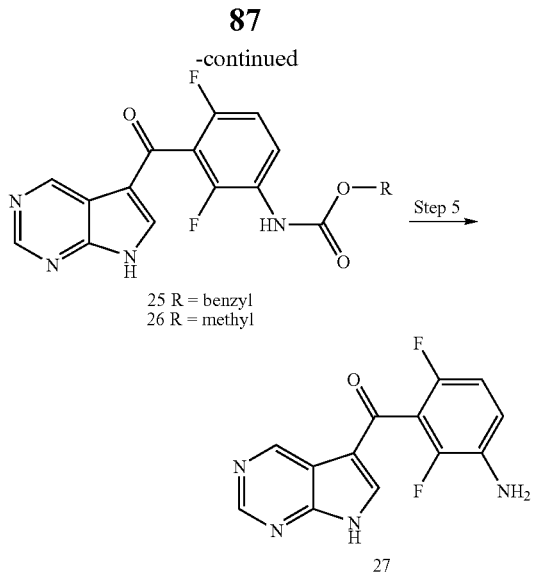

25 R = benzyl
26 R = methyl

27

Step 1—Preparation of (2,4-difluoro-phenyl)-carbamic acid benzyl ester (21)

To 2,4-difluoroaniline (19, 7.0 mL, 70.0 mmol) in 100 mL of dichloromethane, pyridine (11 mL, 0.14 mol) and benzyl chloroformate (20, 11.9 mL, 83.4 mmol) were added. The reaction mixture was stirred at ambient temperature for 1.5 hours. The reaction mixture was concentrated under vacuum and the residue was partitioned between ethyl acetate and postassium bisulfate solution. The organic layer was dried with magnesium sulfate, filtered, and the filtrate concentrated under vacuum. The resulting material was crystallized from hexanes to provide the desired compound (21, 15.6 g, 85%).

Step 2—Preparation of (2,4-difluoro-3-formyl-phenyl)-carbamic acid benzyl ester (22)

Into a round bottom flask was added (2,4-difluoro-phenyl)-carbamic acid benzyl ester (21, 3.83 g, 14.5 mmol) in 148 mL of tetrahydrofuran. The solution was chilled to −78° C. and n-butyllithium (19.1 mL, 1.60 M in hexane, 30.0 mmol) was added over 30 minutes, followed by the addition of N,N-dimethylformamide (1.12 mL, 14.5 mol). The reaction mixture was allowed to warm to ambient temperature and was stirred overnight, then poured into water and extracted with ethyl acetate. The organic layer was washed with brine, dried over sodium sulfate, filtered and the filtrate concentrated under vacuum. The resulting material was crystallized from ether to provide the desired compound (22, 3.0 g, 71%).

Step 3—Preparation of {2,4-difluoro-3-[hydroxy-(7H-pyrrolo[2,3-d]pyrimidin-5-yl)-methyl]-phenyl}-carbamic acid benzyl ester (23) and {2,4-difluoro-3-[hydroxy-(7H-pyrrolo[2,3-d]pyrimidin-5-yl)-methyl]-phenyl}-carbamic acid methyl ester (24)

To 7H-pyrrolo[2,3-]pyrimidine (6, 1.00 g, 8.39 mmol), (2,4-difluoro-3-formyl-phenyl)-carbamic acid benzyl ester (22, 2.93 g, 10.1 mmol), and potassium hydroxide (1.53 g, 27.3 mmol), 10.0 mL of methanol was added. The solution was allowed to stir at room temperature for 32 hours, then poured into 25 mL of water and 25 mL of saturated ammonium chloride and extracted 2×50 mL with ethyl acetate. The combined organic layer was concentrated under vacuum. The crude material was purified by silica gel column chromatography eluting with a gradient of 0-80% ethyl acetate in hexane (with 4% acetic acid) over 15 minutes. Appropriate fractions were combined and concentrated under vacuum to provide 1.066 g of a mixture of compounds 23 and 24, which was used in the next step without further purification. MS(ESI) [M+H$^+$]$^+$=335.4.

Step 4—Preparation of [2,4-difluoro-3-(7H-pyrrolo[2,3-d]pyrimidine-5-carbonyl)-phenyl]-carbamic acid benzyl ester (25) and [2,4-difluoro-3-(7H-pyrrolo[2,3-d]pyrimidine-5-carbonyl)-phenyl]-carbamic acid methyl ester (26)

To a mixture of {2,4-difluoro-3-[hydroxy-(7H-pyrrolo[2,3-d]pyrimidin-5-yl)-methyl]-phenyl}-carbamic acid benzyl ester (23, 1.066 g, 2.598 mmol) and {2,4-difluoro-3-[hydroxy-(7H-pyrrolo[2,3-d]pyrimidin-5-yl)-methyl]-phenyl}-carbamic acid methyl ester (24, 1.066 g, 3.189 mmol) dissolved in 100 mL of tetrahydrofuran, Dess-Martin periodinane (1.43 g, 3.38 mmol) was added. The resulting mixture was stirred at room temperature for 30 minutes, then diluted with ethyl acetate. A mixture of 100 mL of saturated aqueous sodium bicarbonate and 20 mL of saturated aqueous sodium thiosulfate was added, and the mixture was vigorously stirred until the organic layer turned clear. The organic layer was separated and the aqueous layer was extracted once with ethyl acetate. The combined organic layer was washed with water and brine, dried with magnesium sulfate and filtered. The filtrate was concentrated under vacuum and the crude material was purified by silica gel chromatography eluting with a gradient of 0-80% ethyl acetate in hexane over 15 minutes. Appropriate fractions were combined and the solvent removed under vacuum to provide 502 mg of a mixture of compounds 25 and 26, which were used in the next step without further purification.

Step 5—Preparation of (3-amino-2,6-difluoro-phenyl)-(7H-pyrrolo[2,3-d]pyrimidin-5-yl)-methanone (27)

The mixture of [2,4-difluoro-3-(7H-pyrrolo[2,3-d]pyrimidine-5-carbonyl)-phenyl]-carbamic acid benzyl ester (25) and [2,4-difluoro-3-(7H-pyrrolo[2,3-d]pyrimidine-5-carbonyl)-phenyl]-carbamic acid methyl ester (26) from the last step was dissolved in 30 mL of 1,4-dioxane and 25 mL of 10 N aqueous sodium hydroxide was added. The mixture was heated to reflux for 2 hours, then acidified with 6 N hydrochloric acid and adjusted to pH~8 with addition of some sodium bicarbonate. This was extracted with ethyl acetate and the organic layer was washed with water and brine, then dried with magnesium sulfate and filtered. The filtrate was concentrated under vacuum and the resulting residue was suspended in acetonitrile and sonicated for 30 minutes. The precipitated material was collected by filtration to provide the desired compound as a yellow solid (27, 263 mg). $^1$H-NMR (dmso-d6) was consistent with the desired compound. MS(ESI) [M+H$^+$]=274.8.

(3-Amino-2,6-difluoro-phenyl)-(4-methyl-7H-pyrrolo[2,3-d]pyrimidin-5-yl)-methanone 45 and (3-amino-2,6-difluoro-phenyl)-(4-methoxy-7H-pyrrolo[2,3-d]pyrimidin-5-yl)-methanone 46

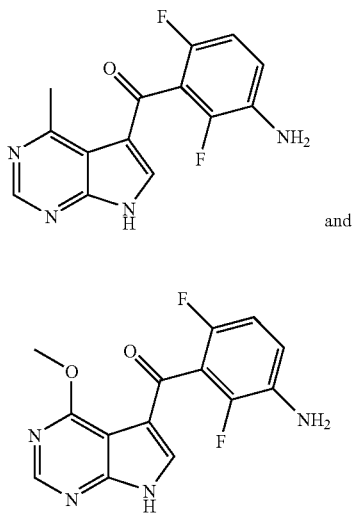

were prepared similarly to the protocol of scheme 4, substituting 7H-pyrrolo[2,3-d]pyrimidine 6 with 4-methyl-7H-pyrrolo[2,3-d]pyrimidine 42 (see Example 9, Scheme 7, step 1) and 4-methoxy-7H-pyrrolo[2,3-d]pyrimidine 3, respectively, in step 3.

4-methoxy-7H-pyrrolo[2,3-d]pyrimidine 3 was prepared in one step from 4-chloro-7H-pyrrolo[2,3-d]pyrimidine 1 as shown in scheme 4b.

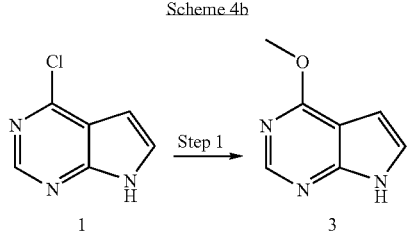

Step 1—Preparation of 4-methoxy-7H-pyrrolo[2,3-d]pyrimidine (3)

To 4-chloro-7H-pyrrolo[2,3-d]pyrimidine (1, 3.5 g, 23.0 mmol) in 70 mL of methanol, potassium hydroxide (2.3 g, 41.0 mmol) was added and the reaction stirred at 60° C. overnight, then poured into water and extracted with ethyl acetate. The organic layer was separated and dried over sodium sulfate, filtered and the filtrate concentrated under vacuum to provide the desired compound (3, 3.20 g).

The resulting (3-amino-2,6-difluoro-phenyl)-(7H-pyrrolo[2,3-d]pyrimidin-5-yl)-methanone (27) was used in a library synthesis to provide a number of compounds according to the following Scheme 4a.

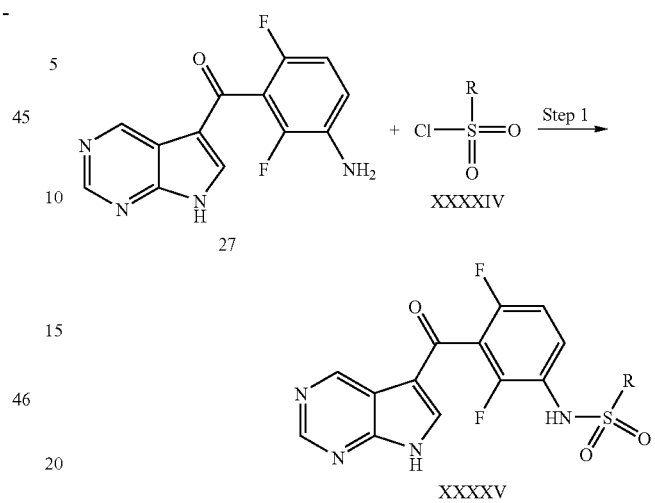

To (3-amino-2,6-difluoro-phenyl)-(7H-pyrrolo[2,3-d]pyrimidin-5-yl)-methanone (27, 20 mg 0.07 mmol) 0.50 mL of tetrahydrofuran is added, followed by the sulfonyl chloride (XXXXIV, 1 to 2 equiv.) as a solution in tetrahydrofuran, followed by addition of pyridine (3 equiv.). The reaction vial is allowed to stir at room temperature or in an oil bath at 60° C. After 1-3 days, the reaction is poured into 10 mL of water and 15 mL of 1N aqueous hydrochloric acid and extracted with 15 mL of ethyl acetate. The organic layer is washed with brine, dried over anhydrous magnesium sulfate and filtered. The filtrate is concentrated under vacuum and purified by silica gel column chromatography to provide the desired sulfonamide compound.

Additional compounds are prepared similarly to the protocol of Scheme 4a, using an appropriate sulfonyl chloride reagent and optionally replacing (3-amino-2,6-difluoro-phenyl)-(7H-pyrrolo[2,3-d]pyrimidin-5-yl)-methanone 27 with (3-amino-2,6-difluoro-phenyl)-(4-methyl-7H-pyrrolo[2,3-d]pyrimidin-5-yl)-methanone 45 or (3-amino-2,6-difluoro-phenyl)-(4-methoxy-7H-pyrrolo[2,3-d]pyrimidin-5-yl)-methanone 46. The following compounds may be or were prepared similarly to the protocol of Scheme 4a:

N-[2,4-Difluoro-3-(7H-pyrrolo[2,3-d]pyrimidine-5-carbonyl)-phenyl]-methanesulfonamide (P-0007),
Ethanesulfonic acid [2,4-difluoro-3-(7H-pyrrolo[2,3-d]pyrimidine-5-carbonyl)-phenyl]-amide (P-0008),
Propane-2-sulfonic acid [2,4-difluoro-3-(7H-pyrrolo[2,3-d]pyrimidine-5-carbonyl)-phenyl]-amide (P-0009),
Butane-2-sulfonic acid [2,4-difluoro-3-(7H-pyrrolo[2,3-d]pyrimidine-5-carbonyl)-phenyl]-amide (P-0010),
2-Methyl-propane-1-sulfonic acid [2,4-difluoro-3-(7H-pyrrolo[2,3-d]pyrimidine-5-carbonyl)-phenyl]-amide (P-0011),
Pentane-2-sulfonic acid [2,4-difluoro-3-(7H-pyrrolo[2,3-d]pyrimidine-5-carbonyl)-phenyl]-amide (P-0012),
Cyclopentanesulfonic acid [2,4-difluoro-3-(7H-pyrrolo[2,3-d]pyrimidine-5-carbonyl)-phenyl]-amide (P-0013),
Cyclohexanesulfonic acid [2,4-difluoro-3-(7H-pyrrolo[2,3-d]pyrimidine-5-carbonyl)-phenyl]-amide (P-0014),
N-[2,4-Difluoro-3-(7H-pyrrolo[2,3-d]pyrimidine-5-carbonyl)-phenyl]-C,C,C-trifluoro-methanesulfonamide (P-0015),
2,2,2-Trifluoro-ethanesulfonic acid [2,4-difluoro-3-(7H-pyrrolo[2,3-d]pyrimidine-5-carbonyl)-phenyl]-amide (P-0016), 3,3,3-Trifluoro-propane-1-sulfonic acid [2,4-difluoro-3-(7H-pyrrolo[2,3-d]pyrimidine-5-carbonyl)-phenyl]-amide (P-0017), Dimethylamine-1-sulfonic acid [3-(7H-pyrrolo[2,3-d]pyrimidine-5-carbonyl)-2,4-difluoro-phenyl]-amide (P-0018), Diethylamine-1-sulfonic acid [3-(7H-pyrrolo[2,3-d]pyrimidine-5-carbonyl)-2,4-difluoro-phenyl]-amide (P-0019), Pyrrolidine-1-sulfonic acid [2,4-difluoro-3-(7H-pyrrolo[2,3-d]pyrimidine-5-carbonyl)-phenyl]-amide (P-0020), Morpholine-4-sulfonic acid [2,4-difluoro-3-(7H-pyrrolo[2,3-d]pyrimidine-5-carbonyl)-phenyl]-amide (P-0021), 2H-[1,2,4]Triazole-3-sulfonic acid [2,4-difluoro-3-(7H-pyrrolo[2,3-d]pyrimidine-5-carbonyl)-phenyl]-amide (P-0022), Thiazole-2-sulfonic acid [2,4-difluoro-3-(7H-pyrrolo[2,3-d]pyrimidine-5-carbonyl)-phenyl]-amide (P-0023), Pyridine-2-sulfonic acid [2,4-difluoro-3-(7H-pyrrolo[2,3-d]pyrimidine-5-carbonyl)-phenyl]-amide (P-0024), N-[2,4-Difluoro-3-(7H-pyrrolo[2,3-d]pyrimidine-5-carbonyl)-phenyl]-2-fluoro-benzenesulfonamide (P-0025), N-[2,4-Difluoro-3-(7H-pyrrolo[2,3-d]pyrimidine-5-carbonyl)-phenyl]-3-fluoro-benzenesulfonamide (P-0026), N-[2,4-Difluoro-3-(7H-pyrrolo[2,3-d]pyrimidine-5-carbonyl)-phenyl]-2,5-difluoro-benzenesulfonamide (P-0027), N-[2,4-Difluoro-3-(7H-pyrrolo[2,3-d]pyrimidine-5-carbonyl)-phenyl]-benzenesulfonamide (P-0028), N-[2,4-Difluoro-3-(7H-pyrrolo[2,3-d]pyrimidine-5-carbonyl)-phenyl]-4-isopropyl-benzenesulfonamide (P-0029), N-[2,4-Difluoro-3-(7H-pyrrolo[2,3-d]pyrimidine-5-carbonyl)-phenyl]-4-propyl-benzenesulfonamide (P-0030), 3-Difluoromethoxy-N-[2,4-difluoro-3-(7H-pyrrolo[2,3-d]pyrimidine-5-carbonyl)-phenyl]-benzenesulfonamide (P-0031), 4-Difluoromethoxy-N-[2,4-difluoro-3-(7H-pyrrolo[2,3-d]pyrimidine-5-carbonyl)-phenyl]-benzenesulfonamide (P-0032), 4-tert-Butyl-N-[2,4-difluoro-3-(7H-pyrrolo[2,3-d]pyrimidine-5-carbonyl)-phenyl]-benzenesulfonamide (P-0033), N-[2,4-Difluoro-3-(7H-pyrrolo[2,3-d]pyrimidine-5-carbonyl)-phenyl]-4-fluoro-benzenesulfonamide (P-0062), Cyclobutanesulfonic acid [2,4-difluoro-3-(7H-pyrrolo[2,3-d]pyrimidine-5-carbonyl)-phenyl]-amide (P-0063), N-[2,4-Difluoro-3-(7H-pyrrolo[2,3-d]pyrimidine-5-carbonyl)-phenyl]-2,4-difluoro-benzenesulfonamide (P-0064), N-[2,4-Difluoro-3-(7H-pyrrolo[2,3-d]pyrimidine-5-carbonyl)-phenyl]-2,6-difluoro-benzenesulfonamide (P-0065), Pyridine-3-sulfonic acid [2,4-difluoro-3-(7H-pyrrolo[2,3-d]pyrimidine-5-carbonyl)-phenyl]-amide (P-0066), N-[2,4-Difluoro-3-(4-methoxy-7H-pyrrolo[2,3-d]pyrimidine-5-carbonyl)-phenyl]-4-propyl-benzenesulfonamide (P-0076), N-[2,4-Difluoro-3-(4-methoxy-7H-pyrrolo[2,3-d]pyrimidine-5-carbonyl)-phenyl]-4-isopropyl-benzenesulfonamide (P-0077), N-[2,4-Difluoro-3-(4-methoxy-7H-pyrrolo[2,3-d]pyrimidine-5-carbonyl)-phenyl]-4-ethyl-benzenesulfonamide (P-0078), N-[2,4-Difluoro-3-(4-methoxy-7H-pyrrolo[2,3-d]pyrimidine-5-carbonyl)-phenyl]-3-fluoro-4-methoxy-benzenesulfonamide (P-0079), N-[2,4-Difluoro-3-(4-methoxy-7H-pyrrolo[2,3-d]pyrimidine-5-carbonyl)-phenyl]-3,5-dimethyl-benzenesulfonamide (P-0080), Pyridine-3-sulfonic acid [2,4-difluoro-3-(4-methoxy-7H-pyrrolo[2,3-d]pyrimidine-5-carbonyl)-phenyl]-amide (P-0081), 4,4-Difluoro-cyclohexanesulfonic acid [2,4-difluoro-3-(4-methoxy-7H-pyrrolo[2,3-d]pyrimidine-5-carbonyl)-phenyl]-amide (P-0082), Cyclohexanesulfonic acid [2,4-difluoro-3-(4-methoxy-7H-pyrrolo[2,3-d]pyrimidine-5-carbonyl)-phenyl]-amide (P-0083), N-[2,4-Difluoro-3-(4-methoxy-7H-pyrrolo[2,3-d]pyrimidine-5-carbonyl)-phenyl]-C-methoxy-methanesulfonamide (P-0084), N-[2,4-Difluoro-3-(4-methyl-7H-pyrrolo[2,3-d]pyrimidine-5-carbonyl)-phenyl]-4-trifluoromethyl-benzenesulfonamide (P-0085), N-[2,4-Difluoro-3-(4-methyl-7H-pyrrolo[2,3-d]pyrimidine-5-carbonyl)-phenyl]-4-propyl-benzenesulfonamide (P-0086), N-[2,4-Difluoro-3-(4-methyl-7H-pyrrolo[2,3-d]pyrimidine-5-carbonyl)-phenyl]-4-isopropyl-benzenesulfonamide (P-0087), N-[2,4-Difluoro-3-(4-methyl-7H-pyrrolo[2,3-d]pyrimidine-5-carbonyl)-phenyl]4-ethyl-benzenesulfonamide (P-0088), N-[2,4-Difluoro-3-(4-methyl-7H-pyrrolo[2,3-d]pyrimidine-5-carbonyl)-phenyl]-3-fluoro-4-methoxy-benzenesulfonamide (P-0089), N-[2,4-Difluoro-3-(4-methyl-7H-pyrrolo[2,3-d]pyrimidine-5-carbonyl)-phenyl]-3,5-dimethyl-benzenesulfonamide (P-0090), Pyridine-3-sulfonic acid [2,4-difluoro-3-(4-methyl-7H-pyrrolo[2,3-d]pyrimidine-5-carbonyl)-phenyl]-amide (P-0091), 4,4-Difluoro-cyclohexanesulfonic acid [2,4-difluoro-3-(4-methyl-7H-pyrrolo[2,3-d]pyrimidine-5-carbonyl)-phenyl]-amide (P-0092), Cyclohexanesulfonic acid [2,4-difluoro-3-(4-methyl-7H-pyrrolo[2,3-d]pyrimidine-5-carbonyl)-phenyl]-amide (P-0093), and N-[2,4-Difluoro-3-(4-methyl-7H-pyrrolo[2,3-d]pyrimidine-5-carbonyl)-phenyl]-C-methoxy-methanesulfonamide (P-0094).

The following table indicates compounds that have been or may be made by this route, where column 1 provides the compound number, column 2 the 7H-pyrrolo[2,3-d]pyrimidine (i.e. 27, 45 or 46), column 3 the sulfonyl chloride XXXXIV, column 4 the resulting compound XXXXV, and column 5 the mass spectrometry results for those compounds that have been made.

| Comp. number | 7H-pyrrolol[2,3-d]pyrimidine | XXXXIV | XXXXV | MS (ESI) [M + H]⁻ |
|---|---|---|---|---|
| P-0007 | | | | |
| P-0008 | | | | 367.1 |
| P-0009 | | | | 381.1 |
| P-0010 | | | | 395.1 |
| P-0011 | | | | 395.1 |
| P-0012 | | | | 409.1 |

-continued
| Comp. number | 7H-pyrrolol[2,3-d]pyrimidine | XXXXIV | XXXXV | MS (ESI) [M + H]− |
|---|---|---|---|---|
| P-0013 | 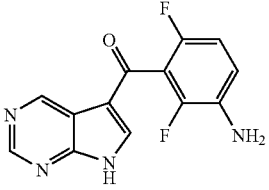 | 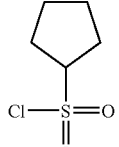 | 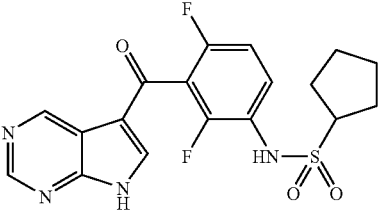 | 407.1 |
| P-0014 | 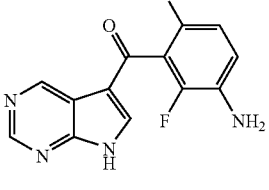 | 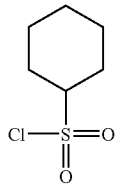 | 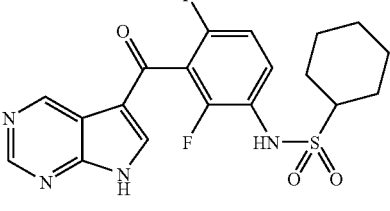 | 421.1 |
| P-0015 | 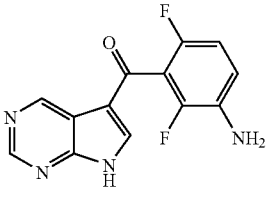 | 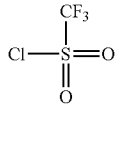 | 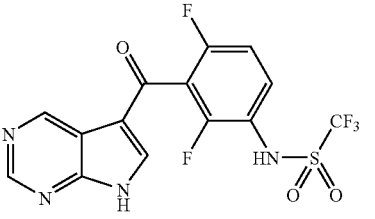 | 421.1 |
| P-0016 | 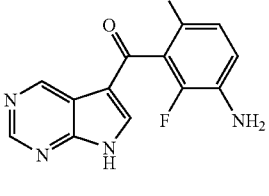 | 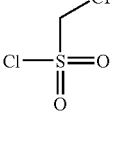 | 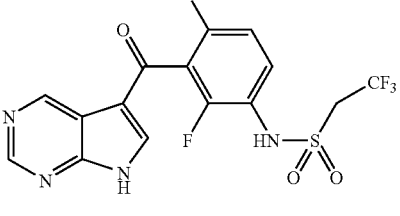 | 421.1 |
| P-0017 | 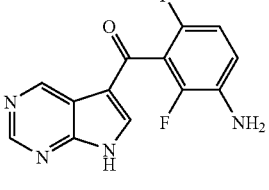 | 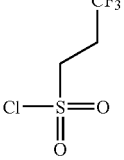 | 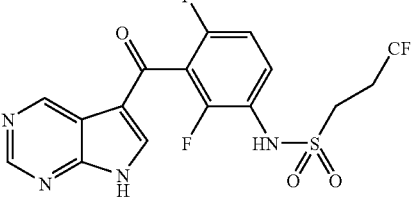 | 435.4 |
| P-0018 | 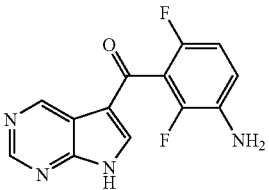 | 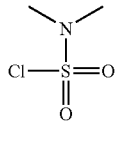 | 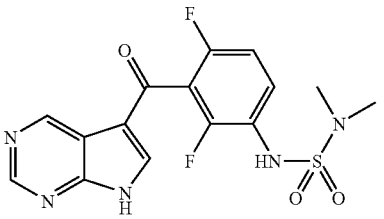 | 381.9 |

-continued
| Comp. number | 7H-pyrrolol[2,3-d]pyrimidine | XXXXIV | XXXXV | MS (ESI) [M + H]- |
|---|---|---|---|---|
| P-0019 | 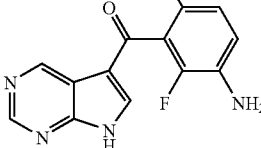 | 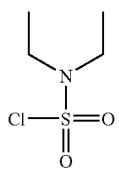 | 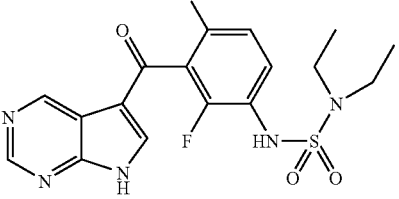 | |
| P-0020 | 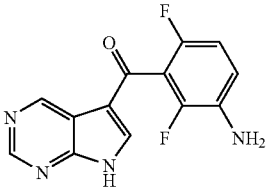 | 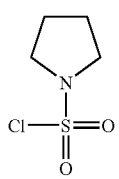 | 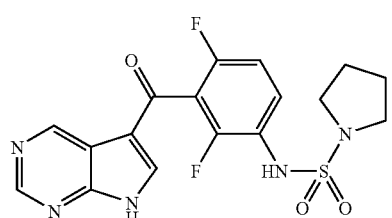 | 408.3 |
| P-0021 | 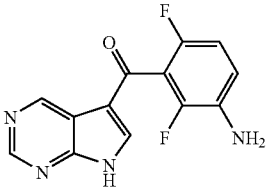 | 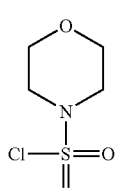 | 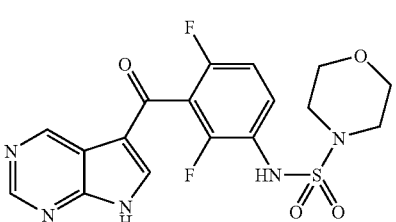 | 424.3 |
| P-0022 | 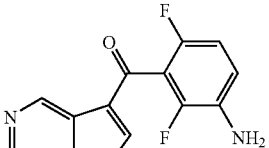 | 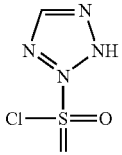 | 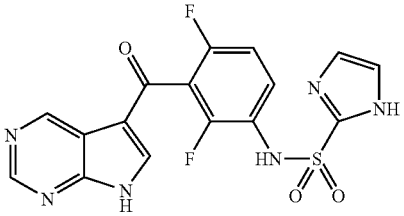 | |
| P-0023 | 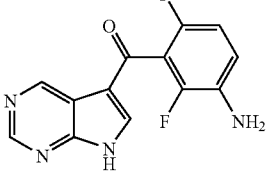 | 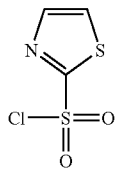 | 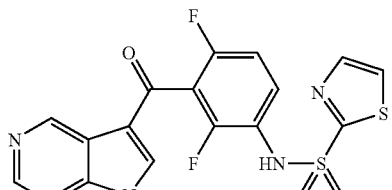 | |
| P-0024 | 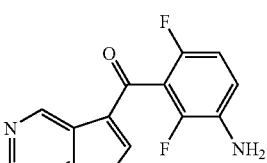 | 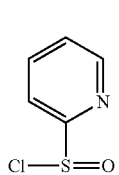 | 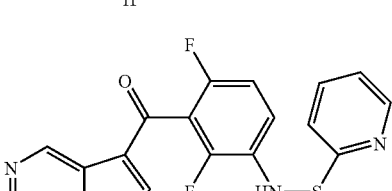 | 416.3 |
| P-0025 | 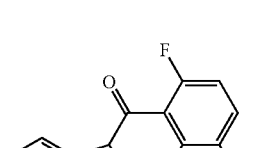 | 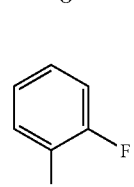 | 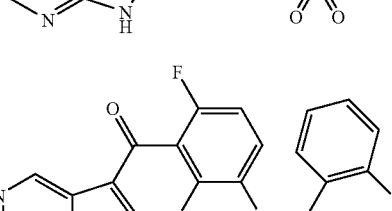 | 433.1 |

-continued
| Comp. number | 7H-pyrrolo[2,3-d]pyrimidine | XXXXIV | XXXXV | MS (ESI) [M + H]− |
|---|---|---|---|---|
| P-0026 | 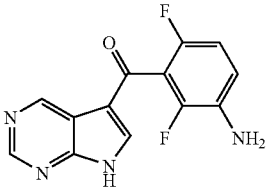 | 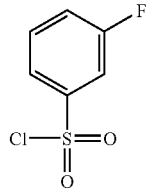 | 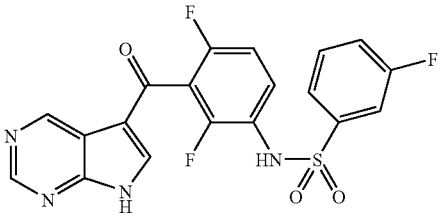 | 433.1 |
| P-0027 | 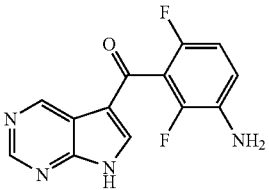 | 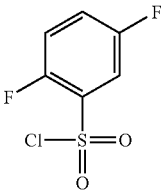 | 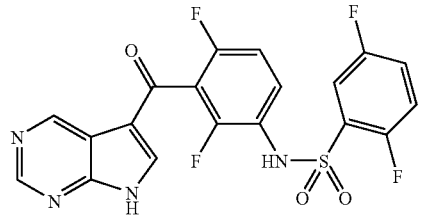 | 451.1 |
| P-0028 | 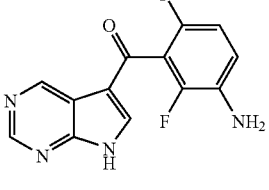 | 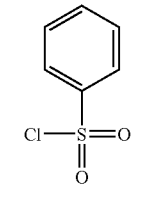 | 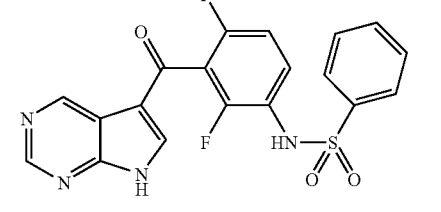 | 437.1 |
| P-0029 | 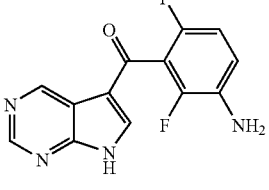 | 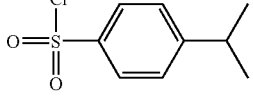 | 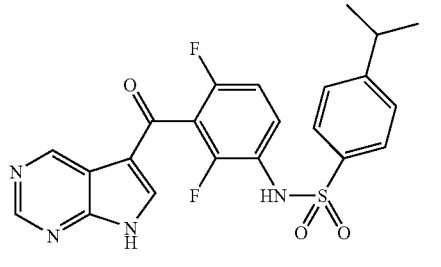 | 457.1 |
| P-0030 | 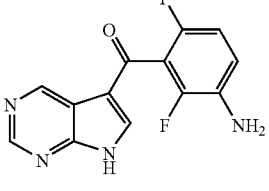 | 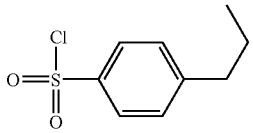 | 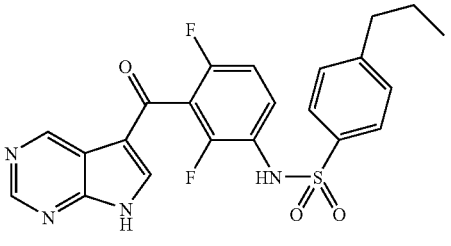 | 457.1 |
| P-0031 | 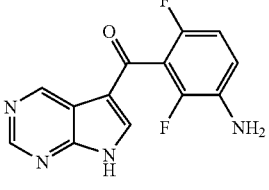 | 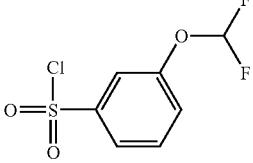 | 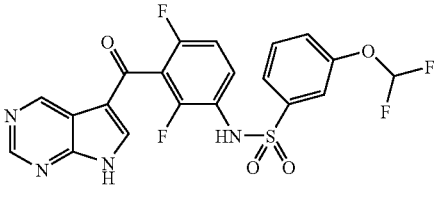 | 481.1 |

-continued
| Comp. number | 7H-pyrrolol[2,3-d]pyrimidine | XXXXIV | XXXXV | MS (ESI) [M + H]− |
|---|---|---|---|---|
| P-0032 | 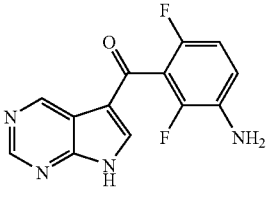 | 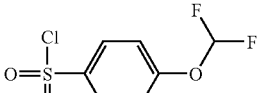 | 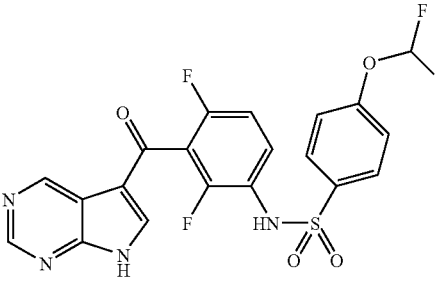 | 481.1 |
| P-0033 | 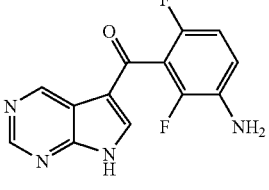 | 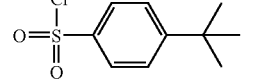 | 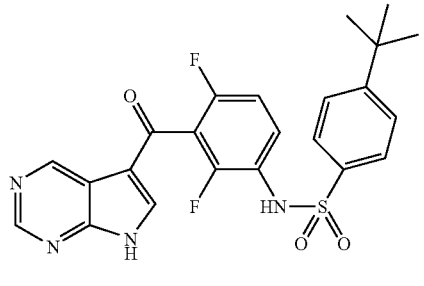 | 471.1 |
| P-0062 | 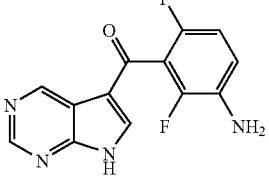 | 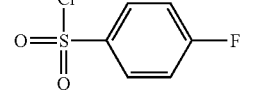 | 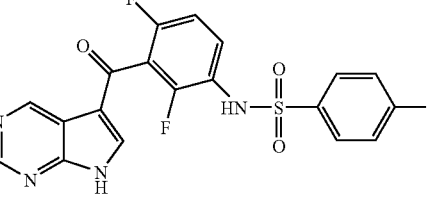 | 433.1 |
| P-0063 | 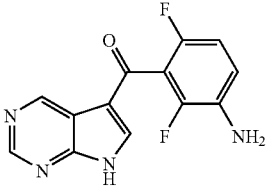 | 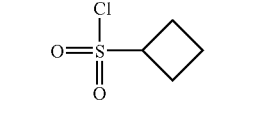 | 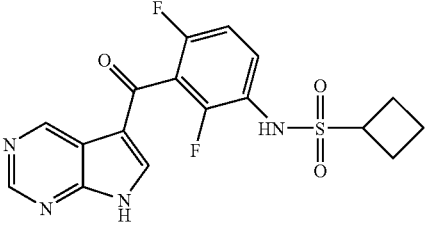 | 393.1 |
| P-0064 | 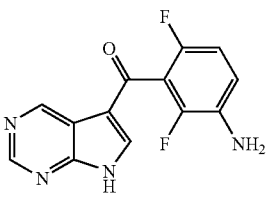 | 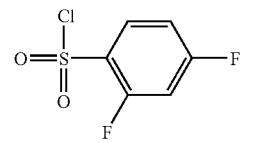 | 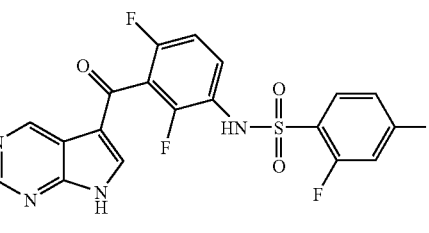 | 451.1 |
| P-0065 | 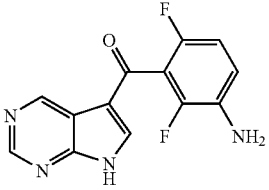 | 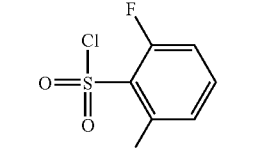 | 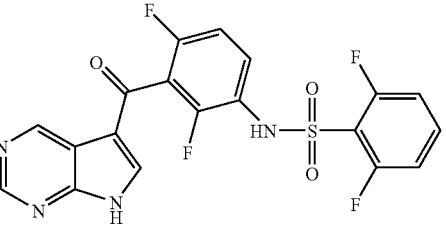 | 451.1 |

-continued
| Comp. number | 7H-pyrrolo[2,3-d]pyrimidine | XXXXIV | XXXXV | MS (ESI) [M + H]- |
|---|---|---|---|---|
| P-0066 | 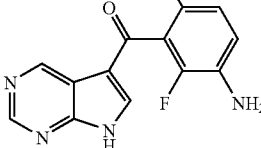 | 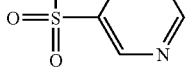 | 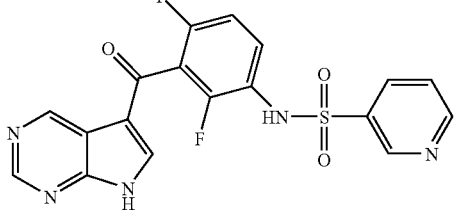 | 416.3 |
| P-0076 | 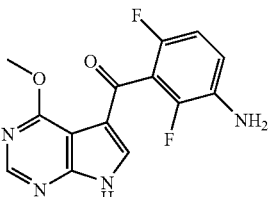 | 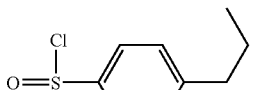 | 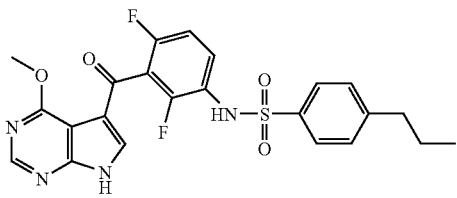 | |
| P-0077 | 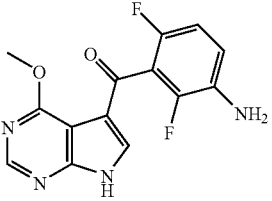 | 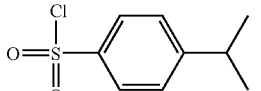 | 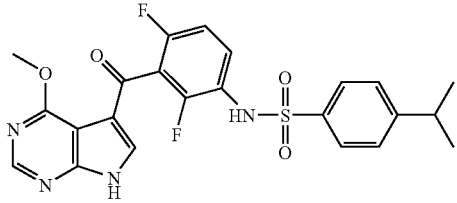 | |
| P-0078 | 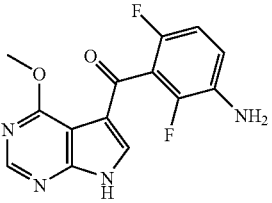 | 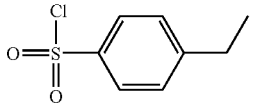 | 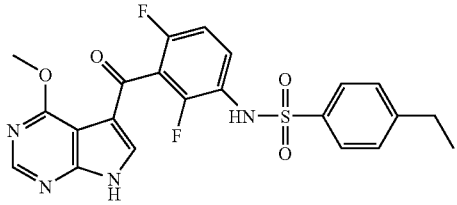 | |
| P-0079 | 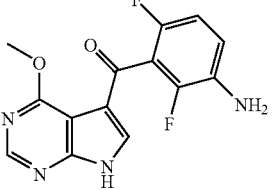 | 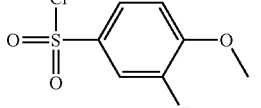 | 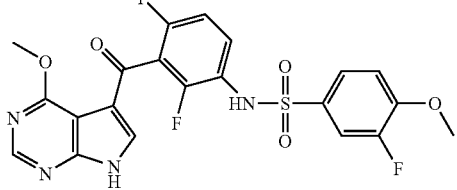 | |
| P-0080 | 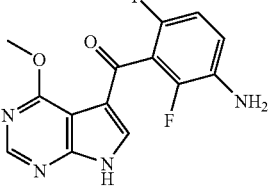 | 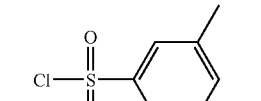 | 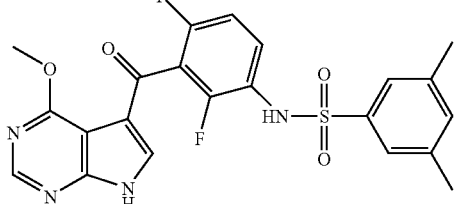 | |
| P-0081 | 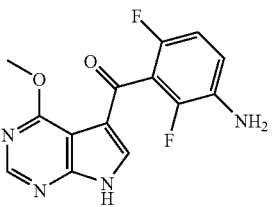 | 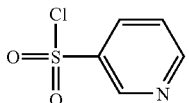 | 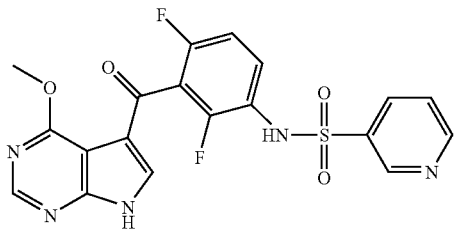 | |

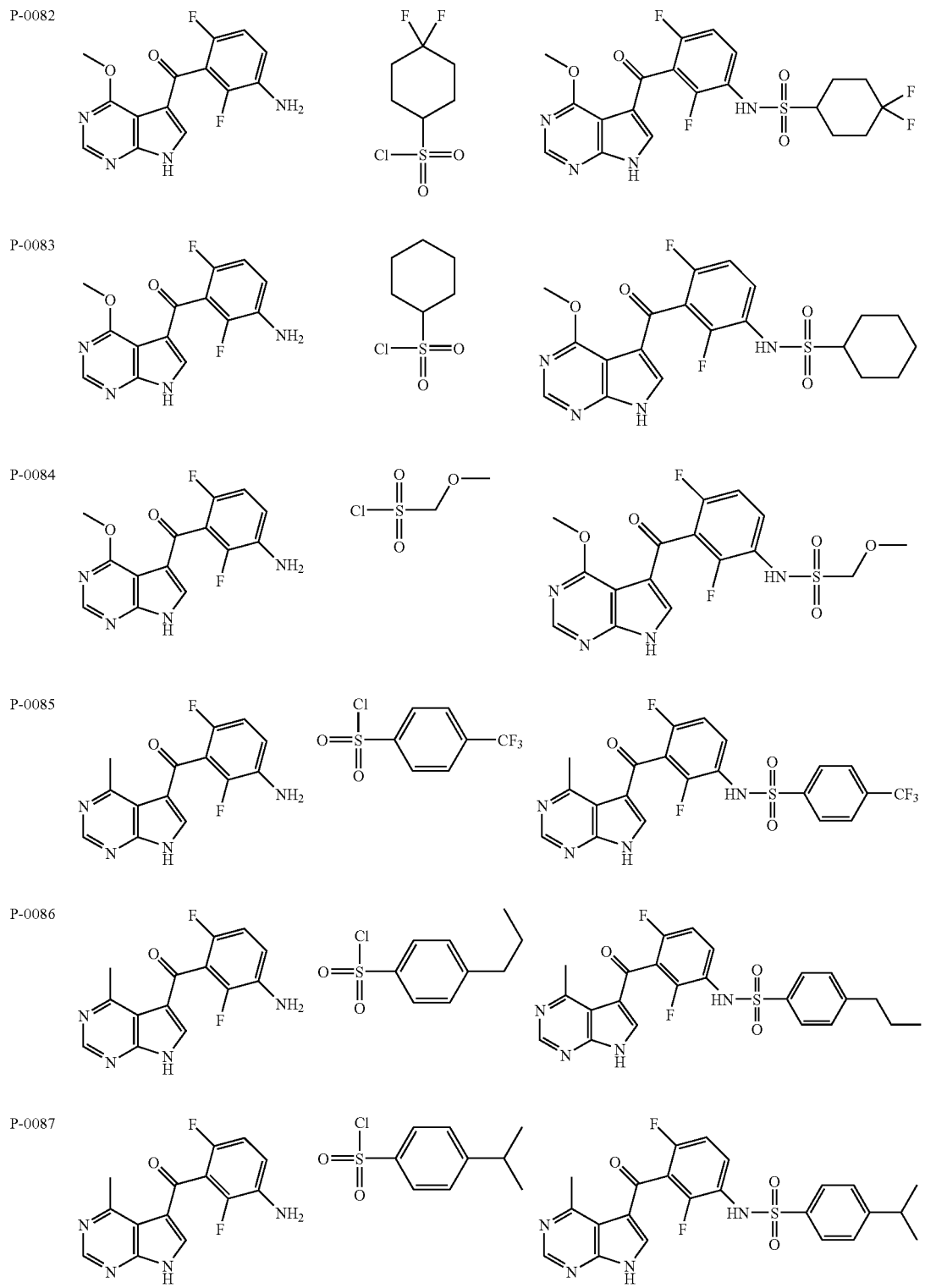

| Comp. number | 7H-pyrrolol[2,3-d]pyrimidine | XXXXIV | XXXXV | MS (ESI) [M + H]⁻ |
|---|---|---|---|---|
| P-0088 | 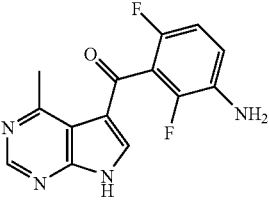 | 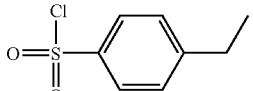 | 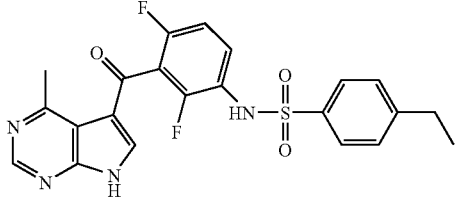 | |
| P-0089 | 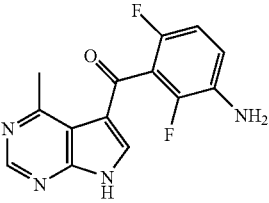 | 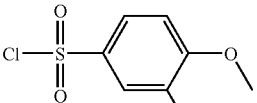 | 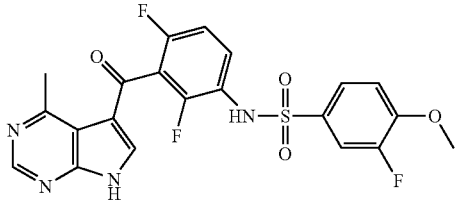 | |
| P-0090 | 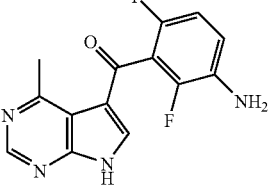 | 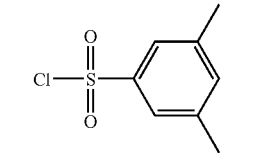 | 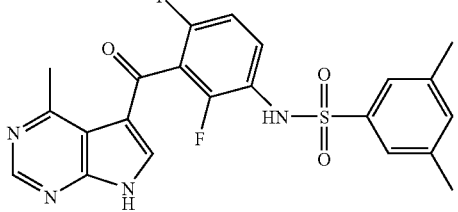 | |
| P-0091 | 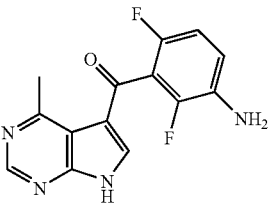 | 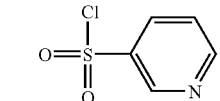 | 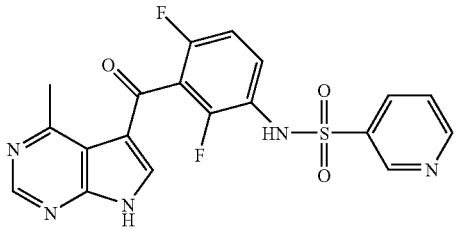 | |
| P-0092 | 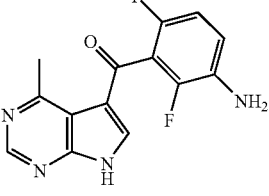 | 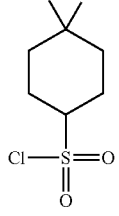 | 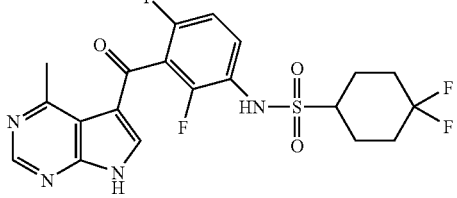 | |
| P-0093 | 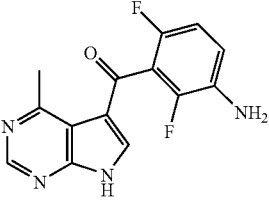 | 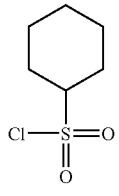 | 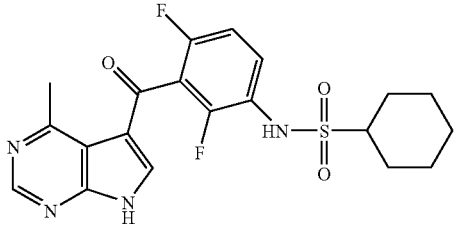 | |

| Comp. number | 7H-pyrrolol[2,3-d]pyrimidine | XXXXIV | XXXXV | MS (ESI) [M + H]− |
|---|---|---|---|---|
| P-0094 | 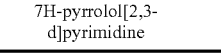 | 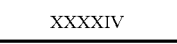 | 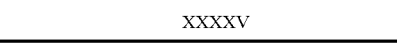 | |
Example 7
Synthesis of N-[2-fluoro-3-(7H-pyrrolo[2,3-d]pyrimidine-5-carbonyl)-phenyl]-4-trifluoromethyl-benzenesulfonamide P-0035
N-[2-Fluoro-3-(7H-pyrrolo[2,3-d]pyrimidine-5-carbonyl)-phenyl]-4-trifluoromethyl-benzenesulfonamide P-0035 was synthesized in seven steps from 2-fluoro-3-nitro-benzoic acid 28 as shown in Scheme 5.
Scheme 5
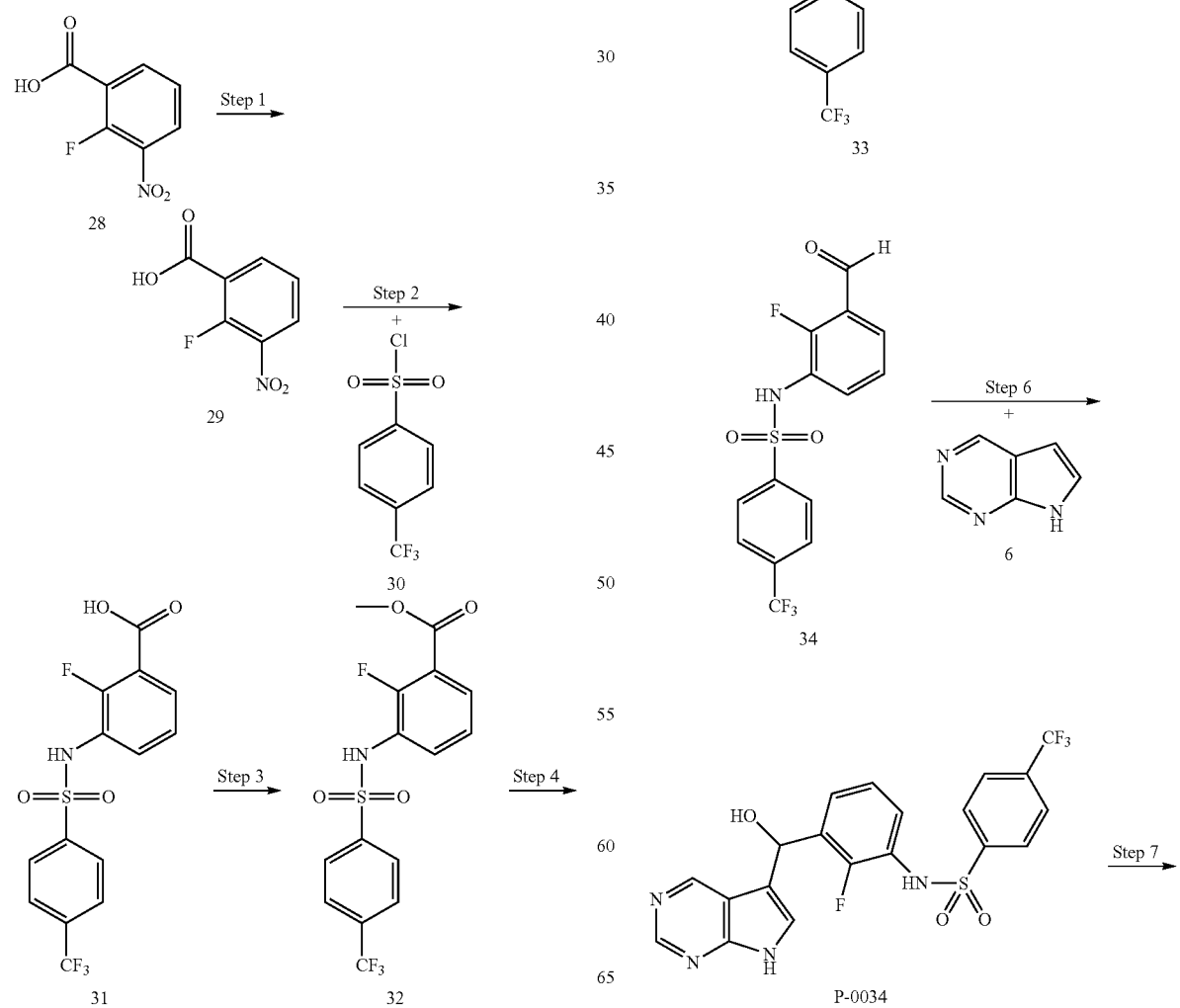

-continued

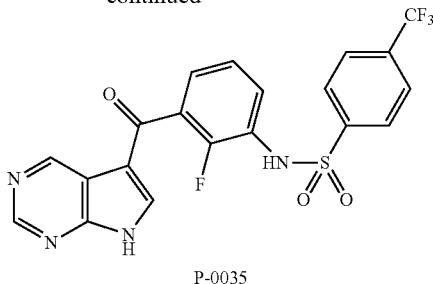

P-0035

Step 1—Preparation of 3-amino-2-fluoro-benzoic acid (29)

To 2-fluoro-3-nitro-benzoic acid (28, 2.0 g, 11 mmol) in 45 mL of tetrahydrofuran, 20% palladium hydroxide on carbon (150 mg) was added. The reaction was stirred under hydrogen for 2 hours, then filtered and the filtrate concentrated under vacuum to provide the desired compound 29 as a white solid, which was used in the next step without further purification. MS(ESI) [M–H$^+$]$^-$=154.4.

Step 2—Preparation of 2-fluoro-3-(4-trifluoromethyl-benzenesulfonylamino)-benzoic acid (31)

To 3-amino-2-fluoro-benzoic acid (29, 1.70 g, 11 mmol) in 34 mL of dichloromethane, pyridine (2.2 mL, 27 mmol) and 4-trifluoromethyl-benzenesulfonyl chloride (30, 6.7 g, 27 mmol) were added. The reaction was stirred at room temperature overnight, then poured into water, and extracted with ethyl acetate. The organic layer was washed with brine, dried over anhydrous sodium sulfate, filtered and the filtrate concentrated under vacuum to provide the desired compound 31 as a white solid, which was used in the next step without further purification.

Step 3—Preparation of 2-fluoro-3-(4-trifluoromethyl-benzenesulfonylamino)-benzoic acid methyl ester (32)

To 2-fluoro-3-(4-trifluoromethyl-benzenesulfonylamino)-benzoic acid (31, 4.0 g, 11 mmol) in 40 mL of methanol, sulfuric acid (8.8 mL, 0.16 mol) was added and the reaction mixture was refluxed overnight. The resulting reaction mixture was concentrated under vacuum, and the residue was combined with 5% aqueous sodium bicarbonate solution and extracted with ethyl acetate. The organic layer was washed with brine, dried over anhydrous sodium sulfate, and filtered. The filtrate was concentrated under vacuum and purified by silica gel column chromatography eluting with 20% ethyl acetate in hexane. Appropriate fractions were combined and concentrated under vacuum to provide the desired compound (32, 3.35 g, 81%). MS(ESI) [M–H$^+$]$^-$=376.4.

Step 4—Preparation of N-(2-fluoro-3-hydroxymethyl-phenyl)-4-trifluoromethyl-benzenesulfonamide (33)

To 2-fluoro-3-(4-trifluoromethyl-benzenesulfonylamino)-benzoic acid methyl ester (32, 3.34 g, 8.85 mmol) in 71 mL of tetrahydrofuran, lithium tetrahydroaluminate (17.7 mL, 1.00 M in tetrahydrofuran, 17.7 mmol) was added under an atmosphere of nitrogen at room temperature. The reaction was stirred at room temperature for 8 hours, followed by addition of 10 g of NaSO$_4$.10H$_2$O. After 12 hours, the reaction was filtered, the filtrate concentrated under vacuum and the residue was purified by silica gel column chromatography eluting with 40% ethyl acetate in hexane. Appropriate fractions were combined and concentrated under vacuum to provide the desired compound (33, 1.79 g, 58%). MS(ESI) [M–H$^+$]$^-$=348.4.

Step 5—Preparation of N-(2-fluoro-3-formyl-phenyl)-4-trifluoromethyl-benzenesulfonamide (34)

To N-(2-fluoro-3-hydroxymethyl-phenyl)-4-trifluoromethyl-benzenesulfonamide (33, 634 mg, 1.82 mmol) in 7 mL of tetrahydrofuran, Dess-Martin periodane (847 mg, 2.00 mmol) and sodium bicarbonate (2 g) were added. The reaction was stirred at room temperature for one hour, then poured into saturated aqueous sodium thiosulfate solution and extracted with ethyl acetate. The organic layer was washed with brine, dried over anhydrous sodium sulfate and filtered. The filtrate was concentrated under vacuum and the residue was purified by silica gel column chromatography eluting with 15% ethyl acetate in hexane. Appropriate fractions were combined and concentrated under vacuum to provide the desired compound (34, 607 mg, 96%). MS(ESI) [M–H$^+$]$^-$=346.4.

Step 6—Preparation of N-{2-fluoro-3-[hydroxy-(7H-pyrrolo[2,3-d]pyrimidin-5-yl)-methyl]-phenyl}-4-trifluoromethyl-benzenesulfonamide (P-0034)

To N-(2-fluoro-3-formyl-phenyl)-4-trifluoromethyl-benzenesulfonamide (34, 172 mg, 0.50 mmol) in 1 mL of methanol, 7H-pyrrolo[2,3-d]pyrimidine (6, 71 mg, 0.60 mmol) and potassium hydroxide (84 mg, 1.5 mmol) were added under an atmosphere of nitrogen. The reaction was stirred at room temperature for 24 hours, then poured into water and extracted with ethyl acetate. The organic layer was washed with brine, dried over sodium sulfate and filtered. The filtrate was concentrated under vacuum and the residue was purified by silica gel column chromatography eluting with 5% methanol in dichloromethane. Appropriate fractions were combined and concentrated under vacuum to provide the desired compound as a solid (P-0034, 101 mg, 44%). MS(ESI) [M+H$^+$]$^-$=467.8.

Step 7—Preparation of N-[2-fluoro-3-(7H-pyrrolo[2,3-d]pyrimidine-5-carbonyl)-phenyl]-4-trifluoromethyl-benzenesulfonamide (P-0035)

To N-{2-fluoro-3-[hydroxy-(7H-pyrrolo[2,3-d]pyrimidin-5-yl)-methyl]-phenyl}-trifluoromethyl-benzenesulfonamide (P-0034, 101 mg, 0.22 mmol) in 1 mL of tetrahydrofuran, Dess-Martin periodane (101 mg, 0.24 mmol) and sodium bicarbonate (200 mg) were added. The reaction was stirred at room temperature for one hour, then poured into saturated aqueous sodium thiosulfate solution and extracted with ethyl acetate. The organic layer was washed with brine, dried over anhydrous sodium sulfate and filtered. The filtrate was concentrated under vacuum and the residue was purified by silica gel column chromatography eluting with 70% ethyl acetate in hexane. Appropriate fractions were combined and concentrated under vacuum to provide the desired compound (P-0035, 72 mg, 72%). MS(ESI) [M–H$^+$]$^-$=463.4.

Example 8

Synthesis of ethanesulfonic acid [2-fluoro-3-(7H-pyrrolo[2,3-d]pyrimidine-5-carbonyl)-phenyl]-amide P-0036

Ethanesulfonic acid [2-fluoro-3-(7H-pyrrolo[2,3-d]pyrimidine-5-carbonyl)-phenyl]-amide P-0036 was synthesized in four steps from 5-iodo-7H-pyrrolo[2,3-d]pyrimidine 35 as shown in Scheme 6.

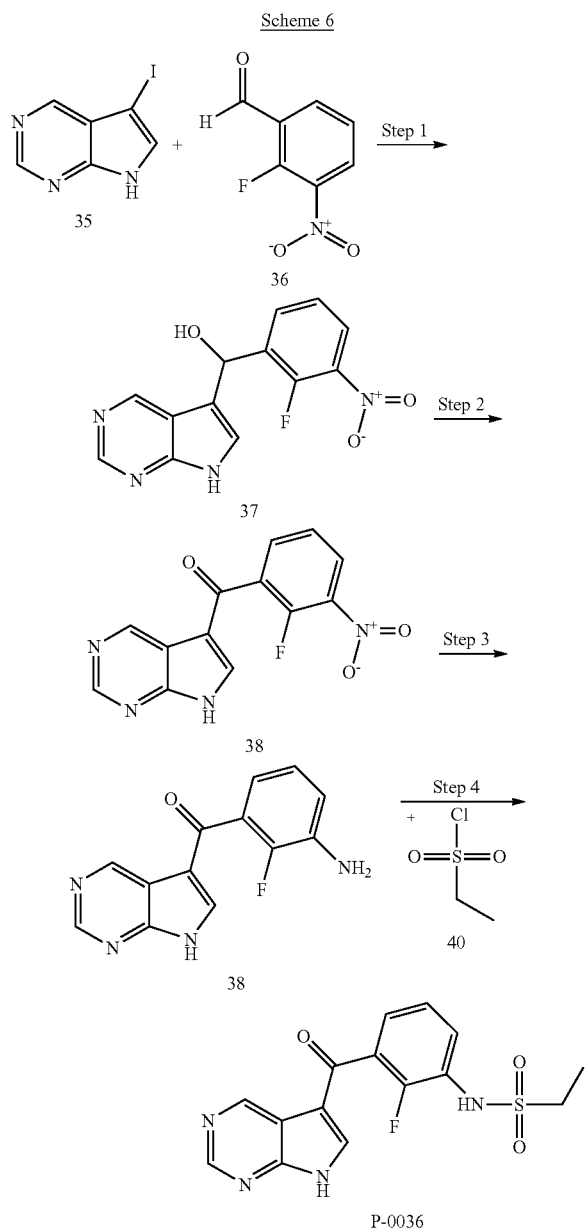

Scheme 6

Step 1—Preparation of (2-fluoro-3-nitro-phenyl)-(7H-pyrrolo[2,3-d]pyrimidin-5-yl)-methanol (37)

To 5-iodo-7H-pyrrolo[2,3-d]pyrimidine (35, 1.911 g, 7.799 mmol) 9.75 mL of tetrahydrofuran was added, the suspension was cooled to −5° C., and o-tolylmagnesium chloride (8.19 mL, 1.00 M in tetrahydrofuran, 8.19 mmol) was added. The reaction solution was stirred and kept between −5° C. and 0° C. for 30 minutes, then isopropylmagnesium chloride (4.29 mL, 2.0 M in tetrahydrofuran, 8.58 mmol) was slowly added dropwise. The reaction mixture was stirred and kept at 0° C. for 30 minutes, then 2-fluoro-3-nitro-benzaldehyde (36, 1.58 g, 9.36 mmol) in 4 mL of tetrahydrofuran was added dropwise using a syringe. The reaction mixture was stirred at −5° C. for 30 minutes and quenched with 1 N hydrochloric acid (1 equivalent) and extracted with ethyl acetate and saturated sodium bicarbonate in water. The organic layer was dried over magnesium sulfate, filtered and the filtrate concentrated under vacuum. The resulting material was purified by silica gel column chromatography eluting with a gradient of 60-80% ethyl acetate in hexanes (with 4% acetic acid). Appropriate fractions were combined and concentrated under vacuum to provide the desired compound (37, 699 mg). MS(ESI) [M+H$^+$]$^+$=289.4.

Step 2—Preparation of (2-fluoro-3-nitro-phenyl)-(7H-pyrrolo[2,3-d]pyrimidin-5-yl)-methanone (38)

To (2-fluoro-3-nitro-phenyl)-(7H-pyrrolo[2,3-d]pyrimidin-5-yl)-methanol (37, 0.699 g, 2.42 mmol), 52 mL of tetrahydrofuran was added, followed by sodium bicarbonate (2.04 g, 24.2 mmol) and Dess-Martin periodinane (1.03 g, 2.42 mmol). The reaction was allowed to stir at room temperature for 30 minutes and 25 mL of saturated sodium thiosulfate and 30 mL of water were added, followed by 50 mL of ethyl acetate. The organic layer was dried with magnesium sulfate, filtered, and the filtrate concentrated under vacuum. The resulting material was purified by silica gel column chromatography eluting with a gradient of 20-80% ethyl acetate in hexanes (with 4% acetic acid). Appropriate fractions were combined and concentrated under vacuum to provide the desired compound (38, 581 mg). MS (ESI) [M+H$^+$]$^+$=287.2.

Step 3—Preparation of (3-amino-2-fluoro-phenyl)-(7H-pyrrolo[2,3-d]pyrimidin-5-yl)-methanone (39)

To (2-fluoro-3-nitro-phenyl)-(7H-pyrrolo[2,3-d]pyrimidin-5-y)-methanone (38, 0.581 g, 2.03 mmol) in 20 mL of ethanol and 20 mL of tetrahydrofuran, stannous chloride dihydrate (1.58 g, 7.00 mmol) was added and the reaction placed in an oil bath at 60° C. After 2 hours, the reaction was poured into a beaker with 75 mL each of water and saturated sodium bicarbonate and 100 mL of ethyl acetate. The resulting milky suspension was treated with celite and the suspension was vacuum filtered through a thin pad of celite. The resulting clear layers of the filtrate were separated and the ethyl acetate layer was dried over anhydrous magnesium sulfate, filtered and the filtrate concentrated under vacuum. The residue was purified by silica gel column chromatography eluting with a gradient of 1-6% methanol in dichloromethane. Appropriate fractions were combined and concentrated under vacuum to provide the desired compound (39, 312 mg). MS (ESI) [M+H$^+$]$^+$=257.2.

Step 4—Preparation of ethanesulfonic acid [2-fluoro-3-7H-pyrrolo[2,3-d]pyrimidine-5-carbonyl)-phenyl]-amide (P-0036)

The (3-amino-2-fluoro-phenyl)-(7H-pyrrolo[2,3-d]pyrimidin-5-yl)-methanone (39, 20.0 mg, 0.078 mmol) is further reacted, for example, by adding 0.5 mL of tetrahydrofuran, 50 μL of pyridine, and an appropriate sulfonyl chloride (e.g. ethanesulfonyl chloride 40, 0.078 mmol). The reaction vial is allowed to stir at room temperature or in an oil bath at 60° C. After 1-3 days, the solvents are removed under vacuum, the residue dissolved in 0.5 mL dimethyl sulfoxide, and the material purified by C18 reversed phase HPLC, eluting with 20-100% acetonitrile (with 0.1% trifluoroacetic acid) in water (with 0.1% trifluoroacetic acid) at a flow rate of 20 mL/min. Ethanesulfonic acid [2-fluoro-3-(7H-pyrrolo[2,3-d]pyrimidine-5-carbonyl)-phenyl]-amide (P-0036) was prepared by this protocol using ethanesulfonyl chloride 40 in step 4. MS (ESI) [M+H$^+$]$^+$=349.1.

Additional compounds were prepared similarly to the protocol of Scheme 6, where optimal reaction conditions may have varied, for example, in terms of any of time and temperature of the reaction, work up conditions, and chromatography conditions for purification of the desired compounds. The reactions were performed substituting ethanesulfonyl chloride 40 with an appropriate sulfonyl chloride in step 4. The following compounds were prepared by this procedure:

4-Fluoro-N-[2-fluoro-3-(7H-pyrrolo[2,3-d]pyrimidine-5-carbonyl)-phenyl]-benzenesulfonamide (P-0037),
2,2,2-Trifluoro-ethanesulfonic acid [2-fluoro-3-(7H-pyrrolo[2,3-d]pyrimidine-5-carbonyl)-phenyl]-amide (P-0038),
Pyridine-3-sulfonic acid [2-fluoro-3-(7H-pyrrolo[2,3-d]pyrimidine-5-carbonyl)-phenyl]-amide (P-0039),
2,5-Difluoro-N-[2-fluoro-3-(7H-pyrrolo[2,3-d]pyrimidine-5-carbonyl)-phenyl]-benzenesulfonamide (P-0040),
2,6-Difluoro-N-[2-fluoro-3-(7H-pyrrolo[2,3-d]pyrimidine-5-carbonyl)-phenyl]-benzenesulfonamide (P-0041),
2,4-Difluoro-N-[2-fluoro-3-(7H-pyrrolo[2,3-d]pyrimidine-5-carbonyl)-phenyl]-benzenesulfonamide (P-0042),
Propane-2-sulfonic acid [2-fluoro-3-(7H-pyrrolo[2,3-d]pyrimidine-5-carbonyl)-phenyl]-amide (P-0043),
3-Fluoro-N-[2-fluoro-3-(7H-pyrrolo[2,3-d]pyrimidine-5-carbonyl)-phenyl]-benzenesulfonamide (P-0044),
N,N-Dimethylamino-sulfonic acid [2-fluoro-3-(7H-pyrrolo[2,3-d]pyrimidine-5-carbonyl)-phenyl]-amide (P-0045),
Pyrrolidine-1-sulfonic acid [2-fluoro-3-(7H-pyrrolo[2,3-d]pyrimidine-5-carbonyl)-phenyl]-amide (P-0046),
2-Methyl-propane-1-sulfonic acid [2-fluoro-3-(7H-pyrrolo[2,3-d]pyrimidine-5-carbonyl)-phenyl]-amide (P-0047),
Butane-2-sulfonic acid [2-fluoro-3-(7H-pyrrolo[2,3-d]pyrimidine-5-carbonyl)-phenyl]-amide (P-0048),
Cyclobutanesulfonic acid [2-fluoro-3-(7H-pyrrolo[2,3-d]pyrimidine-5-carbonyl)-phenyl]-amide (P-0049),
Morpholine-4-sulfonic acid [2-fluoro-3-(7H-pyrrolo[2,3-d]pyrimidine-5-carbonyl)-phenyl]-amide (P-0050),
2-Fluoro-N-[2-fluoro-3-(7H-pyrrolo[2,3-d]pyrimidine-5-carbonyl)-phenyl]-benzenesulfonamide (P-0051),
Cyclohexanesulfonic acid [2-fluoro-3-(7H-pyrrolo[2,3-d]pyrimidine-5-carbonyl)-phenyl]-amide (P-0052),
Cyclopentanesulfonic acid [2-fluoro-3-(7H-pyrrolo[2,3-d]pyrimidine-5-carbonyl)-phenyl]-amide (P-0053), and
Pentane-2-sulfonic acid [2-fluoro-3-(7H-pyrrolo[2,3-d]pyrimidine-5-carbonyl)-phenyl]-amide (P-0054).

The following table indicates the sulfonyl chloride (column 2) used to afford the desired compound (column 3). The compound number is provided in column 1, and the observed mass is in column 4.

| Compound number | Sulfonyl chloride | Compound | MS (ESI) [M + H]$^-$ |
|---|---|---|---|
| P-0037 | | | 415.1 |
| P-0038 | | | 403.1 |
| P-0039 | | | 397.9 |

-continued

| Compound number | Sulfonyl chloride | Compound | MS (ESI) [M + H]− |
|---|---|---|---|
| P-0040 | 2,5-difluorobenzenesulfonyl chloride | pyrrolo[2,3-d]pyrimidine-benzoyl-fluorophenyl-2,5-difluorobenzenesulfonamide | 433.1 |
| P-0041 | 2,6-difluorobenzenesulfonyl chloride | pyrrolo[2,3-d]pyrimidine-benzoyl-fluorophenyl-2,6-difluorobenzenesulfonamide | 433.1 |
| P-0042 | 2,4-difluorobenzenesulfonyl chloride | pyrrolo[2,3-d]pyrimidine-benzoyl-fluorophenyl-2,4-difluorobenzenesulfonamide | 433.1 |
| P-0043 | isopropylsulfonyl chloride | pyrrolo[2,3-d]pyrimidine-benzoyl-fluorophenyl-isopropylsulfonamide | 363.5 |
| P-0044 | 3-fluorobenzenesulfonyl chloride | pyrrolo[2,3-d]pyrimidine-benzoyl-fluorophenyl-3-fluorobenzenesulfonamide | 415.1 |
| P-0045 | dimethylsulfamoyl chloride | pyrrolo[2,3-d]pyrimidine-benzoyl-fluorophenyl-dimethylsulfamide | 364.3 |
| P-0046 | pyrrolidine-1-sulfonyl chloride | pyrrolo[2,3-d]pyrimidine-benzoyl-fluorophenyl-pyrrolidine-1-sulfonamide | 390.3 |

-continued

| Compound number | Sulfonyl chloride | Compound | MS (ESI) [M + H]⁻ |
|---|---|---|---|
| P-0047 | | | 377.1 |
| P-0048 | | | 377.1 |
| P-0049 | | | 375.1 |
| P-0050 | | | 406.3 |
| P-0051 | | | 415.1 |
| P-0052 | | | 403.1 |
| P-0053 | | | 389.1 |

| Compound number | Sulfonyl chloride | Compound | MS (ESI) [M + H]⁻ |
|---|---|---|---|
| P-0054 | | | 391.1 |

Example 9

Synthesis of propane-1-sulfonic acid [2,4-difluoro-3-(4-methyl-7H-pyrrolo[2,3-d]pyrimidine-5-carbonyl)-phenyl]-amide P-0056

Propane-1-sulfonic acid [2,4-difluoro-3-(4-methyl-7H-pyrrolo[2,3-d]pyrimidine-5-carbonyl)-phenyl]-amide P-0056 was synthesized in three steps from 4-chloro-7H-pyrrolo[2,3-d]pyrimidine 1 as shown in Scheme 7.

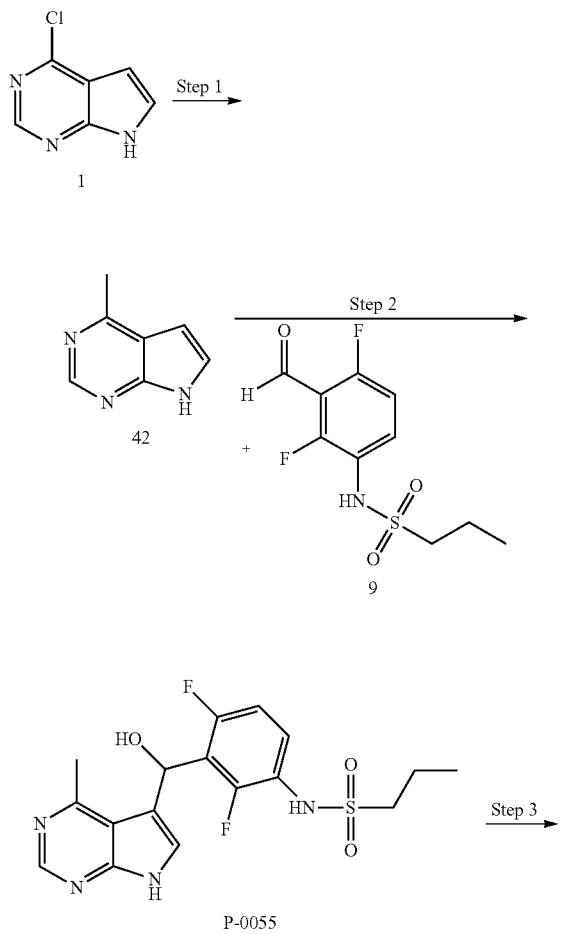

Scheme 7

-continued

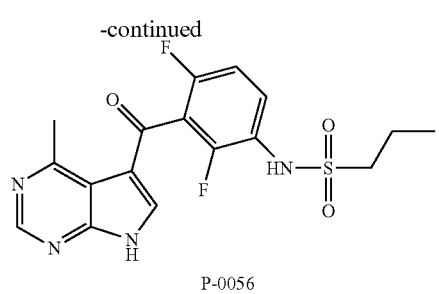

P-0056

Step 1—Preparation of 4-methyl-7H-pyrrolo[2,3-d]pyrimidine (42)

Into a round bottom flask the catalyst PdCl₂(dppf), under an atmosphere of nitrogen, was placed with 15 mL of toluene along with a stir bar. A suspension of 4-chloro-7H-pyrrolo[2,3-d]pyrimidine (1, 1.47 g, 9.57 mmol) in 15 mL of toluene was added at room temperature. After stirring for 10 minutes, methylmagnesium bromide (17.00 mL, 3.00 M in ether, 51.00 mmol) was added dropwise. The solution turned from orange to yellow, and was slowly heated to 60° C. and stirred for 3 hrs at 60° C. and then overnight at room temperature. The resulting dark orange reaction mixture was quenched with 1 N hydrochloric acid and adjusted to pH ~5, then extracted with ethyl acetate and water saturated with sodium chloride. The organic layer was washed with water and brine, dried over magnesium sulfate, filtered and the filtrate concentrated under vacuum. The resulting material was purified by silica gel column chromatography eluting with ethyl acetate and hexane. Appropriate fractions were combined and concentrated under vacuum to provide the desired compound as a yellow solid (42, 202 mg). ¹H-NMR(dmso-d6) was consistent with the desired compound. MS(ESI) [M+H⁺]⁺=134.3.

Step 2—Preparation of propane-1-sulfonic acid {2,4-difluoro-3-[hydroxy-(4-methyl-7H-pyrrolo[2,3-d]pyrimidin-5-yl)-methyl]-phenyl}-amide (P-0055)

To 4-methyl-7H-pyrrolo[2,3-d]pyrimidine (42, 0.192 g, 1.44 mmol), propane-1-sulfonic acid (2,4-difluoro-3-formyl-phenyl)-amide (9, 0.456 g, 1.73 mmol), potassium hydroxide (0.263 g, 4.69 mmol) and 1.0 mL of methanol were added to provide a solution. The reaction was allowed to stir at room temperature for 30 hours, then quenched with water and adjusted to pH ~5 with acetic acid and sodium bicarbonate and extracted with ethyl acetate and saturated sodium chloride. The organic layer was washed with water and brine, dried with magnesium sulfate, filtered and the filtrate concentrated under vacuum. The resulting material was purified by silica gel column chromatography eluting with ethyl acetate and hexane with 4% acetic acid. Appropriate fractions were combined and concentrated under vacuum to provide the desired compound as an off-white solid (P-0055, 215 mg). $^1$H-NMR(dmso-d6) showed it contains about >80% of the desired compound, used in the next step without further purification. MS(ESI) [M+H$^-$]$^+$=397.1.

Step 3—Preparation of propane-1-sulfonic acid [2,4-difluoro-3-(4-methyl-7H-pyrrolo[2,3-d]pyrimidine-5-carbonyl)-phenyl]-amide (P-0056)

Propane-1-sulfonic acid {2,4-difluoro-3-[hydroxy-(4-methyl-7H-pyrrolo[2,3-d]pyrimidin-5-yl)-methyl]-phenyl}-amide (P-0055, 0.215 g, 0.542 mmol) was dissolved in 40 mL of tetrahydrofuran and Dess-Martin periodinane (0.253 g, 0.597 mmol) was added. The resulting mixture was stirred at room temperature for 30 minutes. The reaction mixture was diluted with ethyl acetate and a mixture of 20 mL of saturated aqueous sodium bicarbonate and 4 mL of saturated aqueous sodium thiosulfate was added. The mixture was vigorously stirred until the organic layer turned clear. The aqueous layer was separated and extracted once with ethyl acetate. The combined organic layers were washed with water and brine, dried with magnesium sulfate, filtered and the filtrate concentrated under vacuum. The residue was suspended in tetrahydrofuran and acetonitrile and sonicated for 15 minutes. The solid material was collected with filtration to provide the desired compound as a white solid (P-0056, 67 mg). LC-MS showed one major peak with 99.7% purity and $^1$H-NMR (dmso-d6) was consistent with the desired compound. MS(ESI) [M+H$^+$]$^+$=395.0. The filtrate was recovered and purified by silica gel column chromatography eluting with ethyl acetate and hexane. Appropriate fractions were combined and concentrated under vacuum to provide the desired compound as an off-white solid (P40056, 51 mg). LC-MS showed one major peak with 99.8% purity. $^1$H-NMR(dmso-d6) was consistent with the desired compound. MS(ESI) [M+H$^+$]$^+$=395.0.

N-[2,4-Difluoro-3-(4-methoxy-7H-pyrrolo[2,3-d]pyrimidine-5-carbonyl)-phenyl]-benzenesulfonamide P-0072 and propane-1-sulfonic acid [3-(4-ethoxy-7H-pyrrolo[2,3-d]pyrimidine-5-carbonyl)-2,4-difluoro-phenyl]-amide P-0075

P-0072

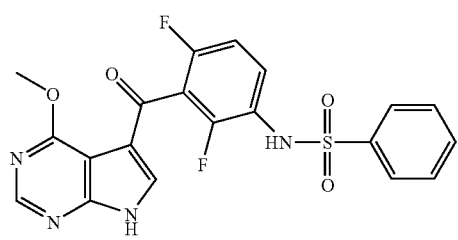

and
P-0075

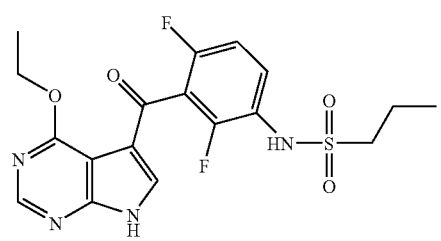

were prepared similarly to the protocol of Scheme 7, steps 2 and 3, replacing 4-methyl-7H-pyrrolo[2,3-d]pyrimidine 42 with 4-methoxy-7H-pyrrolo[2,3-d]pyrimidine 3 and propane-1-sulfonic acid (2,4-difluoro-3-formyl-phenyl)-amide 9 with N-(2,4-Difluoro-3-formyl-phenyl)-benzenesulfonamide in step 2 for P-0072 and replacing 4-methyl-7H-pyrrolo [2,3-d]pyrimidine 42 with 4-ethoxy-7H-pyrrolo[2,3-d]pyrimidine 47 in step 2 for P-0075. Alternatively, the intermediate in the reaction to form P-0072 was reduced using triethylsilane and trifluoroacetic acid to form N-[2,4-difluoro-3-(4-methoxy-7H-pyrrolo[2,3-d]pyrimidin-5-ylmethyl)-phenyl]-benzenesulfonamide P-0073

P-0073

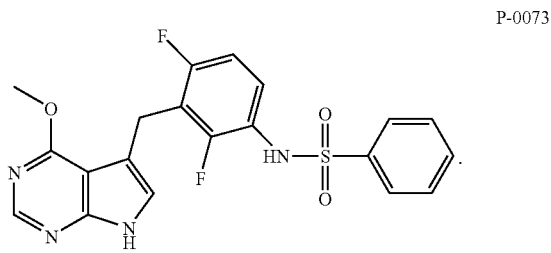

4-ethoxy-7H-pyrrolo[2,3-d]pyrimidine 47 was prepared in one step from 4-chloro-7H-pyrrolo[2,3-d]pyrimidine 1 as shown in scheme 7a.

Scheme 7a

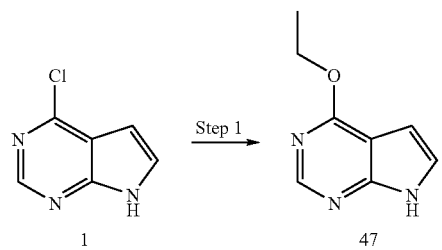

To 4-chloro-7H-pyrrolo[2,3-d]pyrimidine (1, 300 mg, 1.95 mmol) in 3.0 mL of ethanol, potassium hydroxide (226 mg, 4.03 mmol) was added and the reaction was microwaved at 120° C. for 3 hours. The reaction was extracted in ethyl acetate and aqueous saturated ammonium chloride. The organic layer was separated and washed with brine, then dried over magnesium sulfate, filtered and the filtrate concentrated under vacuum. The resulting material was recrystallized with methanol to provide the desired compound (47, 213 mg). MS (ESI) [M+H$^+$]$^+$=164.9.

Example 10

Synthesis of propane-1-sulfonic acid [2,4-difluoro-3-(4-methoxy-7H-pyrrolo[2,3-d]pyrimidine-5-carbonyl)-phenyl]-amide P-0058

Propane-1-sulfonic acid [2,4-difluoro-3-(4-methoxy-7H-pyrrolo[2,3-d]pyrimidine-5-carbonyl)-phenyl]-amide P-0058 was synthesized in two steps from 4-chloro-7H-pyrrolo[2,3-d]pyrimidine 1 as shown in Scheme 8.

Scheme 8

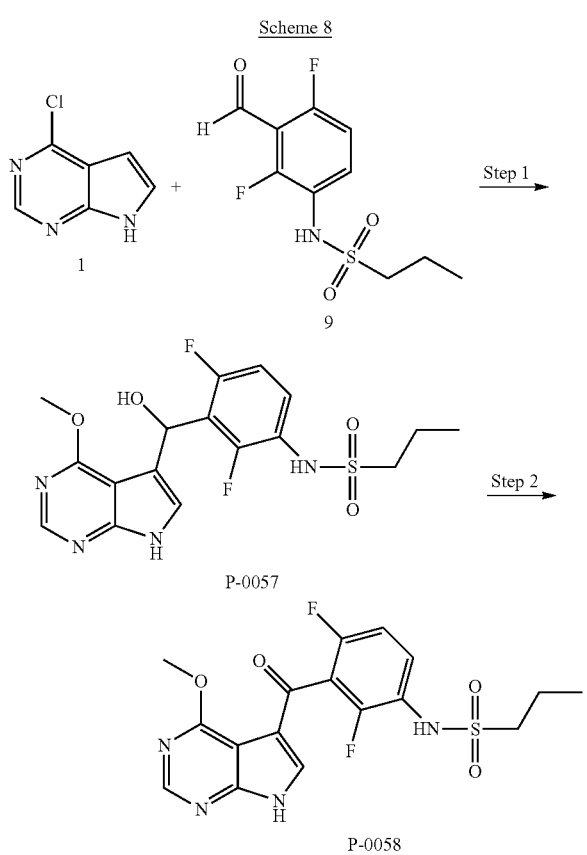

Step 1—Preparation of propane-1-sulfonic acid {2,4-difluoro-3-[hydroxy-(4-methoxy-7H-pyrrolo[2,3-d]pyrimidin-5-yl)-methyl]-phenyl}-amide (P-0057)

To 4-chloro-7H-pyrrolo[2,3-d]pyrimidine (1, 0.200 g, 1.30 mmol) and propane-1-sulfonic acid (2,4-difluoro-3-formyl-phenyl)-amide (9, 0.401 g, 1.52 mmol), 3.83 mL of methanol was added and this suspension was allowed to stir for 10 minutes, followed by the addition of potassium hydroxide (0.238 g, 4.24 mmol). The reaction was allowed to stir at room temperature over the weekend. The reaction was poured into 25 mL of 1N hydrochloric acid and 25 mL of ethyl acetate. The organic layer was dried over anhydrous magnesium sulfate, filtered and the filtrate concentrated under vacuum. The resulting residue was purified by silica gel column chromatography eluting with a gradient of 20-100% ethyl acetate in hexanes. Appropriate fractions were combined and concentrated under vacuum to provide the desired compound (P-0057, 176 mg). $^1$N NMR was consistent with the compound structure. MS(ESI) [M+H$^+$]$^-$=413.1.

Step 2—Preparation of propane-1-sulfonic acid [2,4-difluoro-3-(4-methoxy-7H-pyrrolo[2,3-d]pyrimidine-5-carbonyl)-phenyl]-amide (P-0058)

To propane-1-sulfonic acid {2,4-difluoro-3-[hydroxy-(4-methoxy-7H-pyrrolo[2,3-d]pyrimidin-5-yl)-methyl]-phenyl}-amide (P-0057, 0.176 g, 0.427 mmol), 9.2 mL of tetrahydrofuran was added followed by sodium bicarbonate (0.358 g, 4.27 mmol) and Dess-Martin periodinane (0.181 g, 0.427 mmol). The reaction was allowed to stir at room temperature for 30 minutes, then 25 mL of saturated sodium thiosulfate and 30 mL of water were added followed by 50 mL of ethyl acetate. The organic layer was dried with magnesium sulfate, filtered, and the filtrate concentrated under vacuum. The resulting residue was purified by silica gel column chromatography eluting with a gradient of 20-60% ethyl acetate in hexanes. Appropriate fractions were combined and concentrated under vacuum to provide the desired compound (P-0058, 146 mg). $^1$H NMR was consistent with the compound structure. MS(ESI) [M+H$^+$]$^-$=411.1.

Additional compounds were prepared similarly to the protocol of Scheme 8, where optimal reaction conditions may have varied, for example, in terms of any of time and temperature of the reaction, work up conditions, and chromatography conditions for purification of the desired compounds. Propane-1-sulfonic acid [2-fluoro-3-(4-methoxy-7H-pyrrolo[2,3-d]pyrimidine-5-carbonyl)-phenyl]-amide P-0060. N-[2-fluoro-3-(4-methoxy-7H-pyrrolo[2,3-d]pyrimidine-5-carbonyl)-phenyl]-4-trifluoromethyl-benzenesulfonamide P-0059, and N-[2,4-difluoro-3-(4-methoxy-7H-pyrrolo[2,3-d]pyrimidine-5-carbonyl)-phenyl]-4-trifluoromethyl-benzenesulfonamide P-0061,

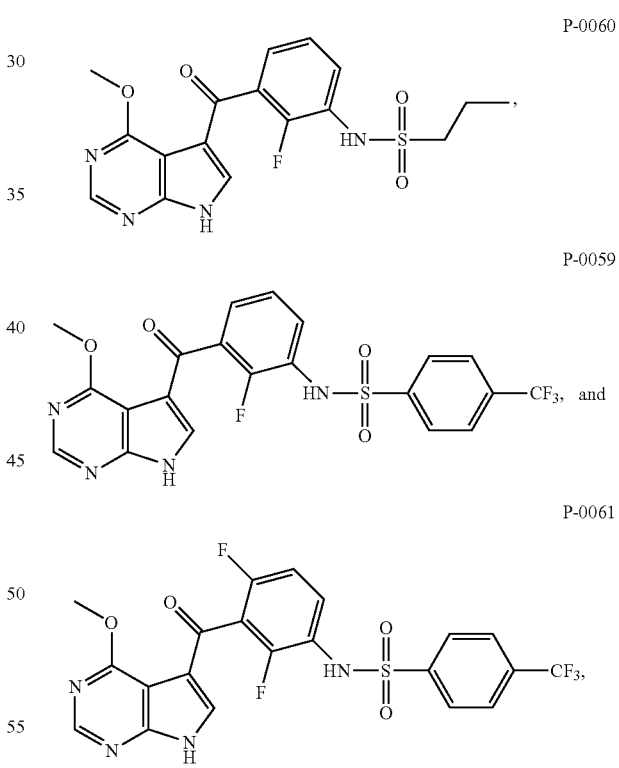

were prepared by replacing propane-1-sulfonic acid (2,4-difluoro-3-formyl-phenyl)-amide 9 with propane-1-sulfonic acid (2-fluoro-3-formyl-phenyl)-amide 18, N-(2-fluoro-3-formyl-phenyl)-4-trifluoromethyl-benzenesulfonamide 34, and N-(2,4-difluoro-3-formyl-phenyl)-4-trifluoromethyl-benzenesulfonamide 10, respectively, in Step 1. MS(ESI) [M+H$^-$]$^-$=391.4 (P-0060), MS(ESI) [M+H$^+$]$^+$=495.3 (P-0059), and 513.0 (P-0061).

Example 11

Synthesis of N-[3-(4-cyclopropyl-7H-pyrrolo[2,3-d]pyrimidine-5-carbonyl)-2,4-difluoro-phenyl]-4-trifluoromethyl-benzenesulfonamide P-0068

N-[3-(4-Cyclopropyl-7H-pyrrolo[2,3-d]pyrimidine-5-carbonyl)-2,4-difluoro-phenyl]-4-trifluoromethyl-benzenesulfonamide P-0068 was synthesized in three steps from 4-chloro-7H-pyrrolo[2,3-d]pyrimidine 1 as shown in Scheme 9.

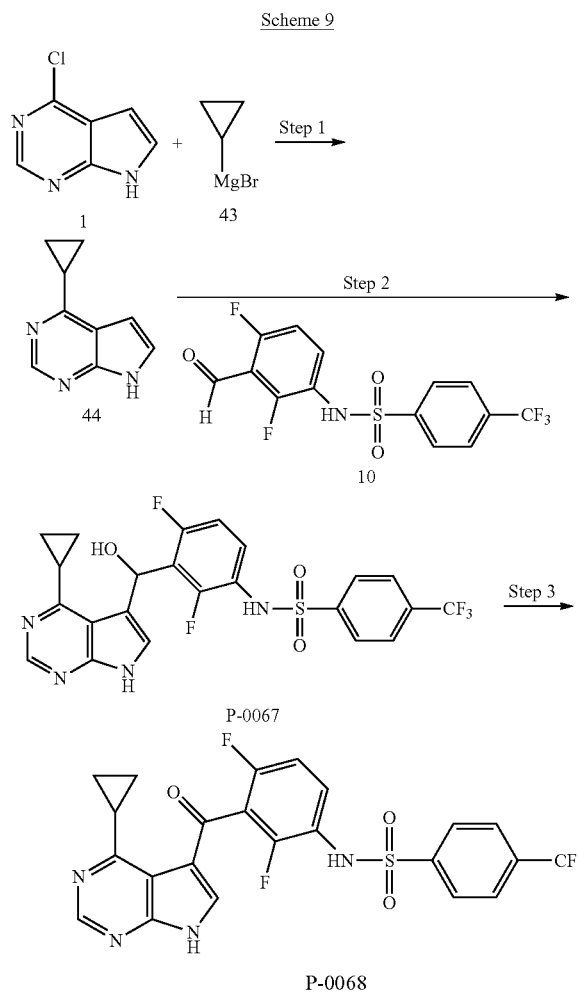

Step 1—Preparation of 4-cyclopropyl-7H-pyrrolo[2,3-d]pyrimidine (44)

4-chloro-7H-pyrrolo[2,3-d]pyrimidine (1, 0.452 g, 2.94 mmol), cyclopropylmagnesium bromide (43, 31.4 mL, 0.50 M in tetrahydrofuran, 15.7 mmol), and [1,1'-bis(diphenylphosphino)ferrocene]dichloropalladium(II) (0.240 g, complex 1:1 with dichloromethane, 0.294 mmol) were mixed with 15.4 mL of toluene. The reaction was heated at 60° C. overnight, then quenched with 1 M aqueous hydrochoric acid to pH 4 and filtered through a bed of celite. The layers of the filtrate were separated and the aqueous layer extracted with ethyl acetate: The combined organic layers were washed with brine, dried over sodium sulfate, filtered and the filtrate concentrated under vacuum. The resulting material was purified by silica gel column chromatography, eluting with ethyl acetate and hexane. Appropriate fractions were combined and concentrated under vacuum to provide the desired compound (44, 0.465 g). MS (ESI) [M+H$^+$]$^+$=160.1.

Step 2—Preparation of N-{3-[(4-cyclopropyl-7H-pyrrolo[2,3-d]pyrimidin-5-yl)-hydroxy-methyl]-2,4-difluoro-phenyl}-4-trifluoromethyl-benzenesulfonamide (P-0067)

4-cyclopropyl-7H-pyrrolo[2,3-d]pyrimidine (44) was reacted with N-(2,4-difluoro-3-formyl-phenyl)-4-trifluoromethyl-benzenesulfonamide (10) similarly to the protocol of Example 4, Scheme 2, Step 1.

Step 3—Preparation of N-[3-(4-cyclopropyl-7H-pyrrolo[2,3-d]pyrimidine-5-carbonyl)-2,4-difluoro-phenyl]-4-trifluoromethyl-benzenesulfonamide (P-0068)

N-{3-[(4-cyclopropyl-7H-pyrrolo[2,3-d]pyrimidin-5-yl)-hydroxy-methyl]-2,4-difluoro-phenyl}-4-trifluoromethyl-benzenesulfonamide (P-0067) was reacted similarly to the protocol of Example 4, Scheme 2, Step 2. MS (ESI) [M+H$^+$]$^+$=522.9.

Propane-1-sulfonic acid [3-(4-cyclopropyl-7H-pyrrolo[2,3-d]pyrimidine-5-carbonyl)-2,4-difluoro-phenyl]-amide (P-0069)

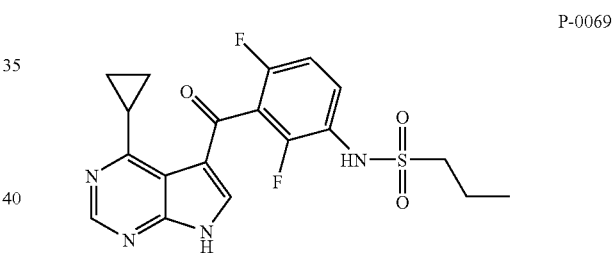

P-0069 was prepared similarly to the protocol of Scheme 9, replacing N-(2,4-difluoro-3-formyl-phenyl)-4-trifluoromethyl-benzenesulfonamide 10 with propane-1-sulfonic acid (2,4-difluoro-3-formyl-phenyl)-amide 9 in step 2. MS (ESI) [M+H$^+$]$^+$=420.9.

Example 12

Kinase Activity Assays

Assays for the activity of kinases, including, but not limited to, B-Raf, B-Raf V600E, B-Raf V600E/T5291 and c-Raf-1 are known in the art, for example as described in U.S. patent application Ser. No. 11/473,347 (see also, PCT publication WO2007002433), the disclosure of which is hereby incorporated by reference as it relates to such assays.

Compounds screened by at least one of the methods described in U.S. patent application Ser. No. 11/473,347, or by similar methods, having IC$_{50}$ of less than 10 μM are shown in tables 1a (A-Raf), 1b (B-Raf), 1c (B-Raf V600E), 1d (C-Raf), 1e (Btk), 1f (Fms), 1g (Kdr), 1h (Kit), 1i (Src). 1j (TEC), and 1k (TrkA).

TABLE 1a

Compounds with activity toward kinase A-Raf with $IC_{50} \leq 10$ μM.

| | |
|---|---|
| A-Raf | P-0002, P-0006, P-0029, P-0030, P-0031, P-0032, P-0035 |

TABLE 1b

Compounds with activity toward kinase B-Raf with $IC_{50} \leq 10$ μM.

| | |
|---|---|
| B-Raf | P-0002, P-0004, P-0006, P-0014, P-0017, P-0024, P-0025, P-0026, P-0027, P-0029, P-0030, P-0031, P-0032, P-0033, P-0035, P-0039, P-0040, P-0041, P-0044, P-0051, P-0056, R-0058, P-0059, P-0060, P-0061, P-0065, P-0066 |

TABLE 1c

Compounds with activity toward kinase B-Raf V600E with $IC_{50} \leq 10$ μM.

| | |
|---|---|
| B-Raf V600E | P-0002, P-0004, P-0006, P-0008, P-0009, P-0010, P-0011, P-0012, P-0013, P-0014, P-0016, P-0017, P-0018, P-0020, P-0021, P-0024, P-0025, P-0026, P-0027, P-0029, P-0030, P-0031, P-0032, P-0033, P-0035, P-0037, P-0038, P-0039, P-0040, P-0041, P-0042, P-0044, P-0045, P-0046, P-0047, P-0048, P-0049, P-0050, P-0051, P-0052, P-0053, P-0056, P-0058, P-0059, P-0060, P-0061, P-0062, P-0063, P-0064, P-0065, P-0066 |

TABLE 1d

Compounds with activity toward kinase C-Raf with $IC_{50} \leq 10$ μM.

| | |
|---|---|
| C-Raf | P-0002, P-0004, P-0006, P-0008, P-0010, P-0011, P-0012, P-0013, P-0014, P-0016, P-0017, P-0018, P-0020, P-0021, P-0024, P-0025, P-0026, P-0027, P-0029, P-0030, P-0031, P-0032, P-0033, P-0035, P-0038, P-0039, P-0040, P-0041, P-0042, P-0044, P-0046, P-0047, P-0050, P-0051, P-0052, P-0053, P-0056, P-0058, P-0059, P-0060, P-0061, P-0062, P-0063, P-0064, P-0065, P-0066 |

TABLE 1e

Compounds with activity toward kinase Btk with $IC_{50} \leq 10$ μM.

| | |
|---|---|
| Btk | P-0041 |

TABLE 1f

Compounds with activity toward kinase Fms with $IC_{50} \leq 10$ μM.

| | |
|---|---|
| Fms | P-0013, P-0014, P-0021, P-0056, P-0064, P-0066, P-0067 |

TABLE 1g

Compounds with activity toward kinase Kdr with $IC_{50} \leq 10$ μM.

| | |
|---|---|
| Kdr | P-0004, P-0009, P-0012, P-0013, P-0014, P-0018, P-0020, P-0025, P-0027, P-0029, P-0033, P-0040, P-0041, P-0042, P-0048, P-0049, P-0051, P-0053, P-0054, P-0056, P-0058, P-0059, P-0060, P-0063, P-0064, P-0065 |

TABLE 1h

Compounds with activity toward kinase Kit with $IC_{50} \leq 10$ μM.

| | |
|---|---|
| Kit | P-0011, P-0012, P-0013, P-0014, P-0017, P-0021, P-0027, P-0040, P-0041, P-0045, P-0048, P-0049, P-0050, P-0052, P-0054, P-0056, P-0060 |

TABLE 1i

Compounds with activity toward kinase Src with $IC_{50} \leq 10$ μM.

| | |
|---|---|
| Src | P-0004, P-0040, P-0041, P-0051, P-0056, P-0060, P-0061 |

TABLE 1j

Compounds with activity toward kinase TEC with $IC_{50} \leq 10$ μM.

| | |
|---|---|
| TEC | P-0002, P-0004 |

TABLE 1k

Compounds with activity toward kinase TrkA with $IC_{50} \leq 10$ μM.

| | |
|---|---|
| TrkA | P-0038, P-0050 |

Example 13

Efficacy of Compounds in Combination with Standard-of-Care Chemotherapeutic Agents in Four Human Cancer Cell Lines Compounds of the invention, such as compounds of Formula I, in combination with a standard chemotherapeutic agent, such as 5-fluorouracil, carboplatin dacarbazine, gefitinib, oxaliplatin, paclitaxel, SN-38, temozolomide, or vinblastine, can be assessed for their effectiveness in killing human tumor cells. Such assays are known in the art, for example, as described in U.S. patent application Ser. No. 11/473,347, the disclosure of which is hereby incorporated by reference as it relates to such assays.

Example 14

Pharmaceutical Properties of Compounds

Compounds of the invention, such as compounds of Formula I, demonstrate improved solubility and/or pharmacokinetics when compared to similarly substituted 1H-Pyrrolo[2,3-b]pyridine compounds. Typically, 1H-Pyrrolo[2,3-b] pyridine compounds with improved aqueous solubility may not have acceptable pharmacokinetics, assessed by measuring plasma levels in rats treated with the compounds. Improved solubility with improved exposure levels, as measured by area under the curve (AUC), is indicative of beneficial pharmaceutical properties of the compound, such as improved bioavailability.

As an indication of relative solubility, the turbidity of compounds in aqueous solutions was assessed. Each compound was diluted into four different physiologically relevant buffers and solution turbidity was measured by spectrophotometry. The concentration of compound that demonstrated turbidity by forming enough insoluble suspension to raise the average optical density above 0.01 at three wavelengths (490, 535, and 650 nm) was used to define the limit of the compound solubility in that buffer. To assess possible compound properties in different physiological compartments, such as stomach, intestine and blood, a series of aqueous buffers with varying pH was used.

Compounds were dissolved at a concentration of 25 mM in dimethyl sulfoxide, then serially diluted 1:1 into a 96 well plate, diluting 10 times in pure dimethyl sulfoxide, with the final well of each row a dimethyl sulfoxide blank. In an assay plate, 99 µL of appropriate buffer was added to each well, and 1 µL of each sample dilution was added to the buffer, achieving a range of final total concentrations in aqueous solutions having different pH. The buffers used were Simulated Gastric Fluid (SGF-pH 1.5) 0.5M NaCl, pH 1.5; Simulated Intestinal fluid (SIF-pH 4.5 and pH 6.8) 0.05M $NaH_2PO_4$, pH 4.5 and 6.8; and Hepes Buffer (HEPES-pH 7.4) 10 mM HEPES, 150 mM NaCl, pH 7.4. Control compounds pyrene, estriol and propranolol HCl were also assessed. Plates were spun and then mixed for 1 minute, and the absorbance was read using a Tecan Safire II to read wavelengths in the visible range (490, 535, and 650 nm) at four locations per well, reflecting the degree of turbidity present. The average optical density for each wavelength in each well was graphed vs. compound concentration, and the concentration at which the curve crosses a threshold O.D. of 0.01 for each wavelength was reported as the endpoint turbidity assay result. The average of the three wavelengths is used to compare turbidity of compounds. Compounds are considered to have low solubility if the threshold concentration is <31.3 µM, moderate solubility if the threshold concentration is 31.3 µM to 250 µM, and high solubility if the threshold concentration is >250 µM.

Pharmacokinetic properties were assessed in male Sprague Dawley rats. Rats were dosed daily with compound either by IV injections via surgically implanted jugular catheters or by oral gavage (PO). Each compound was prepared as a 20 mg/mL stock solution in dimethyl sulfoxide, which was further diluted to provide the dosing stock at the desired concentration for the IV or PO formulations. For IV dosing, the dosing stock was diluted into a 1:1:8 mixture of Solutol®:ethanol:water. For PO dosing, the dosing stock was diluted into 1% methylcellulose. In a cassette format, 5 compounds were diluted to 0.5 mg/mL each for IV dosing and 0.4 mg/mL each for PO dosing and dosed at 1 mg/kg (2mL/kg) or 2 mg/kg (5 mL/kg), respectively. For IV dosed animals, tail vein blood samples were collected with lithium heparin anticoagulant at 5, 15, 30, and 60 minutes and 4, 8, and 24 hours post dosing each day. For PO dosed animals, tail vein blood samples were collected with lithium heparin anticoagulant at 30 minutes, 1, 2, 4, 8 and 24 hours post dosing each day. Samples were processed to plasma and frozen for later analysis of each compound by LC/MS/MS. Plasma levels as a function of time were plotted to assess the AUC (hr*ng/mL).

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having the chemical structure of Formula I,

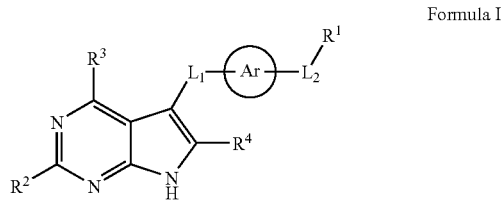

Formula I or a salt, a tautomer or a stereoisomer thereof, wherein:

Ar is

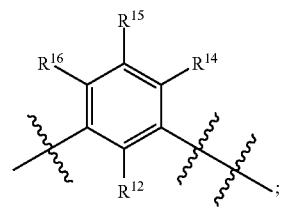

wherein

indicates the point of attachment of Ar to $L_1$ of Formula I and

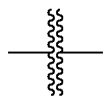

indicates the point of attachment of Ar to $L_2$ of Formula I;

$L_1$ is selected from the group consisting of —C($R^5R^6$)—, —C(O)—, —C(S)—, —N($R^7$)—, —O—, —S—, —S(O)—, and —S(O)$_2$—;

$L_2$ is selected from the group consisting of —N($R^8$)—C(O)—, —N($R^8$)—C(S)—, —N($R^8$)—S(O)—, —N($R^8$)—S(O)$_2$—, —N($R^8$)—C(O)—N($R^8$)—, —N($R^8$)—C(S)—N($R^8$)—, and —N($R^8$)—S(O)$_2$—N($R^8$)—;

$R^1$ is selected from the group consisting of lower alkyl, cycloalkyl, heterocycloalkyl, aryl, and heteroaryl, wherein lower alkyl is optionally substituted with one or more substituents $R^{63}$, and wherein cycloalkyl, heterocycloalkyl, aryl or heteroaryl are optionally substituted with one or more substituents $R^{64}$;

$R^{63}$ at each occurrence is independently selected from the group consisting of —OH, —NH$_2$, —S—$R^{65}$, —S—$R^{65}$, —N($R^{66}$)—$R^{65}$, —N)—C(O)—$R^{65}$, —N($R^{66}$)—S(O)$R^{65}$, —N($R^{66}$)—S(O)$_2$—$R^{65}$, —C(O)—$R^{65}$, —S(O)—$R^{65}$, —S(O)$_2$—$R^{65}$, fluoro, cycloalkyl, heterocycloalkyl, aryl and heteroaryl, wherein cycloalkyl, heterocycloalkyl, aryl and heteroaryl are optionally substituted with one or more substituents $R^{64}$;

$R^{64}$ at each occurrence is independently selected from the group consisting of —OH, —NH$_2$, —NO$_2$, —CN, —O—$R^{65}$, —S—$R^{65}$, —N($R^{66}$)—$R^{65}$, —N($R^{66}$)—C(O)—$R^{65}$, —N($R^{66}$)—S(O)—$R^{65}$, —N($R^{66}$)—S(O)$_2R^{65}$, C(O)—$R^{65}$, —S(O)—$R^{65}$, —S(O)$_2$—$R^{65}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{64}$, or as substituents of lower alkyl, are optionally substituted with one or more substituents selected from the group consisting of —OH, —NH$_2$, —NO$_2$, —CN, —O—$R^{67}$, —S—$R^{67}$, —N($R^{66}$)—$R^{67}$, —N($R^{66}$)—C(O)—$R^{67}$, —N($R^{66}$)—S(O)$_2$—$R^{67}$, —S(O)—$R^{67}$, —S(O)$_2$—$R^{67}$, —C(O)—$R^{67}$, halogen, lower alkyl, fluoro substituted lower alkyl, and cycloalkylamino;

$R^{65}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{65}$ or as substituents of lower alkyl are optionally substituted with one or more substituents selected from the group consisting of —OH, —NH$_2$, —CN, —NO$_2$, —C(O)—OH, —S(O)$_2$—NH$_2$, —C(O)—NH$_2$, —O—$R^{69}$, —S—$R^{69}$, —N($R^{68}$)—$R^{69}$, —N($R^{68}$)—C(O)—$R^{69}$, —N($R^{68}$)—S(O)$_2$—$R^{69}$, —C(O)—$R^{69}$, —S(O)—$R^{69}$, —S(O)$_2$—$R^{69}$, —C(O)—O—$R^{69}$, —C(O)—N($R^{68}$)—$R^{69}$, —S(O)$_2$—N($R^{68}$)—$R^{69}$, halogen, lower alkyl, fluoro substituted lower alkyl, and cycloalkylamino;

$R^{66}$ and $R^{68}$ at each occurrence are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino;

$R^{67}$ and $R^{69}$ at each occurrence are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy;

$R^2$ is hydrogen;

$R^3$ is selected from the group consisting of hydrogen, lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, cycloalkyl optionally substituted with OH, —NH$_2$, —CN, —NO$_2$, —C(O)—OH, —S(O)—NH$_2$, —S(O)$_2$—NH$_2$, —C(O)—NH$_2$, lower alkoxy, halogen, lower alkyl, fluoro substituted lower alkyl, or cycloalkylamino, and —O—$R^{19}$;

$R^4$ is hydrogen;

$R^5$ and $R^6$ are independently selected from the group consisting of hydrogen, fluoro, —OH, —NH$_2$, lower alkyl, lower alkoxy, lower alklylthio, mono-alkylamino, di-alkylamino, and —N($R^{25}$)—$R^{26}$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino; or $R^5$ and $R^6$ combine to form a 3-7 membered monocyclic cycloalkyl or 5-7 membered monocyclic heterocycloalkyl, wherein the 3-7 membered monocyclic cycloalkyl or 5-7 membered monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

R⁷ is selected from the group consisting of hydrogen, optionally substituted lower alkyl, optionally substituted cycloalkyl, optionally substituted heterocycloalkyl, optionally substituted aryl, optionally substituted heteroaryl, —C(O)—R²⁷, —C(S)—R²⁷, —S(O)—R²⁷, —S(O)₂—R²⁷, —C(O)—N(H)—R²⁷, —C(S)—N(H)—R²⁷, and —S(O)₂—N(H)—R²⁷;

R⁸ at each occurrence is independently hydrogen, lower alkyl, or lower alkyl substituted with one or more substituents selected from the group consisting of fluoro, —OH, —NH₂, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —N(R²⁵)—R²⁶;

R¹² and R¹⁶ are independently selected from the group consisting of hydrogen and halogen;

R¹⁴ and R¹⁵ are hydrogen;

R¹⁹ is optionally substituted lower alkyl;

R²⁵ and R²⁶ at each occurrence combine with the nitrogen to which they are attached to form a 5-7 membered heterocycloalkyl optionally substituted with one or more substituents selected from the group consisting of fluoro, —OH, —NH₂, lower alkyl, fluoro substituted lower alkyl, lower alkoxy, fluoro substituted lower alkoxy, lower alkylthio, and fluoro substituted lower alkylthio; and R²⁷ at each occurrence is independently selected from the group consisting of optionally substituted lower alkyl, optionally substituted cycloalkyl, optionally substituted heterocycloalkyl, optionally substituted aryl, and optionally substituted heteroaryl.

2. The compound of claim 1, wherein:

R³ is selected from the group consisting of hydrogen, —O—R⁷⁰, and lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino; and R⁷⁰ is lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

3. The compound of claim 1, having the chemical structure of Formula Ic,

Formula Ic

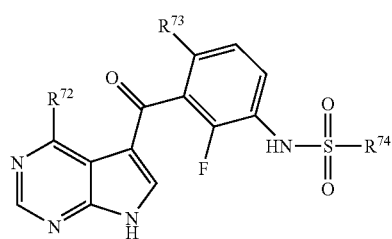

or a salt, a tautomer or a stereoisomer thereof, wherein:

R⁷² is hydrogen, lower alkyl, fluoro substituted lower alkyl, lower alkoxy, fluoro substituted lower alkoxy, or cycloalkyl;

R⁷³ is hydrogen or fluoro;

R⁷⁴ is lower alkyl, fluoro substituted lower alkyl, cycloalkyl, di-alkylamino, cycloalkylamino, pyridinyl, thiazolyl, triazolyl, or phenyl, wherein phenyl is optionally substituted with 1 or 2 substituents independently selected from the group consisting of fluoro, lower alkyl, fluoro substituted lower alkyl, lower alkoxy, and fluoro substituted lower alkoxy.

4. A composition comprising a pharmaceutically acceptable carrier; and a compound according to claim 1.

5. The compound of claim 3, wherein:

R⁷² is hydrogen, lower alkyl, lower alkoxy or cycloalkyl;

R⁷³ is hydrogen or fluoro; and

R⁷⁴ is lower alkyl, fluoro substituted lower alkyl, cycloalkyl, di-alkylamino, cycloalkylamino, or phenyl, wherein phenyl is optionally substituted with 1 or 2 substituents independently selected from the group consisting of fluoro, lower alkyl, trifluoromethyl, methoxy, and difluoromethoxy.

6. The compound of claim 1, wherein the compound is selected from the group consisting of:

Propane-1-sulfonic acid {2,4-difluoro-3-[hydroxy-(7H-pyrrolo[2,3-d]pyrimidin-5-yl)-methyl]-phenyl}-amide, Propane-1-sulfonic acid [2,4-difluoro-3-(7H-pyrrolo[2,3-d]pyrimidine-5-carbonyl)-phenyl]-amide, N-2,4-difluoro-3-[hydroxy-(7H-pyrrolo[2,3-d]pyrimidin-5-yl)-methyl]-phenyl-4-trifluoromethyl-benzenesulfonamide, N-[2,4-Difluoro-3-(7H-pyrrolo[2,3-d]pyrimidine-5-carbonyl)-phenyl]-4-trifluoromethyl-benzenesulfonamide, Propane-1-sulfonic acid {2-fluoro-3-[hydroxy-(7H-pyrrolo[2,3-d]pyrimidin-5-yl)-methyl]-phenyl}-amide, Propane-1-sulfonic acid [2-fluoro-3-(7H-pyrrolo[2,3-d]pyrimidine-5-carbonyl)-phenyl]-amide, N-[2,4-Difluoro-3-(7H-pyrrolo[2,3-d]pyrimidine-5-carbonyl)-phenyl]-methanesulfonamide, Ethanesulfonic acid [2,4-difluoro-3-(7H-pyrrolo[2,3-d]pyrimidine-5-carbonyl)-phenyl]-amide, Propane-2-sulfonic acid [2,4-difluoro-3-(7H-pyrrolo[2,3-d]pyrimidine-5-carbonyl)-phenyl]-amide, Butane-2-sulfonic acid [2,4-difluoro-3-(7H-pyrrolo[2,3-d]pyrimidine-5-carbonyl)-phenyl]-amide, 2-Methyl-propane-1-sulfonic acid [2,4-difluoro-3-(7H-pyrrolo[2,3-d]pyrimidine-5-carbonyl)-phenyl]-amide, Pentane-2-sulfonic acid [2,4-difluoro-3-(7H-pyrrolo[2,3-d]pyrimidine-5-carbonyl)-phenyl]-amide, Cyclopentanesulfonic acid [2,4-difluoro-3-(7H-pyrrolo[2,3-d]pyrimidine-5-carbonyl)-phenyl]-amide, Cyclohexanesulfonic acid [2,4-difluoro-3-(7H-pyrrolo[2,3-d]pyrimidine-5-carbonyl)-phenyl]-amide, N-[2,4-Difluoro-3-(7H-pyrrolo[2,3-d]pyrimidine-5-carbonyl)-phenyl]-C,C,C-trifluoro-methanesulfonamide, 2,2,2-Trifluoro-ethanesulfonic acid [2,4-difluoro-3-(7H-pyrrolo[2,3-d]pyrimidine-5-carbonyl)-phenyl]-amide, 3,3,3-Trifluoro-propane-1-sulfonic acid [2,4-difluoro-3-(7H-pyrrolo[2,3-d]pyrimidine-5-carbonyl)-phenyl]-amide, Dimethylamine-1-sulfonic acid [3-(7H-pyrrolo[2,3-d]pyrimidine-5-carbonyl)-2,4-difluoro-phenyl]-amide, Diethylamine-1-sulfonic acid [3-(7H-pyrrolo[2,3-d]pyrimidine-5-carbonyl)-2,4-difluoro-phenyl]-amide, Pyrrolidine-1-sulfonic acid [2,4-difluoro-3-(7H-pyrrolo[2,3-d]pyrimidine-5-carbonyl)-phenyl]-amide, Morpholine-4-sulfonic acid [2,4-difluoro-3-(7H-pyrrolo[2,3-d]pyrimidine-5-carbonyl)-phenyl]-amide, 2H-[1,2,4]Triazole-3-sulfonic acid [2,4-difluoro-3-(7H-pyrrolo[2,3-d]pyrimidine-5-carbonyl)-phenyl]-amide, Thiazole-2-sulfonic acid [2,4-difluoro-3-(7H-pyrrolo[2,3-d]pyrimidine-5-carbonyl)-phenyl]-amide,
Pyridine-2-sulfonic acid [2,4-difluoro-3-(7H-pyrrolo[2,3-d]pyrimidine-5-carbonyl)-phenyl]-amide,
N-[2,4-Difluoro-3-(7H-pyrrolo[2,3-d]pyrimidine-5-carbonyl)-phenyl]-2-fluoro-benzenesulfonamide,
N-[2,4-Difluoro-3-(7H-pyrrolo[2,3-d]pyrimidine-5-carbonyl)-phenyl]-3-fluoro-benzenesulfonamide,
N-[2,4-Difluoro-3-(7H-pyrrolo[2,3-d]pyrimidine-5-carbonyl)-phenyl]-2,5-difluoro-benzenesulfonamide,
N-[2,4-Difluoro-3-(7H-pyrrolo[2,3-d]pyrimidine-5-carbonyl)-phenyl]-benzenesulfonamide,
N-[2,4-Difluoro-3-(7H-pyrrolo[2,3-d]pyrimidine-5-carbonyl)-phenyl]-4-isopropyl-benzenesulfonamide,
N-[2,4-Difluoro-3-(7H-pyrrolo[2,3-d]pyrimidine-5-carbonyl)-phenyl]-4-propyl-benzenesulfonamide,
3-Difluoromethoxy-N-[2,4-difluoro-3-(7H-pyrrolo[2,3-d]pyrimidine-5-carbonyl)-phenyl]-benzenesulfonamide,
4-Difluoromethoxy-N-[2,4-difluoro-3-(7H-pyrrolo[2,3-d]pyrimidine-5-carbonyl)-phenyl]-benzenesulfonamide,
4-tert-Butyl-N-[2,4-difluoro-3-(7H-pyrrolo[2,3-d]pyrimidine-5-carbonyl)-phenyl]-benzenesulfonamide,
N-[2,4-Difluoro-3-(7H-pyrrolo[2,3-d]pyrimidine-5-carbonyl)-phenyl]-4-fluoro-benzenesulfonamide,
Cyclobutanesulfonic acid [2,4-difluoro-3-(7H-pyrrolo[2,3-d]pyrimidine-5-carbonyl)-phenyl]-amide,
N-[2,4-Difluoro-3-(7H-pyrrolo[2,3-d]pyrimidine-5-carbonyl)-phenyl]-2,4-difluoro-benzenesulfonamide,
N-[2,4-Difluoro-3-(7H-pyrrolo[2,3-d]pyrimidine-5-carbonyl)-phenyl]-2,6-difluoro-benzenesulfonamide,
Pyridine-3-sulfonic acid [2,4-difluoro-3-(7H-pyrrolo[2,3-d]pyrimidine-5-carbonyl)-phenyl]-amide,
N-[2,4-Difluoro-3-(4-methoxy-7H-pyrrolo[2,3-d]pyrimidine-5-carbonyl)-phenyl]-4-propyl-benzenesulfonamide,
N-[2,4-Difluoro-3-(4-methoxy-7H-pyrrolo[2,3-d]pyrimidine-5-carbonyl)-phenyl]-4-isopropyl-benzenesulfonamide,
N-[2,4-Difluoro-3-(4-methoxy-7H-pyrrolo[2,3-d]pyrimidine-5-carbonyl)-phenyl]-4-ethyl-benzenesulfonamide,
N-[2,4-Difluoro-3-(4-methoxy-7H-pyrrolo[2,3-d]pyrimidine-5-carbonyl)-phenyl]-3-fluoro-4-methoxy-benzenesulfonamide,
N-[2,4-Difluoro-3-(4-methoxy-7H-pyrrolo[2,3-d]pyrimidine-5-carbonyl)-phenyl]-3,5-dimethyl-benzenesulfonamide,
Pyridine-3-sulfonic acid [2,4-difluoro-3-(4-methoxy-7H-pyrrolo[2,3-d]pyrimidine-5-carbonyl)-phenyl]-amide,
4,4-Difluoro-cyclohexanesulfonic acid [2,4-difluoro-3-(4-methoxy-7H-pyrrolo[2,3-d]pyrimidine-5-carbonyl)-phenyl]-amide,
Cyclohexanesulfonic acid [2,4-difluoro-3-(4-methoxy-7H-pyrrolo[2,3-d]pyrimidine-5-carbonyl)-phenyl]-amide,
N-[2,4-Difluoro-3-(4-methoxy-7H-pyrrolo[2,3-d]pyrimidine-5-carbonyl)-phenyl]-C-methoxy-methanesulfonamide,
N-[2,4-Difluoro-3-(4-methyl-7H-pyrrolo[2,3-d]pyrimidine-5-carbonyl)-phenyl]-4-trifluoromethyl-benzenesulfonamide,
N-[2,4-Difluoro-3-(4-methyl-7H-pyrrolo[2,3-d]pyrimidine-5-carbonyl)-phenyl]-4-propyl-benzenesulfonamide,
N-[2,4-Difluoro-3-(4-methyl-7H-pyrrolo[2,3-d]pyrimidine-5-carbonyl)-phenyl]-4-isopropyl-benzenesulfonamide,
N-[2,4-Difluoro-3-(4-methyl-7H-pyrrolo[2,3-d]pyrimidine-5-carbonyl)-phenyl]-4-ethyl-benzenesulfonamide,
N-[2,4-Difluoro-3-(4-methyl-7H-pyrrolo[2,3-d]pyrimidine-5-carbonyl)-phenyl]-3-fluoro-4-methoxy-benzenesulfonamide,
N-[2,4-Difluoro-3-(4-methyl-7H-pyrrolo[2,3-d]pyrimidine-5-carbonyl)-phenyl]-3,5-dimethyl-benzenesulfonamide,
Pyridine-3-sulfonic acid [2,4-difluoro-3-(4-methyl-7H-pyrrolo[2,3-d]pyrimidine-5-carbonyl)-phenyl]-amide,
4,4-Difluoro-cyclohexanesulfonic acid [2,4-difluoro-3-(4-methyl-7H-pyrrolo[2,3-d]pyrimidine-5-carbonyl)-phenyl]-amide,
Cyclohexanesulfonic acid [2,4-difluoro-3-(4-methyl-7H-pyrrolo[2,3-d]pyrimidine-5-carbonyl)-phenyl]-amide, and
N-[2,4-Difluoro-3-(4-methyl-7H-pyrrolo[2,3-d]pyrimidine-5-carbonyl)-phenyl]-C-methoxy-methanesulfonamide,
N-{2-Fluoro-3-[hydroxy-(7H-pyrrolo[2,3-d]pyrimidin-5-yl)-methyl]-phenyl}-4-trifluoromethyl-benzenesulfonamide,
N-[2-Fluoro-3-(7H-pyrrolo[2,3-d]pyrimidine-5-carbonyl)-phenyl]-4-trifluoromethyl-benzenesulfonamide,
4-Fluoro-N-[2-fluoro-3-(7H-pyrrolo[2,3-d]pyrimidine-5-carbonyl)-phenyl]-benzenesulfonamide,
2,2,2-Trifluoro-ethanesulfonic acid [2-fluoro-3-(7H-pyrrolo[2,3-d]pyrimidine-5-carbonyl)-phenyl]-amide,
Pyridine-3-sulfonic acid [2-fluoro-3-(7H-pyrrolo[2,3-d]pyrimidine-5-carbonyl)-pheny]-amide,
2,5-Difluoro-N-[2-fluoro-3-(7H-pyrrolo[2,3-d]pyrimidine-5-carbonyl)-phenyl]-benzenesulfonamide,
2,6-Difluoro-N-[2-fluoro-3-(7H-pyrrolo[2,3-d]pyrimidine-5-carbonyl)-phenyl]-benzenesulfonamide,
2,4-Difluoro-N-[2-fluoro-3-(7H-pyrrolo[2,3-d]pyrimidine-5-carbonyl)-phenyl]-benzenesulfonamide,
Propane-2-sulfonic acid [2-fluoro-3-(7H-pyrrolo[2,3-d]pyrimidine-5-carbonyl)-phenyl]-amide,
3-Fluoro-N-[2-fluoro-3-(7H-pyrrolo[2,3-d]pyrimidine-5-carbonyl)-phenyl]-benzenesulfonamide,
N,N-Dimethylamino-sulfonic acid [2-fluoro-3-(7H-pyrrolo[2,3-d]pyrimidine-5-carbonyl)-phenyl]-amide,
Pyrrolidine-1-sulfonic acid [2-fluoro-3-(7H-pyrrolo[2,3-d]pyrimidine-5-carbonyl)-phenyl]-amide,
2-Methyl-propane-1-sulfonic acid [2-fluoro-3-(7H-pyrrolo[2,3-d]pyrimidine-5-carbonyl)-phenyl]-amide,
Butane-2-sulfonic acid [2-fluoro-3-(7H-pyrrolo[2,3-d]pyrimidine-5-carbonyl)-phenyl]-amide,
Cyclobutanesulfonic acid [2-fluoro-3-(7H-pyrrolo[2,3-d]pyrimidine-5-carbonyl)-phenyl]-amide,
Morpholine-4-sulfonic acid [2-fluoro-3-(7H-pyrrolo[2,3-d]pyrimidine-5-carbonyl)-phenyl]-amide
2-Fluoro-N-[2-fluoro-3-(7H-pyrrolo[2,3-d]pyrimidine-5-carbonyl)-phenyl]-benzenesulfonamide,
Cyclohexanesulfonic acid [2-fluoro-3-(7H-pyrrolo[2,3-d]pyrimidine-5-carbonyl)-phenyl]-amide,
Cyclopentanesulfonic acid [2-fluoro-3-(7H-pyrrolo[2,3-d]pyrimidine-5-carbonyl)-phenyl]-amide,
Pentane-2-sulfonic acid [2-fluoro-3-(7H-pyrrolo[2,3-d]pyrimidine-5-carbonyl)-phenyl]-amide, Propane-1-sulfonic acid {2,4-difluoro-3-[hydroxy-(4-methyl-7H-pyrrolo[2,3-d]pyrimidin-5-yl)-methyl]-phenyl}-amide,
Propane-1-sulfonic acid [2,4-difluoro-3-(4-methyl-7H-pyrrolo[2,3-d]pyrimidine-5-carbonyl)-phenyl]-amide,
Propane-1-sulfonic acid [2,4-difluoro-3-(4-hydroxy-(4-methoxy-7H-pyrrolo[2,3-d]pyrimidin-5-yl)-methyl]-phenyl}-amide,
Propane-1-sulfonic acid [2,4-difluoro-3-(4-methoxy-7H-pyrrolo[2,3-d]pyrimidine-5-carbonyl)-phenyl]-amide,
N-[2-Fluoro-3-(4-methoxy-7H-pyrrolo[2,3-d]pyrimidine-5-carbonyl)-phenyl]-4-trifluoromethyl-benzenesulfonamide,
Propane-1-sulfonic acid [2-fluoro-3-(4-methoxy-7H-pyrrolo[2,3-d]pyrimidine-5-carbonyl)-phenyl]-amide and
N-[2,4-Difluoro-3-4-methoxy-7H-pyrrolo[2,3-d]pyrimidine-5-carbonyl)-phenyl]-4-trifluoromethyl-benzenesulfonamide.

7. A composition comprising a pharmaceutically acceptable carrier; and a compound according to claim 3.

8. A composition comprising a pharmaceutically acceptable carrier; and a compound according to claim 6.

\* \* \* \* \*